(12) United States Patent
Karau et al.

US009012227B2

(10) Patent No.: US 9,012,227 B2
(45) Date of Patent: Apr. 21, 2015

(54) ω-AMINOCARBOXYLIC ACIDS,
ω-AMINOCARBOXYLIC ACID ESTERS, OR
RECOMBINANT CELLS WHICH PRODUCE
LACTAMS THEREOF

(75) Inventors: Andreas Karau, Vieux Moulin (FR);
Volker Sieber, Nandlstadt (DE);
Thomas Haas, Muenster (DE); Harald Haeger, Luedinghausen (DE); Katrin Grammann, Oer-Erkenschwick (DE);
Bruno Buehler, Dortmund (DE); Lars Blank, Dortmund (DE); Andreas Schmid, Dortmund (DE); Guido Jach, Koenigswinter (DE); Bernd Lalla, Cologne (DE); Andreas Mueller, Leverkusen (DE); Katrin Schullehner, Cologne (DE); Peter Welters, Nettetal (DE); Thorsten Eggert, Essen (DE);
Andrea Weckbecker, Cologne (DE)

(73) Assignee: Evonik Degussa GmbH, Essen (DE)

( * ) Notice: Subject to any disclaimer, the term of this patent is extended or adjusted under 35 U.S.C. 154(b) by 35 days.

(21) Appl. No.: 12/742,318

(22) PCT Filed: Dec. 12, 2008

(86) PCT No.: PCT/EP2008/067447
§ 371 (c)(1),
(2), (4) Date: May 11, 2010

(87) PCT Pub. No.: WO2009/077461
PCT Pub. Date: Jun. 25, 2009

(65) Prior Publication Data
US 2010/0324257 A1 Dec. 23, 2010

(30) Foreign Application Priority Data
Dec. 17, 2007 (DE) .......................... 10 2007 060705

(51) Int. Cl.
*C12N 15/74* (2006.01)
*C12N 15/00* (2006.01)
*C12N 15/52* (2006.01)
*C08G 69/08* (2006.01)
*C08G 69/14* (2006.01)
*C12P 13/00* (2006.01)

(52) U.S. Cl.
CPC ................ *C12N 15/52* (2013.01); *C08G 69/08* (2013.01); *C08G 69/14* (2013.01); *C12P 13/005* (2013.01)

(58) Field of Classification Search
USPC ................................................ 435/471, 455
See application file for complete search history.

(56) References Cited

U.S. PATENT DOCUMENTS

| 5,814,508 | A | 9/1998 | Di Cosimo et al. |
| 5,858,736 | A | 1/1999 | Di Cosimo et al. |
| 5,908,954 | A * | 6/1999 | Di Cosimo et al. ........... 558/441 |
| 5,922,589 | A | 7/1999 | Di Cosimo et al. |
| 5,936,114 | A | 8/1999 | Di Cosimo et al. |
| 6,066,490 | A | 5/2000 | Di Cosimo et al. |
| 6,077,955 | A | 6/2000 | Di Cosimo et al. |
| 7,148,176 | B2 | 12/2006 | Beller et al. |
| 7,157,610 | B2 | 1/2007 | Hofen et al. |
| 7,195,748 | B2 | 3/2007 | Jaeger et al. |
| 7,758,897 | B2 | 7/2010 | Roettger et al. |
| 7,923,225 | B2 | 4/2011 | Mueller et al. |
| 8,216,813 | B2 | 7/2012 | Thum et al. |
| 8,349,596 | B2 | 1/2013 | Mueller et al. |
| 8,404,470 | B2 | 3/2013 | Thum et al. |
| 8,486,677 | B2 | 7/2013 | Thum et al. |
| 8,604,227 | B2 | 12/2013 | Petrat et al. |
| 8,796,000 | B2 | 8/2014 | Thum et al. |
| 2001/0047097 | A1 | 11/2001 | Trauthwein et al. |
| 2002/0087036 | A1 | 7/2002 | Haas et al. |
| 2003/0212298 | A1 | 11/2003 | Brasse et al. |
| 2007/0207501 | A1 | 9/2007 | Wolf et al. |
| 2009/0246837 | A1* | 10/2009 | Robins et al. ................. 435/121 |
| 2009/0258405 | A1* | 10/2009 | Groeger et al. ............... 435/155 |
| 2010/0068773 | A1 | 3/2010 | Marx et al. |
| 2010/0167360 | A1 | 7/2010 | Thum et al. |
| 2010/0190219 | A1 | 7/2010 | Schaffer et al. |
| 2010/0190224 | A1 | 7/2010 | Poetter et al. |
| 2010/0261237 | A1 | 10/2010 | Verseck et al. |

(Continued)

FOREIGN PATENT DOCUMENTS

WO 97 44318 11/1997

OTHER PUBLICATIONS van Beilen et al. Journal of Bacteriology 184(6):1733-1742,2002.*
Buehler, Bruno et al., "Process implementation aspects for biocatalytic hydrocarbon oxyfunctionalization". Journal of Biotechnology, Elsevier, vol. 113, No. 1-3, pp. 183-210. (Sep. 30, 2004)

(Continued)

*Primary Examiner* — Marcia S Noble
(74) *Attorney, Agent, or Firm* — Oblon, McClelland, Maier & Neustadt, L.L.P.

(57) ABSTRACT

The present invention relates to a cell, which has been genetically modified relative to its wild type, so that in comparison with its wild type it is able to produce more ω-aminocarboxylic acids, more ω-aminocarboxylic acid esters or more lactams derived from ω-aminocarboxylic acids, starting from carboxylic acids or carboxylic acid esters. Furthermore, the present invention relates to a method for the production of a genetically modified cell, the cells obtainable by this method, a method for the production of ω-aminocarboxylic acids, of ω-aminocarboxylic acid esters or of lactams derived from ω-aminocarboxylic acids, the ω-aminocarboxylic acids, ω-aminocarboxylic acid esters or lactams derived from ω-aminocarboxylic acids obtainable by this method, a method for the production of polyamides based on ω-aminocarboxylic acids or based on lactams and the polyamides obtainable by this method.

18 Claims, 21 Drawing Sheets

(56) References Cited

U.S. PATENT DOCUMENTS

| | | |
|---|---|---|
| 2010/0291644 A1 | 11/2010 | Marx et al. |
| 2011/0039977 A1 | 2/2011 | Schuetz et al. |
| 2011/0118504 A1 | 5/2011 | Haas et al. |
| 2011/0171702 A1 | 7/2011 | Reinecke et al. |
| 2011/0189742 A1 | 8/2011 | Haas et al. |
| 2011/0251399 A1 | 10/2011 | Dingerdissen et al. |
| 2011/0257429 A1 | 10/2011 | Schraven et al. |
| 2011/0269977 A1 | 11/2011 | Dingerdissen et al. |
| 2012/0071577 A1 | 3/2012 | Pfeffer et al. |
| 2012/0077932 A1 | 3/2012 | Pfeffer et al. |
| 2012/0245375 A1 | 9/2012 | Hannen et al. |
| 2012/0264182 A1 | 10/2012 | Reinecke et al. |
| 2013/0035403 A1 | 2/2013 | Schaffer et al. |
| 2013/0092233 A1 | 4/2013 | Pawlik et al. |
| 2013/0130319 A1 | 5/2013 | Schaffer et al. |
| 2013/0165672 A1 | 6/2013 | Klasovsky et al. |
| 2013/0183725 A1 | 7/2013 | Poetter et al. |
| 2013/0299750 A1 | 11/2013 | Hermasch et al. |
| 2014/0039223 A1 | 2/2014 | Klasovsky, et al. |
| 2014/0199736 A1 | 7/2014 | Köhler et al. |

OTHER PUBLICATIONS

Buehler, Bruno et al., "Chemical Biotechnology for the Specific Oxyfunctionalization of Hydrocarbons on a Technical Scale", Biotechnology and Bioengineering, vol. 82, No. 7, pp. 833-842, (Jun. 30, 2003)

U.S. Appl. No. 12/517,923, filed Jun. 5, 2009, Verseck, et al.
U.S. Appl. No. 12/943,145, filed Nov. 10, 2010, Poetter, et al.
U.S. Appl. No. 13/263,761, filed Oct. 10, 2011, Haas, et al.
U.S. Appl. No. 13/143,354, filed Jul. 6, 2011, Sieber, et al.
U.S. Appl. No. 14/110,450, filed Oct. 8, 2013, Klasovsky, et al.
U.S. Appl. No. 14/126,607, filed Dec. 16, 2013, Haas, et al.
U.S. Appl. No. 14/237,121, filed Feb. 4, 2014, Haas, et al.
U.S. Appl. No. 14/233,505, filed Jan. 17, 2014, Poetter, et al.
U.S. Appl. No. 14/077,750, filed Nov. 12, 2013, Schaffer, et al.
U.S. Appl. No. 14/238,576, filed Feb. 12, 2014, Schaffer, et al.
U.S. Appl. No. 14/238,591, filed Feb. 12, 2014, Schaffer, et al.
U.S. Appl. No. 14/132,473, filed Dec. 18, 2013, Schaffer, et al.
U.S. Appl. No. 14/000,067, filed Aug. 16, 2013, Erhardt, et al.
U.S. Appl. No. 14/000,028, filed Aug. 16, 2013, Erhardt, et al.
U.S. Appl. No. 09/424,701, filed Jan. 25, 2002, Beller, et al.
U.S. Appl. No. 13/989,419, filed May 24, 2013, Klasovsky, et al.
U.S. Appl. No. 14/000,400, filed Aug. 20, 2013, Klasovsky, et al.
U.S. Appl. No. 13/721,481, filed Dec. 20, 2012, Gielen, et al.
U.S. Appl. No. 13/806,555, filed Dec. 21, 2012, Hannen, et al.
U.S. Appl. No. 14/363,178, filed Jun. 5, 2014, Haas, et al.
U.S. Appl. No. 14/363,165, filed Jun. 5, 2014, Pfeffer, et al.
U.S. Appl. No. 14/367,610, filed Jun. 20, 2014, Haas, et al.
U.S. Appl. No. 14/373,089, filed Jul. 18, 2014, Engel, et al.
U.S. Appl. No. 14/380,483, filed Aug. 22, 2014, Schiemann, et al.
U.S. Appl. No. 14/384,301, filed Sep. 10, 2014, Schaffer, et al.
U.S. Appl. No. 14/390,133, filed Oct. 2, 2014, Hennemann, et al.
U.S. Appl. No. 14/395,666, filed Oct. 20, 2014, Haas, et al.
U.S. Appl. No. 14/400,379, filed Nov. 11, 2014, Haas, et al.
U.S. Appl. No. 14/405,050, filed Dec. 2, 2014, Haas, et al.

* cited by examiner

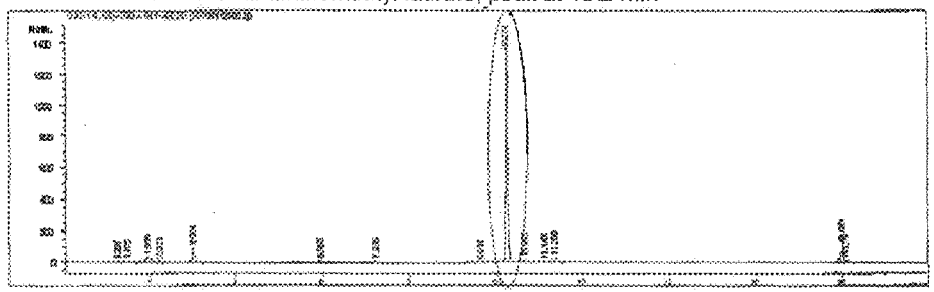
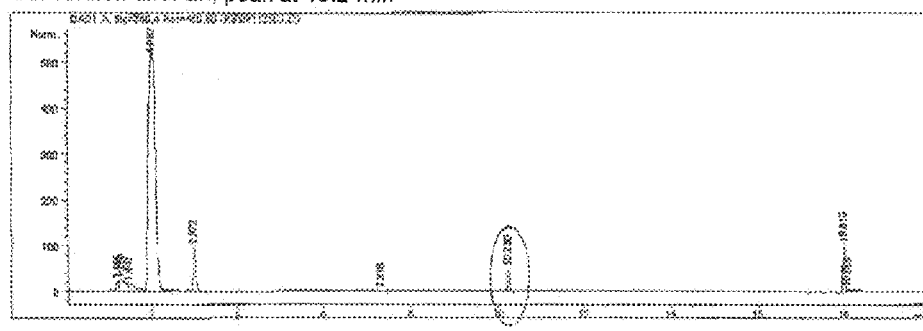
FIG. 5

FIGUR13

ω-AMINOCARBOXYLIC ACIDS, ω-AMINOCARBOXYLIC ACID ESTERS, OR RECOMBINANT CELLS WHICH PRODUCE LACTAMS THEREOF

CROSS-REFERENCE TO RELATED APPLICATIONS

This application is a National Stage of PCT/EP08/067447 filed Dec. 12, 2008 and claims the benefit of EP 102007060705.0 filed Dec. 17, 2007.

The present invention relates to cells that are genetically modified relative to their wild type, a method for the production of a genetically modified cell, the cells obtainable by this method, a method for the production of ω-aminocarboxylic acids, ω-aminocarboxylic acid esters or of lactams derived from ω-aminocarboxylic acids, the ω-aminocarboxylic acids, ω-aminocarboxylic acid esters or lactams derived from ω-aminocarboxylic acids obtainable by this method, a method for the production of polyamides based on ω-aminocarboxylic acids or on lactams and the polyamides obtainable by this method.

Polyamides are polymers whose repeating units (monomers) possess the amide group as a characteristic feature. The designation "polyamides" is usually used to designate synthetic, commercially usable thermoplastics and therefore demarcates this class of substances from the chemically related proteins. Nearly all the important polyamides are derived from primary amines, i.e. the functional group —CO—NH— occurs in their repeat units. Polyamides of secondary amines (—CO—NR—, R=organic residue) also exist. Aminocarboxylic acids, lactams and/or diamines and dicarboxylic acids in particular find application as monomers for the polyamides.

The production of polyamides on the basis of lactams is particularly important. Thus, "polyamide 6", a product that is widely used in industry, is obtained by ring opening polymerization of ε-caprolactam, whereas "polyamide 12", which is also industrially important, is obtained by ring opening polymerization of laurinlactam. Copolymers of lactams, such as copolymers of ε-caprolactam and laurinlactam ("polyamide 6/12") are also of considerable commercial importance.

The production of ε-caprolactam is usually carried out by reacting cyclohexanone with the hydrogensulphate or the hydrochloride of hydroxylamine with formation of cyclohexanone oxime. This is converted by a Beckmann rearrangement into ε-caprolactam, often with the use of concentrated sulphuric acid as catalyst. Cyclohexanone is usually produced by catalytic oxidation of cyclohexane with oxygen of the air, cyclohexane being obtained in its turn by hydrogenation of benzene.

The production of laurinlactam is particularly expensive. On an industrial scale this first involves the trimerization of butadiene, with formation of cyclododecatriene. The cyclododecatriene is then hydrogenated with formation of cyclododecane and the cyclododecane obtained is oxidized with formation of cyclododecanone. The cyclododecanone thus obtained is then reacted with hydroxylamine to cyclododecane oxime, which is then converted in a Beckmann rearrangement to laurinlactam.

The disadvantage of these methods known from the prior art for the production of lactams by Beckmann rearrangement of oximes is, among other things, that large amounts of salts, for example sodium sulphate, are formed as by-product, which requires disposal. Therefore other methods for the production of lactams are also described in the prior art, which do not have these disadvantages. Thus, EP-A-0 748 797 describes a method for the production of lactams from dinitriles, in which the dinitrile is hydrogenated to aminonitrile and the aminonitrile is converted by cyclizing hydrolysis to the lactam. Molecular sieves, such as acid zeolites, silicates and non-zeolitic molecular sieves, metal phosphates and metal oxides or mixed metal oxides have been disclosed as catalyst for cyclizing hydrolysis. However, this method has, among other drawbacks, the disadvantage that the selectivity of the conversion of the aminonitrile by cyclizing hydrolysis is rather low and therefore large amounts of by-products are formed. Furthermore, in the methods for the production of lactams described from this prior art, hydrocarbons such as benzene or butadiene are used, which are obtained by cracking gasoline or petroleum and therefore are not derived from renewable raw materials. The production of polyamides, which are based on lactams produced in this way, is therefore to be regarded as disadvantageous from the environmental standpoint.

The present invention was based on the aim of overcoming the disadvantages arising from the prior art.

In particular the present invention was based on the aim of providing a method by which lactams, in particular laurinlactam, can be formed in the fewest possible steps and with formation of the minimum possible amount of by-products.

Another aim of the present invention was to provide a method by which lactams, in particular laurinlactam, can be produced from renewable raw materials.

A contribution to achievement of the aforementioned aims is provided by a cell, which has been genetically modified relative to its wild type so that, in comparison with its wild type, it is able to produce more ω-aminocarboxylic acids, ω-aminocarboxylic acid esters or more lactams derived from ω-aminocarboxylic acids, starting from carboxylic acids or carboxylic acid esters. Such a cell can be used in order to produce ω-aminocarboxylic acids, ω-aminocarboxylic acid esters or lactams derived from ω-aminocarboxylic acids by fermentation from carboxylic acids or carboxylic acid esters, for example from lauric acid or lauric acid esters.

The formulation "that in comparison with its wild type it is able to produce more ω-aminocarboxylic acids, ω-aminocarboxylic acid esters or more lactams derived from ω-aminocarboxylic acids, starting from carboxylic acids or carboxylic acid esters" also applies to the case when the wild type of the genetically modified cell is not able to form any ω-aminocarboxylic acids, ω-aminocarboxylic acid esters or any lactams derived from ω-aminocarboxylic acids, or at least no detectable amounts of these compounds and it is only after the genetic modification that detectable amounts of these components can be formed.

A "wild type" of a cell preferably denotes a cell whose genome is in a state such as arose naturally by evolution. The term is used both for the whole cell and for individual genes. The term "wild type" therefore in particular does not include such cells or such genes whose gene sequences have been altered at least partially by man by recombinant methods.

It is preferable according to the invention for the genetically modified cell to have been genetically modified so that in a defined time interval, preferably within 2 hours, still more preferably within 8 hours and most preferably within 24 hours, it forms at least twice, especially preferably at least 10 times, even more preferably at least 100 times, and yet more preferably at least 1000 times and most preferably at least 10000 times more ω-aminocarboxylic acids, ω-aminocarboxylic acid esters or lactams derived from ω-aminocarboxylic acids than the wild-type cell. The increase in product formation can be determined for example by cultivating the cell according to the invention and the wild-type cell each separately under the same conditions (same cell density, same nutrient medium, same culture conditions) for a specified time interval in a suitable nutrient medium and then determining the amount of target product (ω-aminocarboxylic acids, ω-aminocarboxylic acid esters or lactams derived from ω-aminocarboxylic acids) in the nutrient medium.

The cells according to the invention can be prokaryotes or eukaryotes. They can be mammalian cells (such as human cells), plant cells or microorganisms such as yeasts, fungi or bacteria, microorganisms being especially preferred and bacteria and yeasts being most preferred.

Suitable bacteria, yeasts or fungi are in particular those bacteria, yeasts or fungi that have been deposited in the German Collection of Microorganisms and Cell Cultures (Deutsche Sammlung von Mikroorganismen and Zellkulturen GmbH, abbreviated to DSMZ), Brunswick, Germany, as strains of bacteria, yeasts or fungi.

Cells that are especially preferred according to the invention are derived from cells of the genera *Corynebacterium, Brevibacterium, Bacillus, Lactobacillus, Lactococcus, Candida, Pichia, Kluveromyces, Saccharomyces, Escherichia, Zymomonas, Yarrowia, Methylobacterium, Ralstonia, Pseudomonas, Burkholderia* and *Clostridium*, with *Escherichia coli, Corynebacterium glutamicum* and *Pseudomonas putida* being especially preferred and *Escherichia coli* being most preferred.

According to a preferred embodiment of the cell according to the invention the latter displays, in comparison with its wild type, increased activity of at least one of the following enzymes:

i) an enzyme $E_I$, which catalyses the conversion of carboxylic acids or carboxylic acid esters to the corresponding ω-hydroxycarboxylic acids or ω-hydroxycarboxylic acid esters;
ii) an enzyme $E_{II}$, which catalyses the conversion of ω-hydroxycarboxylic acids or ω-hydroxycarboxylic acid esters to the corresponding ω-oxocarboxylic acids or ω-oxocarboxylic acid esters;
iii) an enzyme $E_{III}$, which catalyses the conversion of ω-oxocarboxylic acids or ω-oxocarboxylic acid esters to the corresponding ω-aminocarboxylic acids or ω-aminocarboxylic acid esters.

The term "increased activity of an enzyme", as used above in connection with the enzyme $E_I$ and hereinafter in connection with the enzymes $E_{II}$ etc., is preferably to be understood as increased intracellular activity.

The following account regarding the increase in enzyme activity in cells applies both to the increase in activity of the enzyme $E_I$ and to all the enzymes stated subsequently, whose activity can possibly be increased.

Basically, an increase in enzymatic activity can be achieved by increasing the copy number of the gene sequence or gene sequences that code for the enzyme, using a strong promoter or employing a gene or allele that codes for a corresponding enzyme with increased activity and optionally by combining these measures. Genetically modified cells according to the invention are for example produced by transformation, transduction, conjugation or a combination of these methods with a vector that contains the desired gene, an allele of this gene or parts thereof and a vector that makes expression of the gene possible. Heterologous expression is in particular achieved by integration of the gene or of the alleles in the chromosome of the cell or an extrachromosomally replicating vector.

A review of possible ways of increasing the enzyme activity in cells for the example of pyruvate carboxylase is given in DE-A-100 31 999, which is hereby incorporated as reference and whose disclosures with respect to the possibilities for increasing the enzyme activity in cells forms part of the disclosure of the present invention.

The expression of the aforementioned and all subsequently mentioned enzymes or genes can be detected by means of 1- and 2-dimensional protein gel separation and subsequent optical identification of the protein concentration in the gel using appropriate evaluation software. If the increase in enzyme activity is based exclusively on an increase in expression of the corresponding gene, the increase in enzyme activity can be quantified in a simple way by comparing the 1- or 2-dimensional protein separations between wild type and genetically modified cell. A usual method for the preparation of protein gels in the case of coryneform bacteria and for identification of the proteins is the procedure described by Hermann et al. (*Electrophoresis*, 22: 1712-23 (2001)). The protein concentration can also be analysed by Western blot hybridization with an antibody that is specific for the protein that is to be detected (Sambrook et al., *Molecular Cloning: a laboratory manual*, 2nd Ed. Cold Spring Harbor Laboratory Press, Cold Spring Harbor, N.Y. USA, 1989) followed by optical evaluation with appropriate software for determination of concentration (Lohaus and Meyer (1989) *Biospektrum*, 5: 32-39; Lottspeich (1999), *Angewandte Chemie* 111: 2630-2647). The activity of DNA-binding proteins can be measured by DNA-Band-Shift-Assays (also called gel retardation) (Wilson et al. (2001) *Journal of Bacteriology*, 183: 2151-2155). The action of DNA-binding proteins on the expression of other genes can be detected by various well-described methods of reporter gene assay (Sambrook et al., *Molecular Cloning: a laboratory manual*, 2nd Ed. Cold Spring Harbor Laboratory Press, Cold Spring Harbor, N.Y. USA, 1989). Intracellular enzymatic activities can be determined by various methods that have been described (Donahue et al. (2000) *Journal of Bacteriology* 182 (19): 5624-5627; Ray et al. (2000) *Journal of Bacteriology* 182 (8): 2277-2284; Freedberg et al. (1973) *Journal of Bacteriology* 115 (3): 816-823). If in the subsequent account no concrete methods are stated for determination of the activity of a particular enzyme, the increase in enzyme activity as well as the decrease in enzyme activity are preferably determined by the methods described in Hermann et al., Electophoresis, 22: 1712-23 (2001), Lohaus et al., Biospektrum 5 32-39 (1998), Lottspeich, *Angewandte Chemie* 111: 2630-2647 (1999) and Wilson et al., *Journal of Bacteriology* 183: 2151-2155 (2001).

If the increase in enzyme activity is brought about by mutation of the endogenous gene, such mutations can either be produced undirected according to classical methods, such as by UV-irradiation or by mutation-causing chemicals, or purposefully by genetic engineering methods such as deletion(s), insertion(s) and/or nucleotide exchange(s). Genetically modified cells are obtained as a result of these mutations. Especially preferred mutants of enzymes are in particular also enzymes for which feedback inhibition is no longer present or at least is reduced in comparison with the wild-type enzyme.

If the increase in enzyme activity is brought about through an increase in expression of an enzyme, then for example we increase the copy number of the corresponding genes or mutate the promoter and regulating region or the ribosome binding site, which is located upstream of the structural gene. Expression cassettes that are inserted upstream of the structural gene work in this way. By means of inducible promoters it is additionally possible to increase the expression at any time. Moreover, the enzyme gene can also be assigned, as regulatory sequences, so-called "enhancers", which as a result of improved interaction between RNA-polymerase and DNA also bring about increased gene expression. Expression is also improved by measures for extending the life of the m-RNA. Furthermore, by preventing the degradation of the enzyme protein, enzyme activity is also intensified. The genes or gene constructs are then either contained in plasmids with varying copy number or are integrated in the chromosome and amplified. Alternatively, overexpression of the relevant genes can in addition be achieved by altering the composition of the medium and the culture conditions. A person skilled in the art will find instructions for this in, inter alia, Martin et al. (*Bio/technology* 5, 137-146 (1987)), Guerrero et al. (*Gene* 138, 35-41 (1994)), Tsuchiya and Morinaga (*Bio/technology* 6, 428-430 (1988)), Eikmanns et al. (*Gene* 102, 93-98 (1991)), in EP-A-0 472 869, in U.S. Pat. No. 4,601,893, in Schwarzer and Pühler (*Bio/technology* 9, 84-87 (1991)), in Reinscheid et al. (*Applied and Environmental Microbiology* 60, 126-132 (1994)), in LaBarre et al. (*Journal of Bacteriology* 175, 1001-1007 (1993)), in WO-A-96/15246, in Malumbres et al. (*Gene* 134, 15-24 (1993)), in JP-A-10-229891, in Jensen and Hammer (*Biotechnology and Bioengineering* 58, 191-195 (1998)) and in known textbooks of genetics and molecular biology. The measures described above also lead, like mutations, to genetically modified cells.

Episomal plasmids, for example, are used for increasing the expression of the genes in question. Suitable plasmids are in particular those that are replicated in coryneform bacteria. Numerous known plasmid vectors, for example pZ1 (Menkel et al., *Applied and Environmental Microbiology* 64: 549-554 (1989)), pEKEx1 (Eikmanns et al., *Gene* 107: 69-74 (1991)) or pHS2-1 (Sonnen et al., *Gene* 107: 69-74 (1991)) are based on the cryptic plasmids pHM1519, pBL1 or pGA1. Other plasmid vectors, for example those based on pCG4 (U.S. Pat. No. 4,489,160) or pNG2 (Serwold-Davis et al., *FEMS Microbiology Letters* 66: 119-124 (1990)) or pAG1 (U.S. Pat. No. 5,158,891), can be used in the same way.

Furthermore, plasmid vectors are also suitable, by means of which we can apply the method of gene amplification by integration into the chromosome, as was described for example by Reinscheid et al. (Applied and Environmental Microbiology 60: 126-132 (1994)) for the duplication or amplification of the hom-thrB operon. In this method the complete gene is cloned into a plasmid vector, which can be replicated in a host (typically *Escherichia coli*), but not in *Corynebacterium glutamicum*. Vectors that may be considered are for example pSUP301 (Simon et al., *Bio/Technology* 1: 784-791 (1983)), pK18mob or pK19mob (Schäfer et al., *Gene* 145: 69-73 (1994)), pGEM-T (Promega Corporation, Madison, Wis., USA), pCR2.1-TOPO (Shuman, *Journal of Biological Chemistry* 269: 32678-84 (1994)), pCR® Blunt (Invitrogen, Groningen, The Netherlands), pEM1 (Schrumpf et al., *Journal of Bacteriology* 173: 4510-4516)) or pBGS8 (Spratt et al., *Gene* 41: 337-342 (1986)). The plasmid vector that contains the gene to be amplified is then transferred by conjugation or transformation into the desired strain of *Corynebacterium glutamicum*. The method of conjugation is described for example in Schäfer et al., *Applied and Environmental Microbiology* 60: 756-759 (1994). Methods for transformation are described for example in Thierbach et al., *Applied Microbiology and Biotechnology* 29: 356-362 (1988), Dunican and Shivnan, Bio/Technology 7: 1067-1070 (1989) and Tauch et al., *FEMS Microbiology Letters* 123: 343-347 (1994). After homologous recombination by a "cross-over" event, the resultant strain contains at least two copies of the relevant gene.

The formulation used in the above and hereinafter "increased activity of an enzyme $E_x$ relative to its wild type" preferably always means activity of the respective enzyme that is increased by a factor of at least 2, especially preferably of at least 10, even more preferably of at least 100, yet more preferably of at least 1000 and most preferably of at least 10000. Furthermore, the cell according to the invention, which has "increased activity of an enzyme $E_x$ relative to its wild type", in particular also comprises a cell whose wild type has no or at least no detectable activity of this enzyme $E_x$ and only displayed a detectable activity of this enzyme $E_x$ after the enzyme activity was increased, for example through overexpression. In this connection the term "overexpression" or the formulation "increase in expression" used hereinafter also includes the case when a starting cell, for example a wild-type cell, has no or at least no detectable expression and it is only by recombinant methods that a detectable expression of the enzyme $E_x$ is induced.

Furthermore, according to the invention it is preferable for the cell to have increased activity of enzymes $E_I$ and $E_{II}$, enzymes $E_I$ and $E_{III}$, enzymes $E_{II}$ and $E_{III}$ or even increased activity of all the enzymes $E_I$, $E_{II}$ and $E_{III}$.

Furthermore, in connection with the aforementioned preferred embodiment of the cell according to the invention it is preferable for enzyme $E_I$ to be an alkane monooxygenase or a xylene monooxygenase, or, preferably and enzyme $E_{II}$ to be an alkane monooxygenase, an alcohol dehydrogenase or an alcohol oxidase, or, preferably and enzyme $E_{III}$ to be a ω-transaminase.

A preferred enzyme $E_I$, in particular a preferred alkane monooxygenase is the alkane monooxygenase encoded by the alkBGT gene from *Pseudomonas putida* GPO1. The isolation of the alkBGT gene sequence is described for example by van Beilen et al. in "*Functional Analysis of Alkane Hydroxylases from Gram-Negative and Gram-Positive Bacteria*", Journal of Bacteriology, Vol. 184 (6), pages 1733-1742 (2002). Furthermore, cytochrome P450 monoxygenases, in particular cytochrome P450 monooxygenases from *Candida*, for example from *Candida tropicalis*, or from plants, for example from the chick-pea (*Cicer arietinum L.*), can also be used as alkane monooxygenases. The gene sequences of suitable cytochrome P450 monooxygenases from *Candida tropicalis* are for example disclosed in WO-A-00/20566, whereas the gene sequences of suitable cytochrome P450 monooxygenases from the chick-pea are given for example by Barz et al. in "*Cloning and characterization of eight cytochrome P450 cDNAs from chickpea (Cicer arietinum L.) cell suspension cultures*", Plant Science, Vol. 155, pages 101-108 (2000). Other homologues of the alkB gene are also given by van Beilen et al. in "*Oil & Gas Science and Technology*", Vol. 58 (4), pages 427-440 (2003). A suitable gene for a xylene monooxygenase is for example the xylM or the xylA gene, and a plasmid containing these two genes has the GENBANK Accession No. M37480.

A preferred enzyme $E_{II}$, in particular a preferred alcohol dehydrogenase is for example the alcohol dehydrogenase encoded by the alkJ gene (EC 1.1.99-2), in particular the alcohol dehydrogenase encoded by the alkJ gene from *Pseudomonas putida* GPo1. The gene sequences the alcohol dehydrogenase encoded by the alkJ gene from *Pseudomonas putida* GPo1, *Alcanivorax borkumensis, Bordetella parapertussis, Bordetella bronchiseptica* or from *Roseobacter denitrificans* can be found for example in the KEGG gene databank.

Suitable ω-transaminases are for example the ω-transaminases that are characterized in US-A-2007/0092957 by the sequence numbers 248, 250, 252 and 254.

A preferred enzyme $E_{III}$, in particular a preferred ω-transaminase is in particular the ω-transaminase from *Chromobacterium violaceum* DSM30191 (Kaulmann et al., 2007;

"Substrate spectrum of ω-transaminase from Chromobacterium violaceum DSM30191 and its potential for biocatalysis", Enzyme and Microbial Technology, Vol. 41, pages 628-637, which is encoded by the gene sequence according to SEQ ID No. 01.

It can be advantageous to use, as enzyme $E_{III}$, ω-transaminases that can be isolated from plants. The ω-transaminases from plants selected from the group comprising *Arabidopsis thaliana, Avena saliva, Beta vulgaris, Glycine max, Hordeum vulgare, Lotus japonicus, Solanum lycopersicum, Manihot esculenta, Oryza sativa, Traeticum aestivum, Zea mays, Spinacia oleracea, Arum maculatum, Mercurialis perennis* and *Urtica dioica*, are preferred here, and *Arabidopsis thaliana* is especially preferred. Enzymes that are encoded by nucleic acids that have 90%, preferably 95%, especially preferably 99 and quite especially preferably 100% identity to the sequence according to SEQ ID No. 39, are suitable in particular as ω-transaminases. The "nucleotide identity" relative to SEQ ID No. 39 is determined using known methods. In general, special computer programs with algorithms are used, taking into account special requirements. Preferred methods for determination of identity first produce the greatest agreement between the sequences to be compared. Computer programs for determination of identity comprise, but are not restricted to, the GCG software package, including GAP (Deveroy, J. et al., Nucleic Acid Research 12 (1984), page 387, Genetics Computer Group University of Wisconsin, Madison (WI), and BLASTP, BLASTN and FASTA (Altschul, S. et al., Journal of Molecular Biology 215 (1990), pages 403-410. The BLAST program can be obtained from the National Center for Biotechnology Information (NCBI) and from other sources (BLAST Manual, Altschul S. et al., NCBI NLM NIH Bethesda ND 22894; Altschul S. et al., as above).

The well-known Smith-Waterman algorithm can also be used for determining nucleotide identity.

Preferred parameters for nucleotide comparison comprise the following:

Algorithm Needleman and Wunsch, Journal of Molecular Biology 48 (1970), pages 443-453
Comparison matrix
Matches=+10
Mismatches=0
Gap penalty=50
Gap length penalty=3

The GAP program is also suitable for use with the parameters given above. The aforementioned parameters are the default parameters in the nucleotide sequence comparison.

Moreover, enzymes from the subgroup of the β-Ala:pyruvate transaminases are suitable. These include e.g. transaminases from *Pseudomonas putida* W619 (gi: 119860707, gi: 119855857, gi: 119856278), from *Pseudomonas putida* KT2440 (gi: 24984391), from *Pseudomonas aeruginosa* PA01 (gi 15595330, gi: 15600506, gi 15595418, gi 9951072); *Streptomyces coelicolor* A3(2) (gi: 3319731), *Streptomyces avermitilis* MA 4680 (gi: 29831094, gi: 29829154) and *Chromobacterium violaceum* ATCC 12472 (gi 34102747). The amino acid sequences of the aforementioned transaminases are presented in the sequences according to SEQ ID No. 19 to SEQ ID No. 30.

For the case when the cells according to the invention are to be used for the production of ω-aminocarboxylic acids, ω-aminocarboxylic acid esters or lactams based on ω-aminocarboxylic acids starting from carboxylic acid esters, it is moreover advantageous if the cell according to the invention has, in addition to increased activity of at least one of the enzymes $E_I$, $E_{II}$ and $E_{III}$, preferably in addition to increased activity of the enzymes $E_I$ and $E_{III}$ or $E_I$, $E_{II}$ and $E_{III}$, also increased activity of an enzyme $E_{IV}$, which catalyses the conversion of ω-aminocarboxylic acid esters to the corresponding ω-aminocarboxylic acids, said enzyme $E_{IV}$ preferably being an esterase, which preferably is secreted by the cell. Secretion of the esterase by the cell has the advantage that the ester bond is only cleaved outside of the cell. This ensures that, owing to the better membrane permeability of the ω-aminocarboxylic acid ester compared with ω-aminocarboxylic acid, sufficient target product leaves the cell and can be transferred to the nutrient medium surrounding the cell.

Preferred esterases according to the invention are in particular lipase, and as an example of a suitable lipase we may mention the lipase LipA from *Pseudomonas fluorescens* HU380 (ACC Code Q76D26, Kojima and Shimizu, "*Purification and Characterization of the Lipase from Pseudomonas fluorescens HU380*", Journal of Bioscience and Bioengineering. Volume 96 (3), pages 219-226 (2003)). In order to ensure that the esterases are secreted, they can be provided, in a manner known by a person skilled in the art, with corresponding signal sequences, which establish secretion. If for example the aforementioned lipase LipA from *Pseudomonas fluorescens* HU380 is overexpressed in *E. coli*, it can be provided advantageously with signal sequences from EstA, an esterase that occurs naturally on the cell surface of *Pseudomonas aeruginosa* (Becker et al., "*A generic system for the Escherichia coli cell-surface display of lipolytic enzymes*", FEBS Letters, Vol. 579, pages 1177-1182 (2005)). Other suitable enzymes are lipases from *C. antarctica, M. miehei* and *P. cepacia* (Vaysse et al., "*Enzyme and Microbial Technology*", Vol. 31, pages 648-655 (2002)).

Alternatively the secreted ω-aminocarboxylic acid ester can also be cleaved conventionally, to obtain the ω-aminocarboxylic acid, for example by saponification, i.e. hydrolysis of the ω-aminocarboxylic acid ester by the aqueous solution of a hydroxide, e.g. by sodium hydroxide.

Furthermore, it may prove advantageous according to the invention if the cell according to the invention, in addition to increased activity of at least one of the enzymes $E_I$, $E_{II}$ and $E_{III}$, preferably in addition to increased activity of the enzymes $E_I$ and $E_{III}$ or $E_I$, $E_{II}$ and $E_{III}$, and optionally also in addition to increased activity of the aforementioned enzyme $E_{IV}$, also has increased activity of an enzyme $E_V$, which catalyses the conversion of ω-aminocarboxylic acids to the corresponding lactams, and it can also be advantageous here if this enzyme $E_V$ is secreted by the cell. In this way it can be possible for the ω-aminocarboxylic acids formed directly by the cell or the ω-aminocarboxylic acid that is only formed after extracellular cleavage of ω-aminocarboxylic acid esters to be converted to the corresponding lactam, thus optionally facilitating purification of the target product.

According to another, special embodiment of the cell according to the invention, it has, in addition to increased activity of one or more of the enzymes $E_I$, $E_{II}$ or $E_{III}$ and optionally increased activity of the enzyme $E_{IV}$ and/or $E_V$, also increased activity of an enzyme $E_{VI}$, which catalyses the conversion of an α-ketocarboxylic acid to an amino acid, said enzyme $E_{VI}$ preferably being an amino acid dehydrogenase. Such a modification of the cell would have the advantage that in the case when amino acids are used as donor for the $NH_2$ group, which is consumed during the transaminase ($E_{III}$)—mediated reaction of an ω-oxocarboxylic acid or an ω-oxocarboxylic acid ester to the corresponding ω-aminocarboxylic acid, to the corresponding ω-aminocarboxylic acid ester or to the corresponding ω-aminocarboxylic acid ester, can be correspondingly regenerated. Preferred, as amino acid dehydrogenase, is the alanine dehydrogenase from *B. subtilis* (EC No. 1.4.1.1; Gene ID: 936557), which is encoded by the gene sequence according to SEQ ID No. 02. Other suitable amino acid dehydrogenases are serine dehydrogenases, aspartate dehydrogenases, phenylalanine dehydrogenases and glutamate dehydrogenases.

A contribution to achievement of the aims stated at the beginning is also provided by a method for the production of a genetically modified cell, comprising the process step of increasing the activity of at least one of the following enzymes:

i) an enzyme $E_I$, which catalyses the conversion of carboxylic acids or carboxylic acid esters to the corresponding ω-hydroxycarboxylic acids or ω-hydroxycarboxylic acid esters, ii) an enzyme $E_{II}$, which catalyses the conversion of ω-hydroxycarboxylic acids or ω-hydroxycarboxylic acid esters to the corresponding ω-oxocarboxylic acids or ω-oxocarboxylic acid esters, or iii) an enzyme $E_{III}$, which catalyses the conversion of ω-oxocarboxylic acids or ω-oxocarboxylic acid esters to the corresponding ω-aminocarboxylic acids or ω-aminocarboxylic acid esters, in a cell, with the enzyme activities preferably being increased by the methods described at the beginning.

According to a special embodiment of the method described above, in this method, in addition to the increase in activity of the enzymes $E_I$, $E_{II}$ and/or $E_{III}$, the activity of an enzyme $E_{IV}$, which catalyses the conversion of ω-aminocarboxylic acid esters to the corresponding ω-aminocarboxylic acids, and/or of an enzyme $E_V$, which catalyses the conversion of ω-aminocarboxylic acids to the corresponding lactams, is also increased by increasing the expression of these enzymes, with the enzymes $E_{IV}$ and/or $E_V$ preferably being secreted by the cell.

A contribution to achievement of the aims stated at the beginning is also provided by the genetically modified cells that are obtainable by the method described above.

Another contribution to achievement of the cells stated at the beginning is provided by a method for the production of ω-aminocarboxylic acids, of ω-aminocarboxylic acid esters or of lactams derived from ω-aminocarboxylic acids, containing the process steps:

I) contacting a cell according to the invention with a culture medium containing a carboxylic acid or a carboxylic acid ester or with a culture medium contiguous with an organic phase containing a carboxylic acid or a carboxylic acid ester in conditions that enable the cell to form ω-aminocarboxylic acids, ω-aminocarboxylic acid esters or lactams derived from ω-aminocarboxylic acids, from the carboxylic acid or from the carboxylic acid esters;

II) optionally isolation of the resultant ω-aminocarboxylic acids, ω-aminocarboxylic acid esters or lactams derived from ω-aminocarboxylic acids.

In step I) of the method according to the invention the cells are first brought into contact with a culture medium containing a carboxylic acid or a carboxylic acid ester or with a culture medium contiguous with an organic phase containing a carboxylic acid or a carboxylic acid ester, and this contacting takes place under conditions that make it possible for the cell to form ω-aminocarboxylic acids, ω-aminocarboxylic acid esters or lactams derived from ω-aminocarboxylic acids, from the carboxylic acid or from the carboxylic acid esters.

The genetically modified cells according to the invention can be brought into contact with the nutrient medium, and therefore cultivated continuously or discontinuously in a batch process or in a fed-batch process or in a repeated-fed-batch process, for the purpose of producing ω-aminocarboxylic acids or lactams derived from ω-aminocarboxylic acids. A semi-continuous process is also conceivable, as described in GB-A-1009370. Known culture methods are described in Chmiel's textbook ("*Bioprozesstechnik* 1. *Einführung in die Bioverfahrenstechnik*" [Bioprocess Techniques 1. Introduction to Bioprocess Engineering] (Gustav Fischer Verlag, Stuttgart, 1991)) or in the textbook by Storhas ("*Bioreaktoren and periphere einrichtungen*" [Bioreactors and Peripheral Equipment], Vieweg Verlag, Brunswick/Wiesbaden, 1994).

The culture medium to be used must be suitable for the requirements of the particular strains. Descriptions of culture media for various microorganisms are given in "*Manual of Methods for General Bacteriology*" of the American Society for Bacteriology (Washington D.C., USA, 1981).

Apart from the carboxylic acids or carboxylic acid esters, the carbon source used can be carbohydrates, e.g. glucose, sucrose, lactose, fructose, maltose, molasses, starch and cellulose, oils and fats, e.g. soya oil, sunflower oil, peanut oil and coconut oil, fatty acids e.g. palmitic acid, stearic acid and linoleic acid, alcohols e.g. glycerol and methanol, hydrocarbons such as methane, amino acids such as L-glutamate or L-valine or organic acids e.g. acetic acid. These substances can be used separately or as a mixture. The use of carbohydrates, especially monosaccharides, oligosaccharides or polysaccharides, is especially preferred, as described in U.S. Pat. Nos. 6,013,494 and 6,136,576, and of $C_5$-sugars or glycerol.

Organic nitrogen-containing compounds such as peptones, yeast extract, meat extract, malt extract, corn-steep liquor, soybean flour and urea or inorganic compounds such as ammonium sulphate, ammonium chloride, ammonium phosphate, ammonium carbonate and ammonium nitrate can be used as the nitrogen source. The nitrogen sources can be used separately or as a mixture.

Phosphoric acid, potassium dihydrogen phosphate or dipotassium hydrogen phosphate or the corresponding sodium-containing salts can be used as the source of phosphorus. The culture medium must in addition contain salts of metals, for example magnesium sulphate or iron sulphate, which are required for growth. Finally, essential growth substances such as amino acids and vitamins are used in addition to the substances mentioned above. Furthermore, suitable precursors can be added to the culture medium. The stated substances can be added to the culture in the form of a single preparation, or they can be supplied in a suitable manner during cultivation.

Basic compounds such as sodium hydroxide, potassium hydroxide, ammonia or ammonia water or acid compounds such as phosphoric acid or sulphuric acid are used in a suitable manner for controlling the pH of the culture. Antifoaming agents, e.g. fatty acid polyglycol esters, are used for controlling foaming. To maintain plasmid stability, suitable selectively acting substances, e.g. antibiotics, can be added to the medium. To maintain aerobic conditions, oxygen or oxygen-containing gas mixtures, e.g. air, are fed into the culture. The temperature of the culture is normally in the range from 20° C. to 45° C. and preferably 25° C. to 40° C.

According to an especially preferred embodiment of the method according to the invention for the production of ω-aminocarboxylic acids, of ω-aminocarboxylic acid esters or of lactams derived from ω-aminocarboxylic acids, in which a recombinant cell, derived from an *E. coli* cell, is used as the cell according to the invention, a mineral salt medium supplemented with ampicillin, chloramphenicol and kanamycin according to Riesenberg et al., "*High cell density fermentation of recombinant Escherichia coli expressing human* interferon alpha 1", *Appl Microbiol and Biotechnololgy*, Vol. 34 (1), pages 77-82 (1990)) is used as the nutrient medium.

The contacting of the cells according to the invention with the culture medium in step I) preferably takes place in conditions that enable the cell to form ω-aminocarboxylic acids, ω-aminocarboxylic acid esters or lactams derived from ω-aminocarboxylic acids starting from carboxylic acid or from carboxylic acid esters. As carboxylic acids or carboxylic acid esters, consideration may be given in particular to carboxylic acids with number of carbons in the range from 6 to 20, especially preferably from 6 to 15, in particular from 6 to 12, lauric acid being especially preferred as carboxylic acid. As carboxylic acid esters, consideration may be given in particular to the methyl or ethyl esters of the aforementioned carboxylic acids, with the methyl ester of lauric acid being especially preferred as carboxylic acid ester.

In the production of the ω-aminocarboxylic acids, ω-aminocarboxylic acid esters or lactams derived from ω-aminocarboxylic acids, various procedures are conceivable in step I).

According to one embodiment of the method according to the invention, the cells are first cultivated, for the purpose of biomass production, in a nutrient medium that does not contain carboxylic acids or carboxylic acid esters, and in particular does not contain the aforementioned, preferred carboxylic acids or carboxylic acid esters. It is only after a certain biomass has been obtained that the carboxylic acids or the carboxylic acid esters are added to the nutrient medium or the cells are brought into contact with a new nutrient medium containing the carboxylic acids or carboxylic acid esters. In this connection it is in particular preferable for the content of carboxylic acids or carboxylic acid esters during the formation of ω-aminocarboxylic acids, of ω-aminocarboxylic acid esters or of lactams derived from ω-aminocarboxylic acids to be in the range from 1 to 200 g/l, especially preferably in the range from 20 to 200 g/l.

According to another embodiment of the method according to the invention, it is carried out in a two phase system, containing
A) an aqueous phase, and
B) an organic phase,
with the formation of the ω-aminocarboxylic acids, ω-aminocarboxylic acid esters or lactams derived from ω-aminocarboxylic acids by the cells in step I) taking place in the aqueous phase and with the resultant ω-aminocarboxylic acids, the resultant ω-aminocarboxylic acid esters or the resultant lactams derived from ω-aminocarboxylic acids accumulating in the organic phase. In this way it is possible for the resultant ω-aminocarboxylic acids, the resultant ω-aminocarboxylic acid esters or the resultant lactams derived from ω-aminocarboxylic acids to be extracted in situ.

Also in this embodiment of the method according to the invention, it may prove advantageous for the cells first to be cultivated, for the purpose of biomass production, in a nutrient medium that does not contain carboxylic acids or carboxylic acid esters, and in particular does not contain the aforementioned, preferred carboxylic acids or carboxylic acid esters. It is only after a certain biomass has been obtained that the cell suspension as aqueous phase A) is brought into contact with the organic phase B), where in particular the organic phase B) contains the carboxylic acid or the carboxylic acid esters preferably in an amount in the range from 1 to 200 g/l, especially preferably in the range from 20 to 200 g/l. However, if substrates that are not toxic to the cells used, such as methyl laurate, are employed as carboxylic acids or carboxylic acid esters, then the content of these carboxylic acids or carboxylic acid esters in the organic phase can also be significantly higher. In such a case it may also be possible to use the pure carboxylic acid or the pure carboxylic acid esters, for example pure methyl laurate, as organic phase.

As organic phase, it is possible to use alkanes of medium chain length, preferably those with a logP value of more than 4 (little foam formation), or physically similar aromatics or aromatic esters, though preferably, as mentioned above, lauric acid esters, especially preferably methyl laurate, BEHP (bis(2-ethylhexyl)phthalate) or long-chain fatty acid esters (biodiesel).

Furthermore it is preferable according to the invention if, at least during the phase of formation of ω-aminocarboxylic acids, of ω-aminocarboxylic acid esters or of lactams derived from ω-aminocarboxylic acids, the culture medium used in step I) contains amino group donors, such as ammonia or ammonium ions or even amino acids, though in particular alanine or aspartate, which function as amine donors in the transaminase-catalysed conversion of the ω-oxocarboxylic acids or the ω-oxocarboxylic acid esters to the corresponding ω-aminocarboxylic acids or ω-aminocarboxylic acid esters.

In step II) of the method according to the invention, the resultant ω-aminocarboxylic acids, the resultant ω-aminocarboxylic acid esters or the lactams derived from the ω-aminocarboxylic acids are optionally isolated, and it is preferable for this isolation to take place in an at least two-stage purification process, comprising
a) an extraction step, in which the ω-aminocarboxylic acids, the ω-aminocarboxylic acid esters or the lactams derived from ω-aminocarboxylic acids are extracted from the culture medium, and
b) a fine purification step, in which the extract obtained in step a) is purified further by a distillation process or selective crystallization, obtaining an ω-aminocarboxylic acid phase, an ω-aminocarboxylic acid ester phase or a lactam phase with a purity of at least 99.8%.

The extraction in step a) can in particular be designed as so-called "in situ" extraction, in which steps I) and II) of the method according to the invention for the production of ω-aminocarboxylic acids, of ω-aminocarboxylic acid esters or of lactams derived from ω-aminocarboxylic acids are carried out simultaneously. This "in situ" extraction has already been described above.

The fine purification in step II) can for example take place by distillation or crystallization.

In a special embodiment of the method according to the invention for the production of ω-aminocarboxylic acids, of ω-aminocarboxylic acid esters or of lactams derived from ω-aminocarboxylic acids, the ω-aminocarboxylic acid esters formed in step I) are reacted in another process step by conventional chemical methods to ω-aminocarboxylic acids; a preferred, conventional chemical method is saponification, in which the ω-aminocarboxylic acid ester is reacted with an aqueous solution of a base, preferably a hydroxide, preferably sodium hydroxide, to the ω-aminocarboxylic acid.

Preferably this method is used for the production of ω-aminolauric acid from lauric acid esters, preferably methyl laurate;

A contribution to achievement of the aims stated at the beginning is also provided by ω-aminocarboxylic acids, ω-aminocarboxylic acid esters or by lactams derived from ω-aminocarboxylic acids, which are obtainable by the method described above, the lactam preferably being laurinlactam, which is obtained if lauric acid or lauric acid esters are used as carboxylic acid or as carboxylic acid esters in step I) of the method according to the invention for the production of lactams derived from ω-aminocarboxylic acids, wherein the ω-aminocarboxylic acid is preferably ω-aminolauric acid and the ω-aminocarboxylic acid ester is preferably ω-aminomethyl laurate.

A contribution to achievement of the aims stated at the beginning is also provided by a method for the production of polyamides based on ω-aminocarboxylic acids, comprising the process steps:

(α1) production of ω-aminocarboxylic acids by one of the methods described above for the production of ω-aminocarboxylic acids, in particular by the method described above for the production of ω-aminolauric acid from lauric acid or lauric acid esters;

(α2) polymerization of the ω-aminocarboxylic acid, obtaining a polyamide.

In step (α2) of the method according to the invention for the production of polyamides based on ω-aminocarboxylic acids, the ω-aminocarboxylic acids obtained in step (α1), in particular the ω-aminolauric acids obtained in step (α1), are converted in a polymerization to a polyamide, and optionally mixtures of various ω-aminocarboxylic acids can also be used, for which at least one of the ω-aminocarboxylic acids, but optionally all ω-aminocarboxylic acids were produced by the method according to the invention for the production of ω-aminocarboxylic acids.

The production of the polyamides from the ω-aminocarboxylic acids can can be carried out by well-known methods, as described for example in L. Notarbartolo, Ind. Plast. Mod. 10 (1958)2, p. 44, JP 01-074224, JP 01-051433, JP63286428, JP58080324 or JP60179425.

A contribution to achievement of the aims stated at the beginning is also provided by a method for the production of polyamides based on lactams, comprising the process steps:

(β1) production of lactams by the method described above for the production of lactams derived from ω-aminocarboxylic acids, in particular by the method described above for the production of laurinlactam from lauric acid or lauric acid esters;

(β2) ring opening polymerization or polycondensation of the laurinlactam, obtaining a polyamide.

In step (β2) of the method according to the invention for the production of polyamides based on lactams, the lactams obtained in step (β1), in particular the laurinlactam obtained in step (β1), are converted in a ring opening polymerization or by polycondensation to a polyamide, and optionally it is also possible to use mixtures of various lactams, for example mixtures of laurinlactam and ε-caprolactam, for which at least one of the lactams, but optionally all lactams were produced by the method according to the invention for the production of lactams derived from ω-aminocarboxylic acids.

The production of the polyamides from the lactams can be carried out by well-known methods, as described for example in DE-A-14 95 198, DE-A-25 58 480, EP-A-0 129 196 or also in "*Polymerization Processes*", Interscience, New York, 1977, pages 424-467, especially pages 444-446.

A contribution to achievement of the aims stated at the beginning is also provided by polyamides, which are obtainable by the methods described above. It is especially preferable for these polyamides to be based, up to at least 10 wt. %, especially preferably up to at least 25 wt. %, still more preferably up to at least 50 wt. % and most preferably up to at least 75 wt. %, on lauric acid, lauric acid ester or laurinlactam, obtained by the method according to the invention for the production of lauric acid, of lauric acid ester or of laurinlactam from lauric acid or lauric acid esters.

The invention will now be explained with the aid of non-limiting diagrams and examples.

Figure 4:
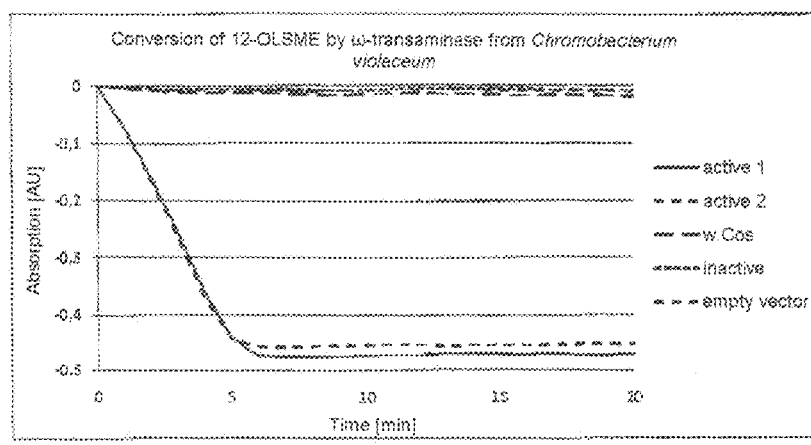

FIG. 4 shows determination of the activity of *C. violaceum*-transaminase from the enzyme assay. The activity was determined in duplicate (active1, active2) with a photometer. A batch without the ω-substrate L-alanine (w.Cos), a batch with heat-inactivated enzyme (inactive) and a batch from *E. coli* expression culture with empty vector (empty vector), purified similarly to the omega-TA, were used as negative controls.

FIG. 5 shows chromatograms of the substrate 12-aminomethyl laurate at the start of reference measurement (top) and after 2 h incubation with the purified transaminase (bottom).

Figure 6:
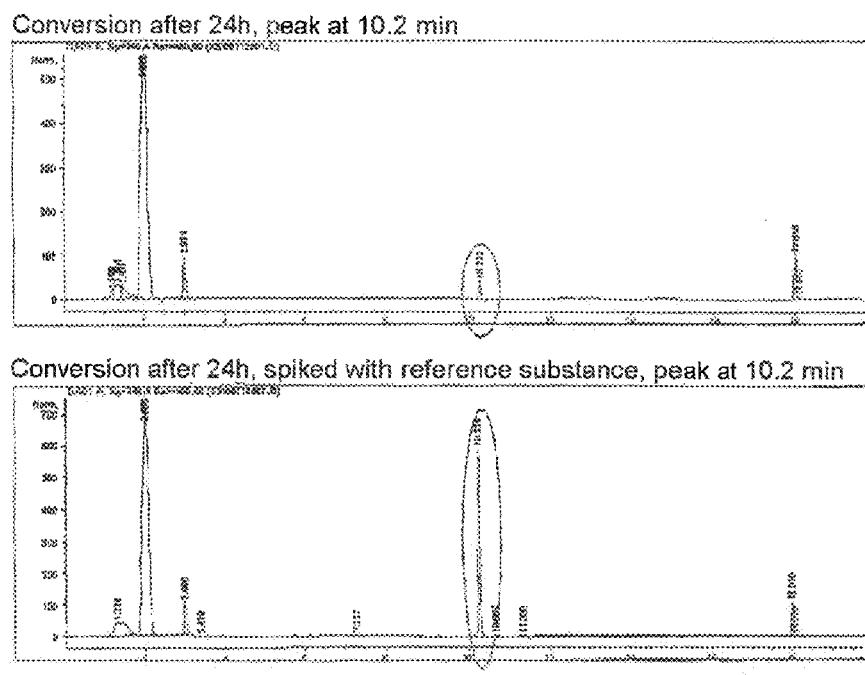

FIG. 6 shows chromatograms of the substrate 12-aminomethyl laurate after 24 h (top) of the enzyme assay and after spiking the substrate (control, bottom).

Figure 7:
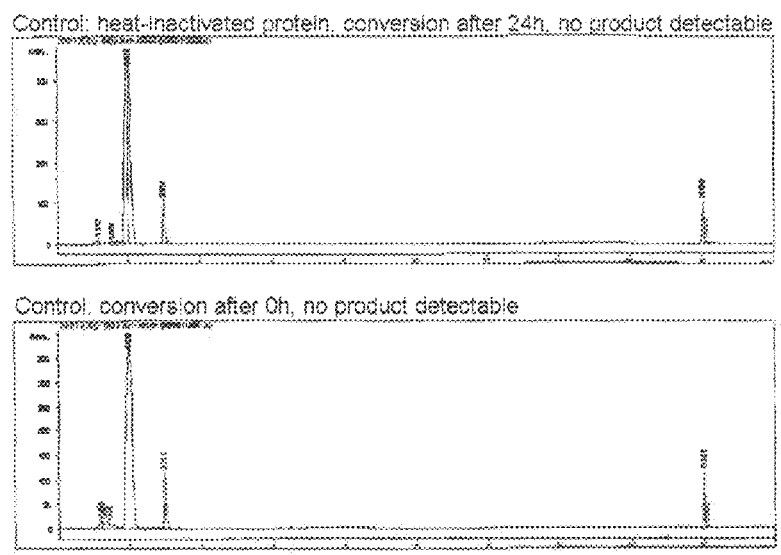

FIG. 7 shows 6 chromatograms of the substrate 12-aminomethyl laurate after heat inactivation of the enzyme (top) and after 0h (bottom).

Figure 8:
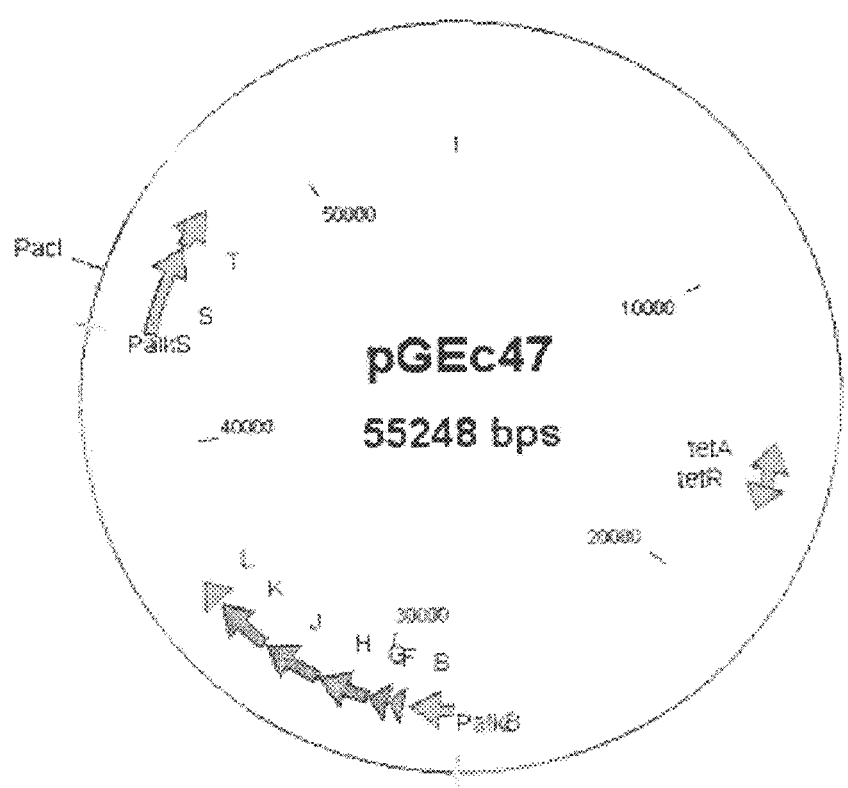

FIG. 8 shows the starting plasmid pGEc47, which was used as template for the amplification of alkBGTS.

Figure 9:
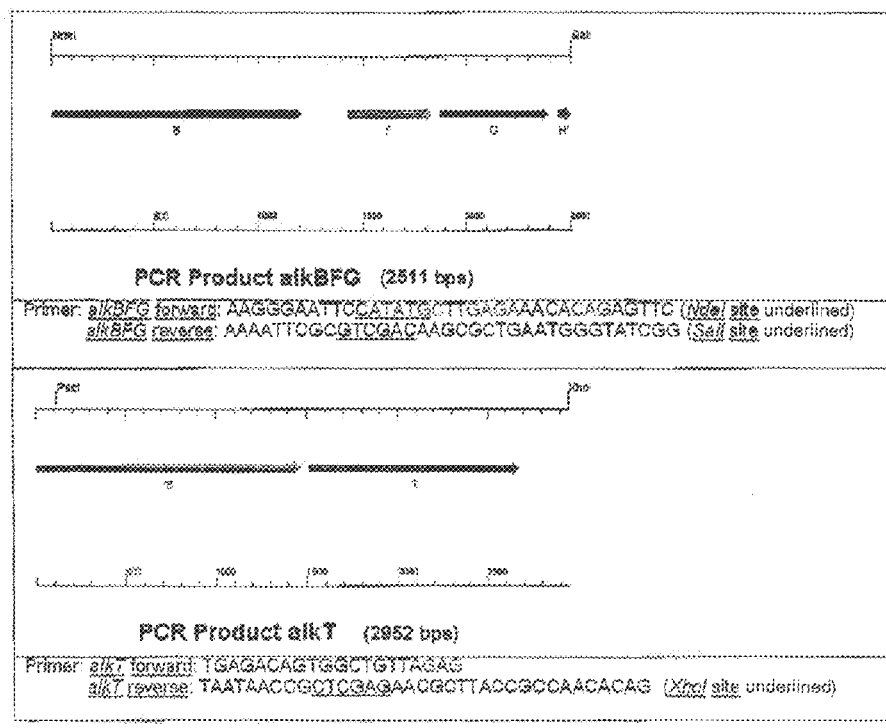

FIG. 9 shows the primers (SEQ ID NOS: 32-35, respectively, in order of appearance) used and the resultant PCR products alkBFG and alkT.

Figure 10:
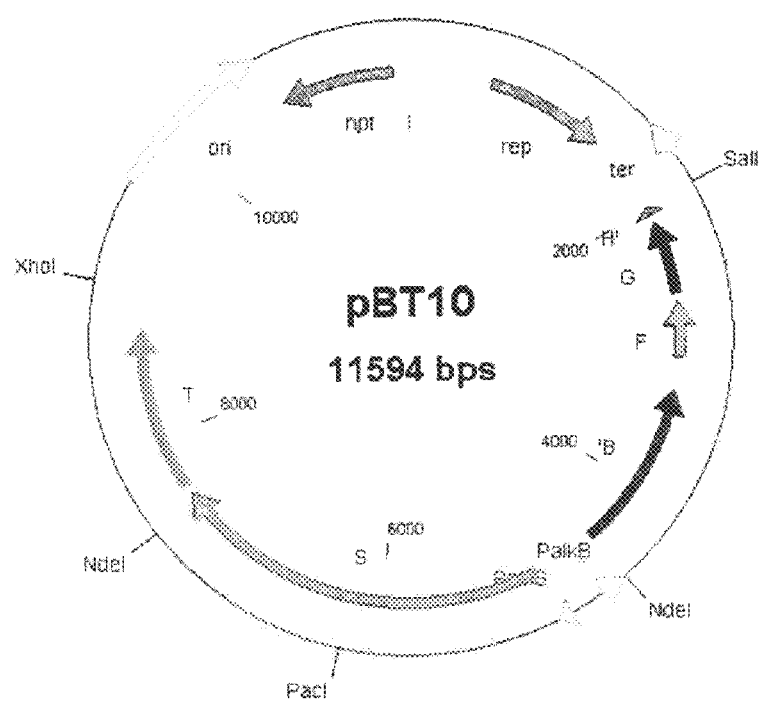

FIG. 10 shows the recombinant vector pBT10, which was used for the synthesis of hydroxymethyl laurate and oxomethyl laurate.

Figure 11:
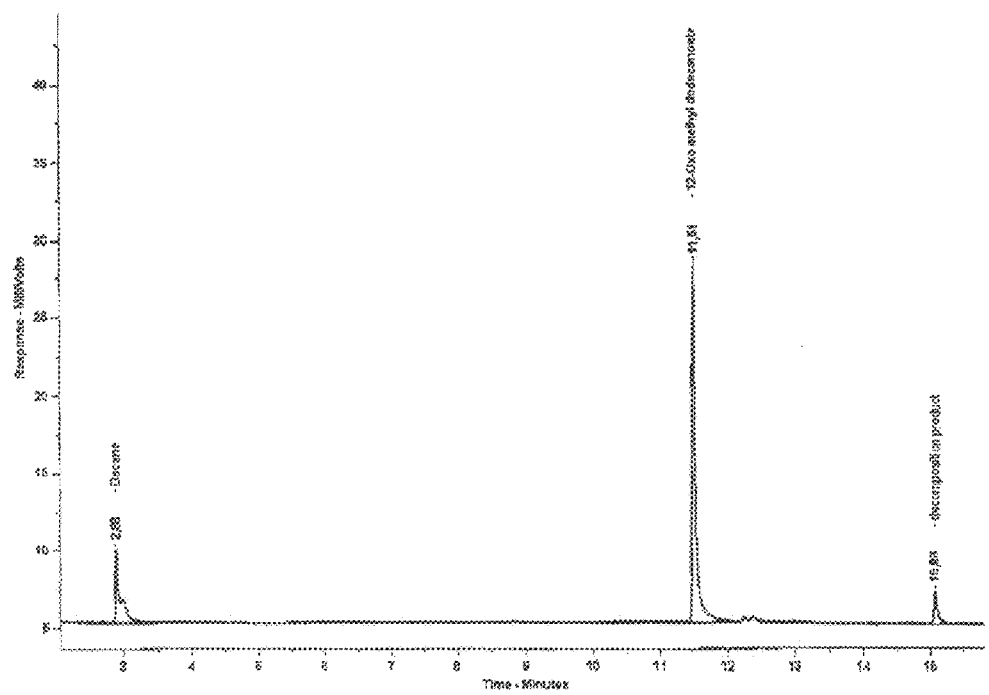

FIG. 11 shows a GC chromatogram of the 12-oxo-methyl laurate standard.

Figure 12:
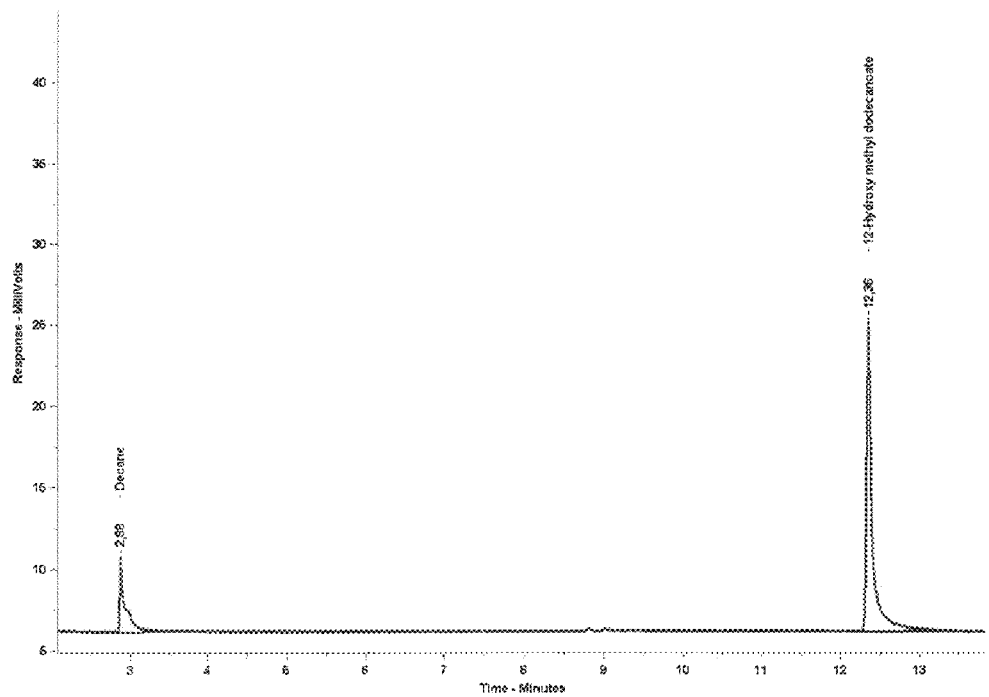

FIG. 12 shows a GC chromatogram of the 12-hydroxymethyl laurate standard.

Figure 13:
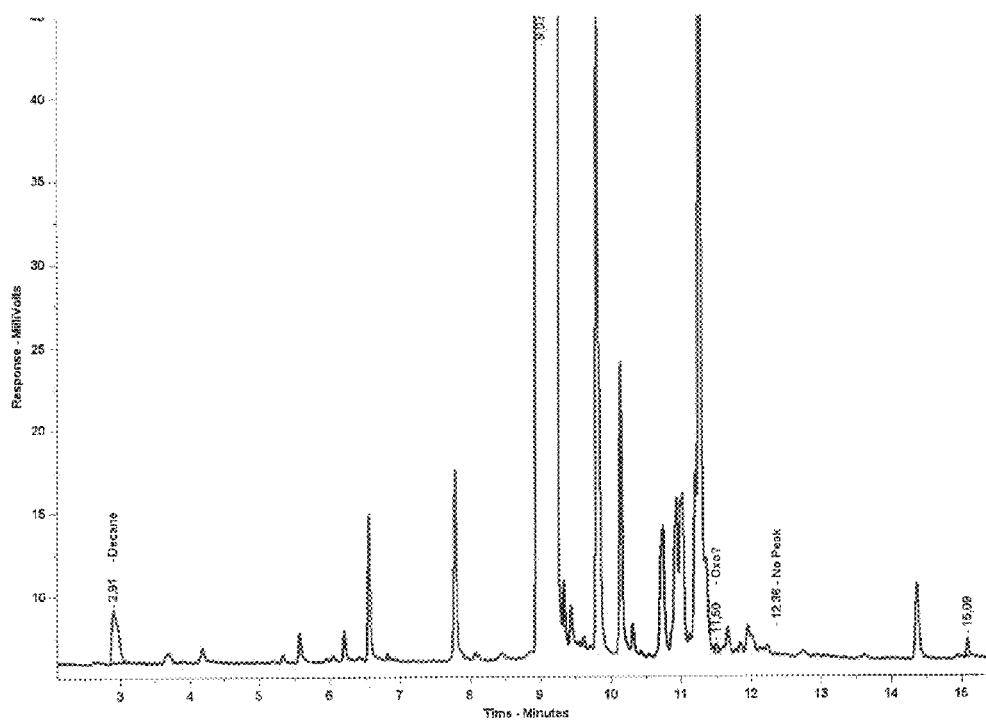

FIG. 13 shows a chromatogram of the organic phase from a resting cell biotransformation in the bioreactor of methyl laurate, at time 0 min.

Figure 14:
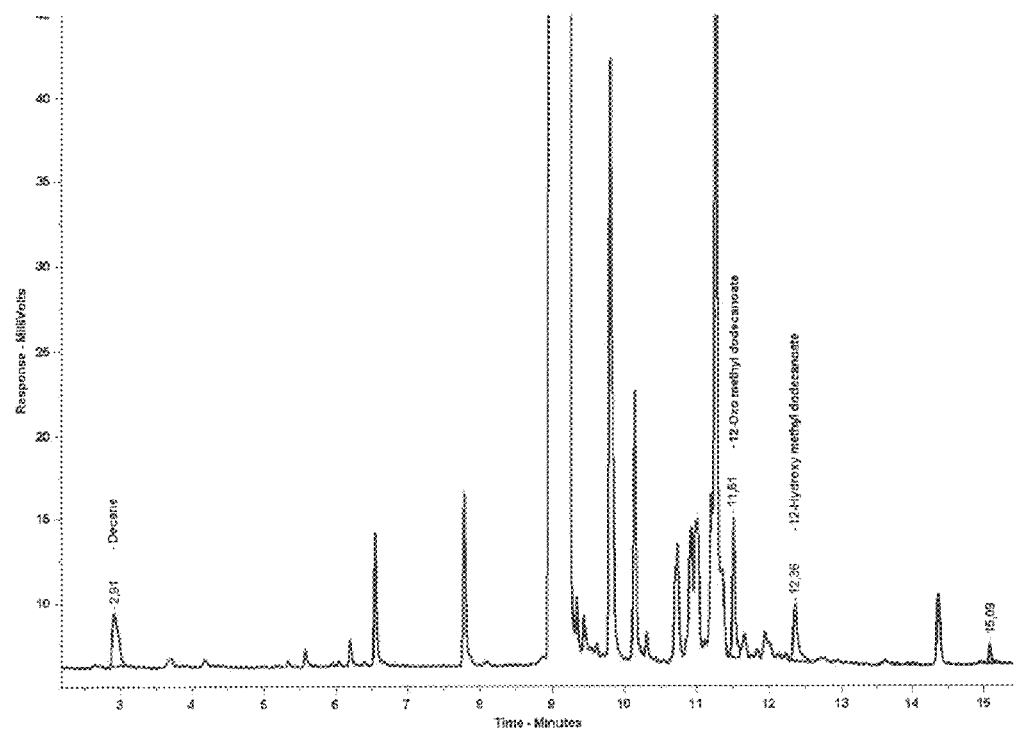
Figure 1S:
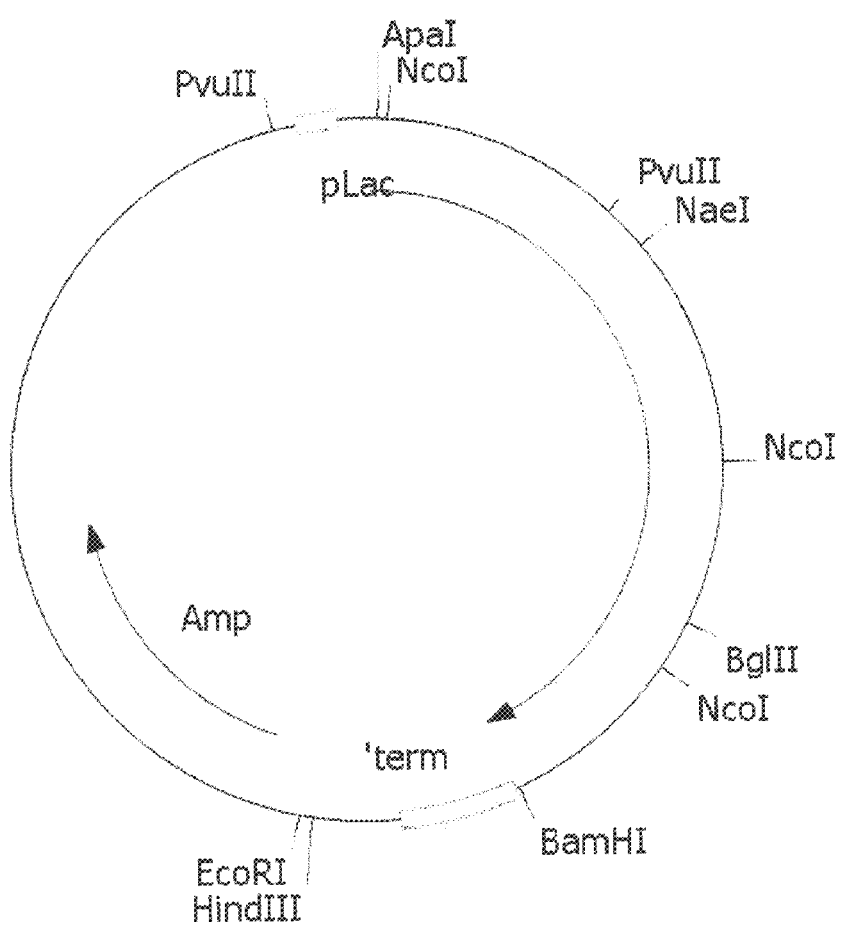

FIG. 14 shows a chromatogram of the organic phase from a resting cell biotransformation in the bioreactor of methyl laurate, at time 150 min.

FIG. 15 shows the expression vector pGJ3130 with AT3G22200.

Figure 16:
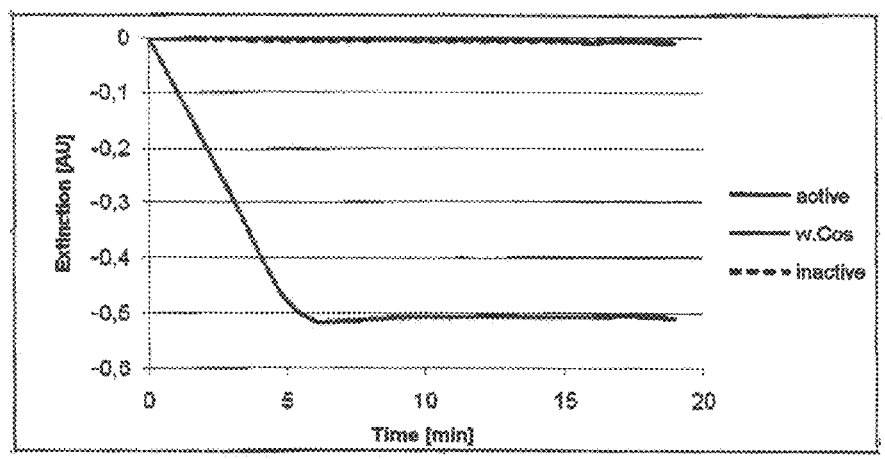

FIG. 16 shows detection of enzyme activity by coupled enzyme assay (inactive, heat-inactivated protein; w.Cos., without addition of alanine; akt, the purified, active enzyme).

Figure 17:
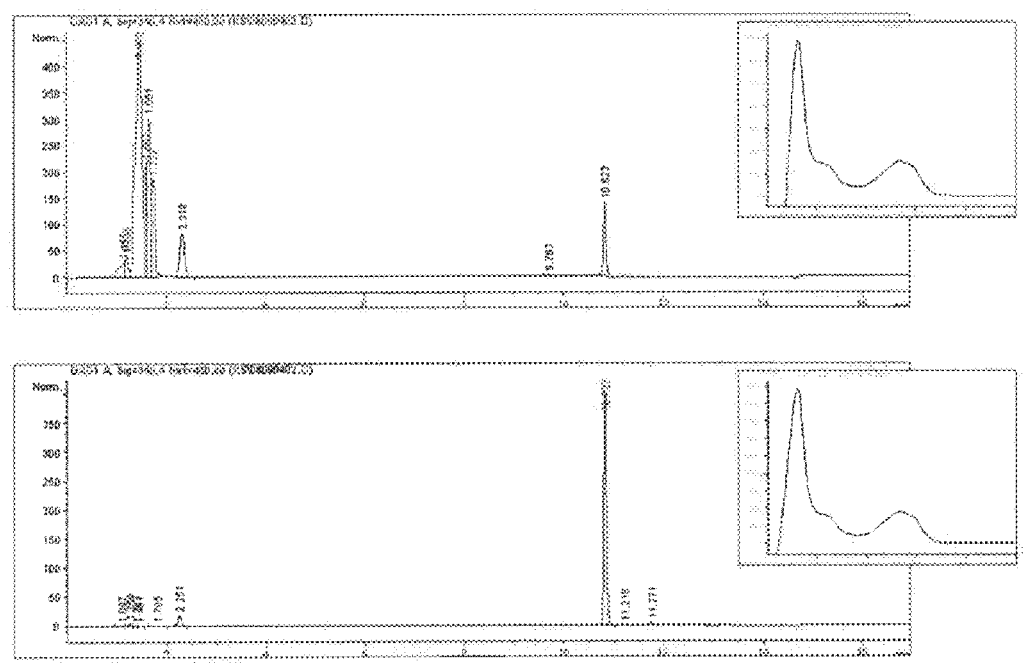

FIG. 17 shows detection of the heterologously expressed protein AT3G22200 by HPLC. Top: product after 20 min incubation at 10.8 min; bottom: reference substance at 10.8 min.

Figure 18:
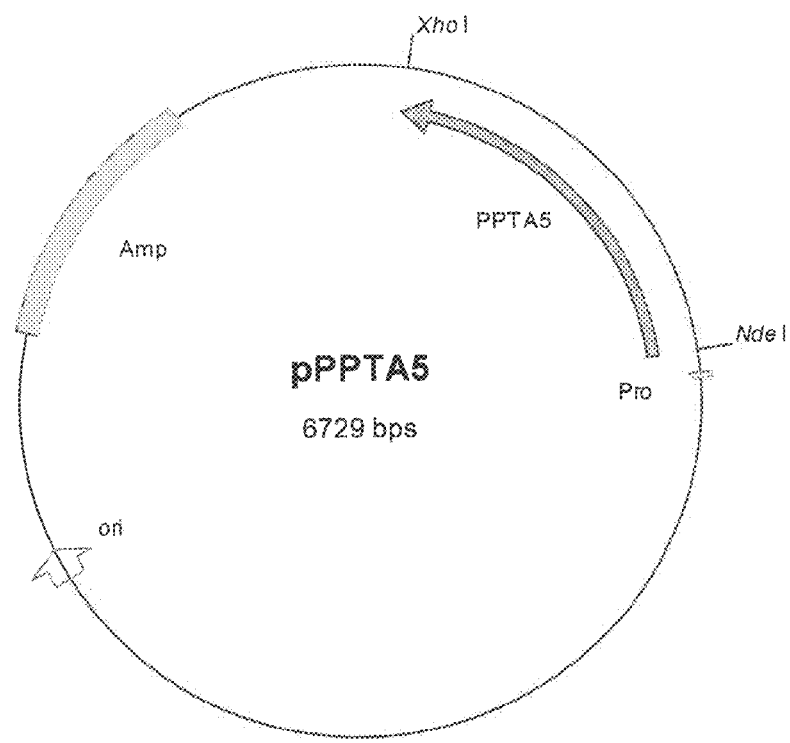

FIG. 18 shows the plasmid map of the expression vector pET-21a(+) with the transaminase gene ppta5 (pPPTA5).

Figure 19:
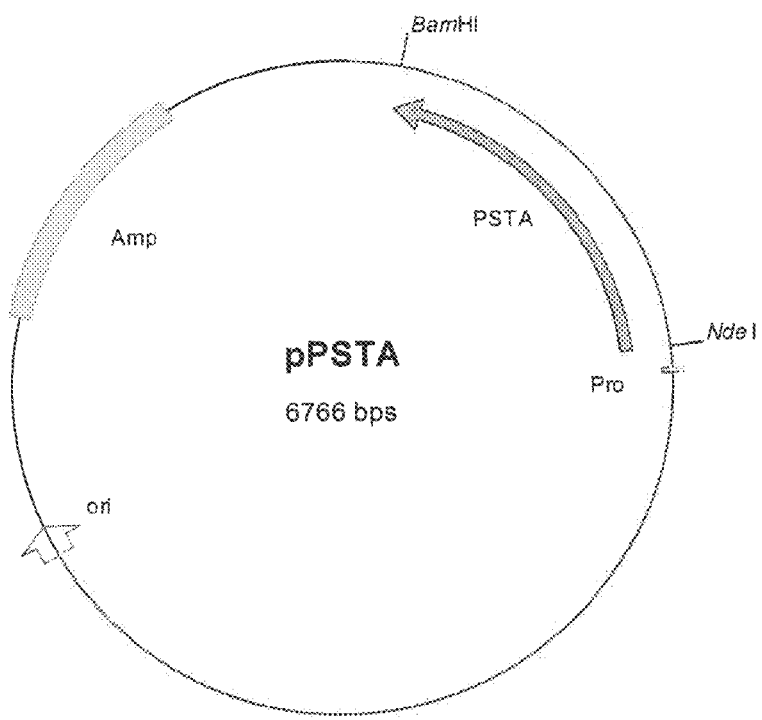

FIG. 19 shows the plasmid map of the expression vectors pET-21a(+) with the transaminase gene psta (pPSTA).

Figure 20:
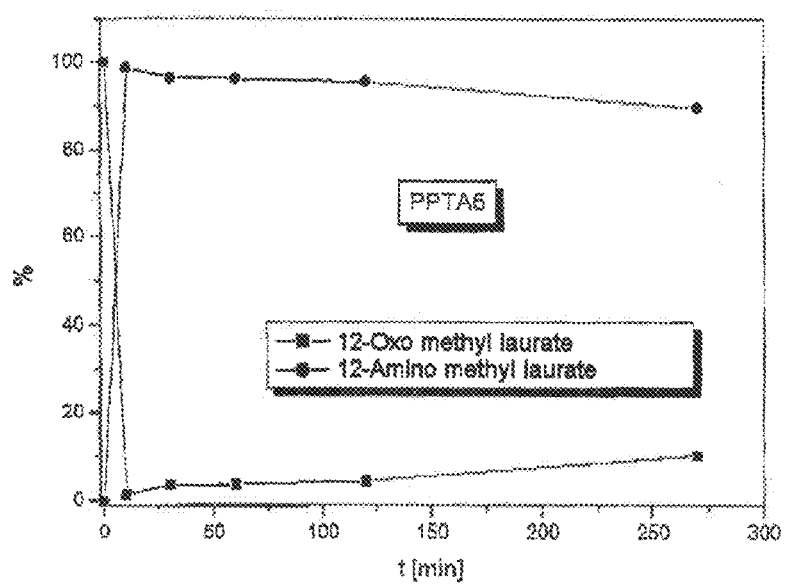

FIG. 20 shows the amination of 5 mM 12-oxomethyl laurate with the transaminases PPTA5. For the evaluation, the peak areas of 12-oxo- and 12-aminomethyl laurate from the chromatograms obtained from neutral and acid extraction were added together and the percentage of educt or product was calculated.

Figure 21:
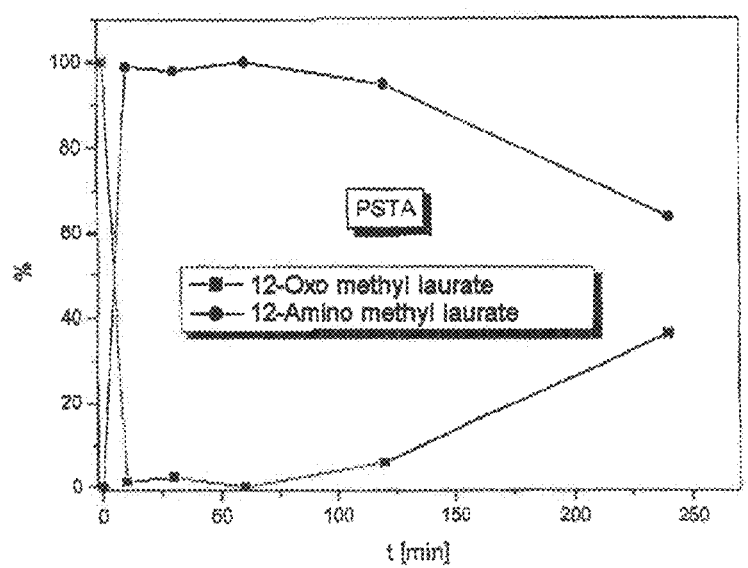

FIG. 21 shows the amination of 5 mM 12-oxomethyl laurate with the transaminases PSTA. For the evaluation, the peak areas of 12-oxo- and 12-aminomethyl laurate from the chromatograms obtained from neutral and acid extraction were added together and the percentage of educt or product was calculated.

EXAMPLES

A. Conversion of Lauric Acid or Methyl Laurate to Laurinlactam

For the conversion of lauric acid or of methyl laurate to laurinlactam, *E. coli* is supplemented with the necessary enzymes monooxygenase, alcohol dehydrogenase, ω-transaminase, alanine dehydrogenase and a lipase. The enzymes are overexpressed in *E. coli*; the expression levels of the individual enzymes are dependent on the kinetics of the individual reactions and require optimum adjustment to one another. The expression level is adjusted by adding the appropriate amount of inductor. The expression of monooxygenase and of alcohol dehydrogenase is induced with n-octane; transaminase and alanine dehydrogenase are induced with arabinose and the lipase with IPTG.

A1. Cloning of the Individual Enzymes

Hydroxylation and aldehyde Formation

The alkane hydroxylase system alkBGT from *Pseudomonas putida* GPo1 is used for the hydroxylation of lauric acid or of methyl laurate. The second step to the aldehyde is catalysed by the alcohol dehydrogenase alkJ.

The genes alkBGJT necessary for these reactions are integrated in *E. coli* by insertion into the mini-transposon Tn5 chromosomally into the genome of *E. coli* (de Lorenzo et al., *J. Bacteriol.*, Vol. 172 (11), pages 6568-6572 and 6557-6567 (1990); Panke et al., *Appl and Environm. Microbiol.*, pages 5619-5623 (1999)). The genes are to be expressed under the control of the alkB promoter and of the positive regulator alkS. Transfer of the Tn5-alkBGFJST construct to the *E. coli* target organism is effected with the aid of the mobilizable plasmid pUT-Km (Panke et al., 1999, see above).

The alkST locus with the expression-relevant regulator alkS is organized outside of the alkBFGHJKL operon and arranged in the opposite direction in the genome of *Pseudomonas putida*. The arrangement of the genes is preserved during cloning into the transposon-bearing plasmid. The fragments alkST and alkBFGJ are integrated into the plasmid one after another.

The genes to be cloned alkB (SEQ ID No. 03), alkG (SEQ ID No. 04) and alkJ (SEQ ID No. 05) are indeed organized in *P. putida* together in the operon alkBFGHJKL, but are separated by the gene alkH, which encodes an aldehyde dehydrogenase. The desired intermediate, the aldehyde of lauric acid, would be broken down again by this enzyme and the latter must therefore be excluded from the cloning of the alkBaI genes.

To simplify the cloning of alkB and alkG, the gene alkF located between them is amplified and cloned together with alkB and alkG. A1kF is of no significance for the reaction that is to be catalysed. The genes alkBFG and alkJ are amplified in two separate PCR steps and fused together by SOE-PCR (Horton et al., *Gene*, Vol. 77, pages 61-68 (1989)). The OCT plasmid from *Pseudomonas putida* GPo1 serves as target DNA.

A2. Cloning Strategy:

PCR amplification of the fragments alkST=4077 by (SEQ ID No. 06 (alkS) and SEQ ID No. 07 (alkT)) with NotI cleavage site upstream of alkT:

```
Primers
alkT-forward-NotI
                                       (SEQ ID No. 08)
  5' ACGTAGCGGCCGCCTAATCAGGTAATTTTATAC alkS-reverse
                                       (SEQ ID No. 09)
  5' GAGCGAGCTATCTGGT
```

The PCR fragment is cloned into the transposon-bearing vector pUT-Km. For this, the vector is cut within Tn5 with NotI and ligated with the alkST fragment by blunt end ligation. The recombinant plasmid is designated pUT-Km-alkST.

A3. Synthesis of alkBFGJ Constructs by the SOE-PCR Technique:

Synthesis of fragment 1: alkBFG+promoter upstream alkB and NotI cleavage site at the 5'-end (product size: 1409 bp):

```
Primers
alkBFG-forward-NotI
                                       (SEQ ID No. 10)
  5' TCGTAGCGGCCGCCCAGCAGACGACGGAGCAA alkBFG-reverse-SOE
                                       (SEQ ID No. 11)
  5' ATTTTATCTTCTCGAGGCTTTTCCTCGTAGAGCACAT
```

Synthesis of fragment 3, alkJ with complementary end to alkG at the 5'-end and NotI cleavage site at the 3'-end (product size: 1723 bp):

```
Primers
alkJ-forward-SOE
                                       (SEQ ID No. 12)
  5' TGCTCTAACGAGGAAAAGCCTCGAGAAGATAAAATGTA alkJ-reverse-NotI
                                       (SEQ ID No. 13)
  5' ATTGACGCGGCCGCTTACATGCAGACAGCTATCA
```

Figure 1:
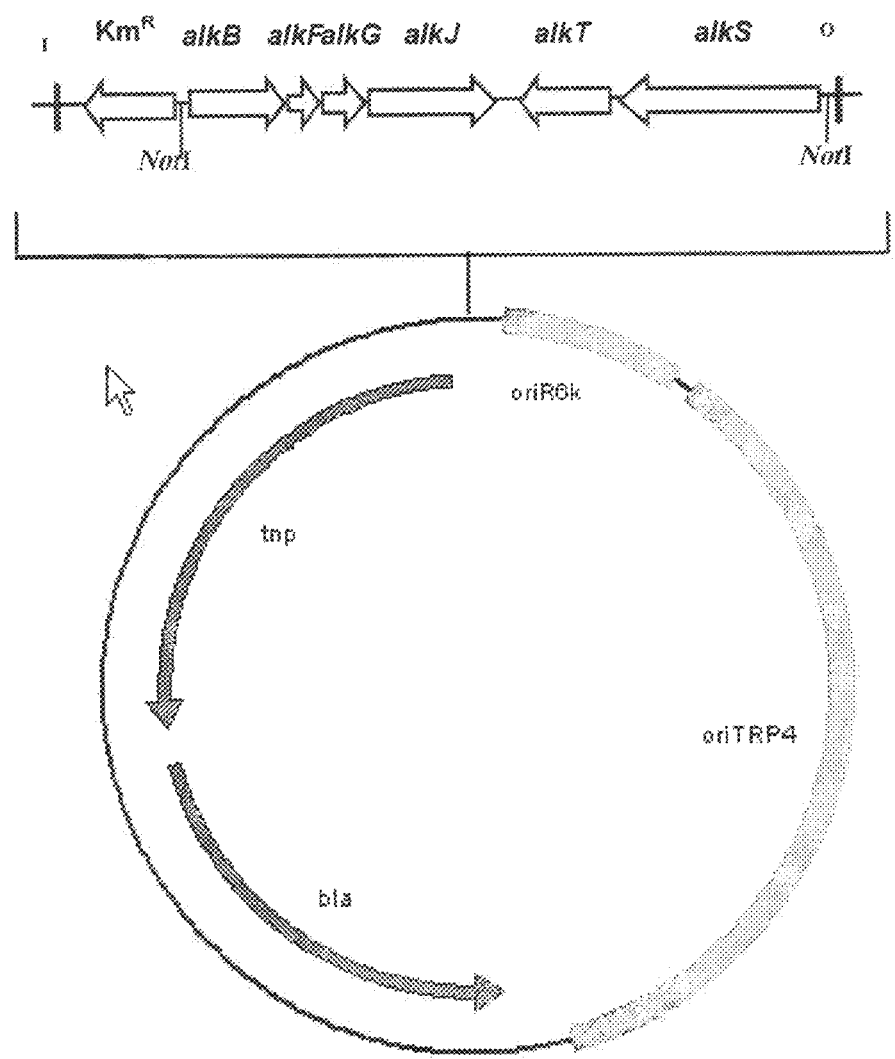
FIG. 1 shows, schematically, a recombinant plasmid for chromosomal integration of the alk genes in *Escherichia coli* (tnp: transposase gene; bla: ampicillin resistance gene; oriT RP4: mobilization region; I and O mark the "inverted repeats" of the mini-transposon Tn5).

The two separate fragments are fused together by SOE-PCR. (3 separate PCR reactions required). The recombinant plasmid pUT-Km-alkST and the alkBFGJ construct are cut with NotI and ligated. The new recombinant plasmid pUT-Km-alkBGJST (see FIG. 1) is transformed in *E. coli* HB101 and transferred to *E. coli* JM101 by conjugative plasmid transfer.

A4. Amination and Amino Donor Regeneration

For amination to the ω-aminolauric acid ester and regeneration of the amino donor, the Tn5:alkBGJST-bearing *E. coli* strain JM101 is additionally transformed with the recombinant plasmid pBAD-CV2025-aid. This plasmid is based on the pBAD30 vector (Guzman et al., "*Tight Regulation, Modulation, and High-Level Expression by Vectors Containing the Arabinose $P_{BAD}$ Promoter*", *J. Bacteriol*, Vol. 177 (14), pages 4121-4130 (1995)). pBAD-CV2025-ald carries the gene for the transaminase CV2025 from *Chromobacterium violaceum* DSM30191 (SEQ ID No. 01; Kaulmann et al., *Enzyme and Microbial Technology* Vol. 41, pages 628-637 (2007) and the gene ald, which codes for an alanine dehydrogenase from *Bacillus subtilis* subsp. *Subtilis* (SEQ ID No. 02; NP_391071). The genes are under the control of an arabinose inducible promoter.

A5. Cloning Strategy

PCR amplification of the transaminase gene with chromosomal DNA from *Chromobacterium violaceum* DSM30191 (product size: 1415 bp):

```
Primers
CV2025-forward-SacII
                                        (SEQ ID No. 14)
5' CGAGGAGCTCAGGAGGATCCAAGCATGCAGAAGCAACGTACG CV2025-reverse-KpnI
                                        (SEQ ID No. 15)
5' GTCATGTACCCCTAAGCCAGCCCGCGCGCCT
```

For the cloning into the pBAD30 vector, the forward-primer contains a ribosome binding site in addition to the XbaI cleavage site. Ligation into the pBAD30 vector takes place via the cleavage sites SacI and KpnI. The recombinant vector is designated pBAD-CV2025.

PCR amplification of the alanine dehydrogenase gene ald with chromosomal DNA from *B. subtilis* subsp. *Subtilis* (NP_391071) (product size: 1171 bp).

```
Primers
AlaDH-forward-XbaI
                                        (SEQ ID No. 16)
5' ACCTATCTAGAAGGAGGACGCATATGATCATAGGGGTTCCT AlaDH-reverse-PstI
                                        (SEQ ID No. 17)
5' AACCTCTGCAGTTAAGCACCCGCCAC
```

Figure 2:
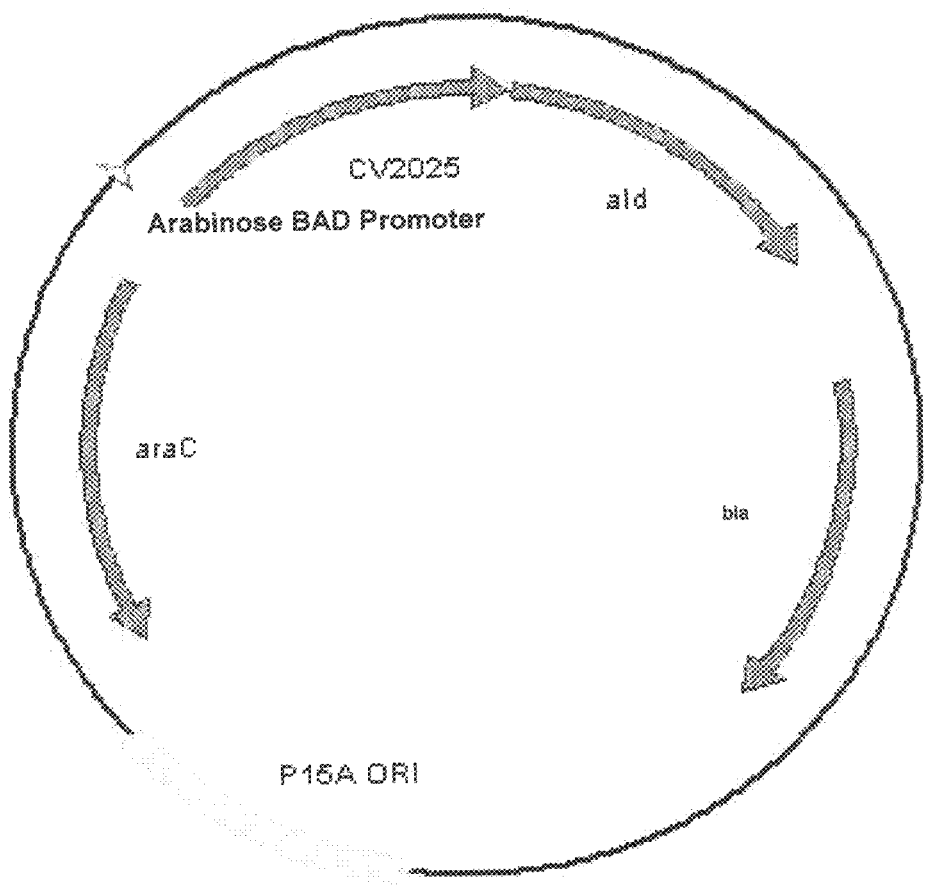
FIG. 2 shows, schematically, a recombinant plasmid for expression of transaminase and of alanine dehydrogenase under the control of an arabinose inducible promoter (bla: ampicillin resistance gene; CV2025: gene for ω-transaminase from *Chromobacterium violaceum*; ald: gene for alanine dehydrogenase from *B. subtilis*; araC: transcription regulator).

For the cloning into the recombinant vector pBAD-CV2025, the forward-primer contains a ribosome binding site in addition to the XbaI cleavage site. The cloning into the vector takes place via the cleavage sites XbaI and PstI. The resultant plasmid is designated pBAD-CV2025-ald (see FIG. 2).

A6. Alternative Cloning of the Omega-Transaminase Gene from *Chromobacterium violaceum* DSM 30191 for Codon-Optimized Expression in *E. coli*

The gene coding for omega-transaminase was synthesized by the company Geneart, optimized for *E. coli* codon usage (SEQ ID No. 42) and cloned into the vector pGA15 (Geneart). During synthesis of the gene, the cleavage sites SacI and KpnI were incorporated in flanking positions and, after digestion with SacI and KpnI, were cloned into the vector pGA15, linearized beforehand with SacI and KpnI. The resultant vector was digested with the restriction endonucleases SacI and KpnI, the fragment (transaminase) was purified and was ligated into the expression vector paCYCDuet-1 (Novagen). The correct plasmids were verified by restriction analysis. The resultant vector is called paCYCDuet-1::omega tranaminase.

A7. Purification of Heterologously Expressed Protein by Means of 6xHis-Tag (SEQ ID NO: 50)

After transformation of the vector (paCYCDuet-1::omega transaminase) in *E. coli* XL1blue, the transformed strain was cultivated in double YT-medium (dYT) with the antibiotic ampicillin (100 µg/ml) at 28° C. up to a density of OD600 nm=0.3–0.4. Expression takes place under the control of the $P_{lac}$ promoter and is induced with IPTG (final concentration 1 mM). Lysis of the bacterial expression culture: 50 ml of culture was centrifuged at 2360 x g, and then resuspended in 5 ml Na-phosphate buffer (pH 8) with 5 mM EDTA, 300 mM NaCl and 1 mg/ml lysozyme, and incubated for 1 h at RT. The lysate was centrifuged at 2360 x g for 10 min and the supernatant was purified on a Protino Ni-TED 2000 packed column (following the instructions of the manufacturer; Macherey-Nagel, Düren). The protein concentration was determined according to Bradford.

A8. Detection of Enzyme Activity by Coupled Assay

The activity was determined in a coupled assay, in which the pyruvate formed as by-product of the transaminase reaction is reacted further in a second step, and NADH is oxidized to NAD+. The decrease in NADH concentration (principle: measurement of the decrease in extinction) is measured in the photometer at 340 nm and provides a measure of the activity.

| Preparation | |
|---|---|
| 50 mM | Na-phosphate pH 7.5 |
| 50 mM | L-alanine |
| 100 µM | Pyridoxal phosphate |
| 250 µg | 12-oxomethyl dodecanoate |
| 1.25 mM | NADH |
| 10 U | Lactate dehydrogenase |
| 10 µg | heterologously expressed protein |

Make up to 1 ml with doubly distilled water

The assay was started by adding 5 µl 12-ODME (50 mg/ml). Measurement is performed continuously every minute at 340 nm at RT up to max. 20 minutes.

Inactivated protein and a preparation without ω-substrate were used for control.

FIG. 4 shows the variation in extinction, determined photometrically.

A9. Detection of the Heterologously Expressed Protein by HPLC

| Preparation | |
|---|---|
| 50 mM | Na-phosphate pH 7.5 |
| 50 mM | L-alanine |
| 100 µM | Pyridoxal phosphate |
| 250 µg | 12-oxomethyl dodecanoate |
| 50 µg | heterologously expressed protein |

Make up to 500 µl with doubly distilled water

After incubation for 4 h at RT, the reaction was stopped with 1 Vol. MeOH. For HPLC analysis, the preparation was derivatized with o-phthalic aldehyde (oPA) and 250 µl thereof was analysed. 50 mM NaAC pH 4:acetonitrile 4:1 (v:v) was used as solvent A.

Solvent B was acetonitrile with 5% 50 mM NaAC pH 4. The gradient was from 30% B to 60% B in 4 min, from 60% B to 100% B in 2 min. The flow rate was 1.2 ml/min. Separation took place in an Agilent Zorbax RP18 column (Agilent Technologies, USA), the column temperature was 40° C.

FIGS. 5 and 6 show the standard and the decrease of the 12-oxomethyl laurate. Heat-inactivated enzyme was used as negative control (FIG. 7).

A6. Ester Cleavage

Figure 3:
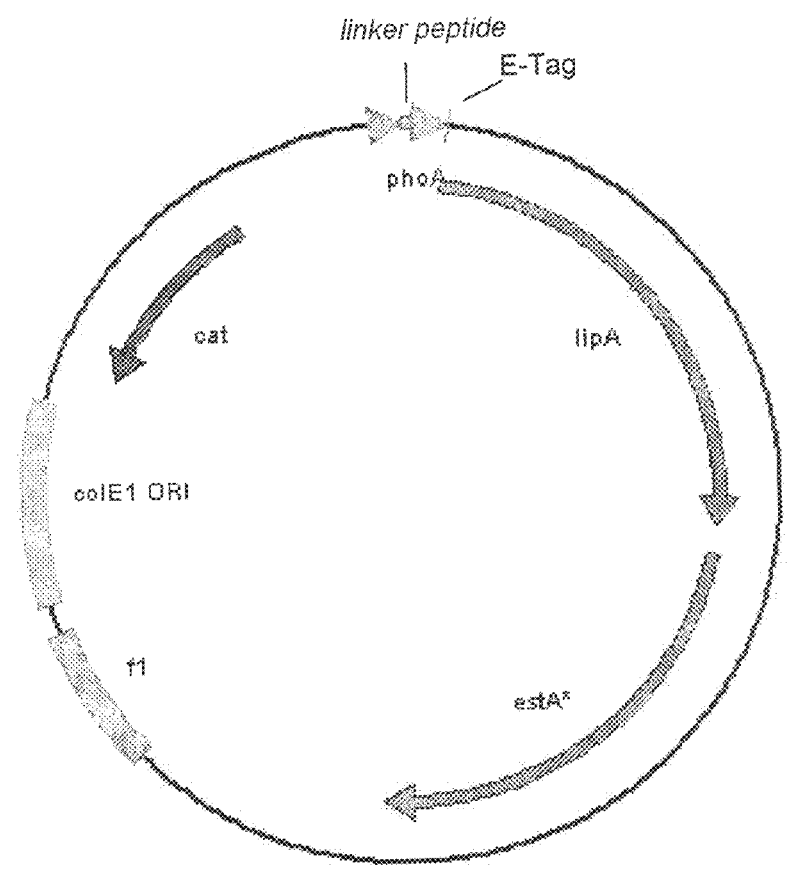
FIG. 3 shows, schematically, a recombinant plasmid for the expression of LipA in *E. coli* and presentation of the enzyme on the cell surface (colE1, ColE1: replication origin; estA*, estA: gene with amino acid exchange alanine for serine (codon #38), cat: chloramphenicol resistance gene; phoA: gene segment that encodes the leader sequence of alkaline phosphatase).

The lipase LipA (Q76D26) from *Pseudomonas fluorescens* (Kojima & Shimizu, *J. of Bioscience and Bioengin.*, Vol. 96 (3), pages 219-226 (2003)) is used for the cleavage of ω-aminomethyl laurate to ω-aminolauric acid. The gene is amplified with the primers LipA-SfiI-up and LipA-SfiI-down with chromosomal DNA from *Pseudomonas fluorescens* and cloned via the SfiI cleavage sites into the vector pEST100. The recombinant plasmid is designated pEST-lipA (see FIG. 3).

The cloning fuses lipA (SEQ ID No. 18) to the signal sequence of alkaline phosphatase phoA and the autotransporter domain of EstA, an esterase from *P. aeruginosa*, so that the lipase is transferred across the cytoplasmic membrane and is displayed on the cell surface of *E. coli*. For the procedure see Becker et al., "*A generic system for the Escherichia coli cell-surface display of lipolytic enzymes*", *FEBS Letters* Vol. 579, pages 1177-1182 (2005). Expression takes place under the control of the $P_{lac}$ promoter and is induced with IPTG (final concentration 1 mM) (product size: 1894 bp).

Primers
Primer lipA-Sfi-up
(SEQ ID No. 48)
5' AACAAAAGGGCCGCAATGGCCATGGGTGTGTATGACTAC Primer lipA-Sfi-down
(SEQ ID No. 49)
5' TACAGGGGCCACCACGGCCTCAGGCGATCACAATTCC B Synthesis of 12-Hydroxymethyl Laurate and 12-Oxomethyl Laurate Starting from Methyl Laurate with the AlkBGT Alkane Hydroxylase System from *Pseudomonas putida* Gpo1

B1. Construction of the alkBGT Expression vectors

The construct pBT10 (FIG. 10, SEQ ID No. 31), which contains the three components alkane hydroxylase (AlkB), rubredoxin (AlkG) and rubredoxin reductase (AlkT) from *Pseudomonas putida* that are necessary for the oxidation to the aldehyde, was produced starting from the pCOM systems (Smits et al., 2001 Plasmid 64:16-24). For expression of the three genes, the alkBFG gene sequence was put under the control of the alkB-promoter and the alkT gene under the control of the alkS-promoter.

B2. Cloning Strategy:

To simplify the cloning of alkB and alkG, the gene alkF located between them was amplified and cloned together with alkB and alkG. AlkF is of no significance for the reaction that is to be catalysed.

PCR amplification of the fragment alkBFG=2524 by (cf. SEQ ID No. 03 (alkB) and SEQ ID No. 04 (alkG)) with NdeI cleavage site upstream of alkB and SalI cleavage site downstream of alkG:

Primer: alkBFG forward
(SEQ ID No. 32)
AAGGGAATTCCATATGCTTGAGAAACACAGAGTTC

Primer: alkBFG reverse
(SEQ ID No. 33)
AAAATTCGCGTCGACAAGCGCTGAATGGGTATCGG

PCR amplification of the fragment alkT (2958 bp) (cf. SEQ ID No. 07 (alkT))

Primer alkT forward
(SEQ ID No. 34)
TGAGACAGTGGCTGTTAGAG

Primer alkT reverse
(SEQ ID No. 35)
TAATAACCGCTCGAGAACGCTTACCGCCAACACAG

The fragments alkBFG and alkT were amplified by PCR. The plasmid pGEc47 (FIG. 12) (Eggink et al. (1987) J. Biol. Chem. 262, 17712-17718) was used as template.

The clonings were carried out by means of the subcloning vector pSMART® HCKan (Lucigen Corporation). This additional step was necessary because direct cloning had not been successful. For this, the commercially available vector pSMART® HCKan (Lucigen), which was already linearized and provided with blunt ends, was ligated with the respective blunt-end PCR product (FIG. 9).

Next, the alkBFG fragment with the restriction enzymes NdeI and SalI and the alkT fragment with the restriction enzymes PacI and XhoI were cut out of the subcloning vectors. The fragments were separated in agarose gel (1%), cut out of the gel and isolated using a gel extraction kit.

The fragments were ligated one after another into the vector pCOM10 (Smits, T. H. M., Seeger, M. A., Witholt, B. & van Beilen, J. B. (2001) Plasmid 46, 16-24). In the first step alkBFG was inserted in pCOM10 via the cleavage sites NdeI and SalI, and in a second step alkT was then cloned via the cleavage sites PacI and XhoI.

The recombinant plasmid was first transformed in *E. coli* DH5α. Plasmid-bearing clones were selected on kanamycin-containing LB medium. The isolated plasmid was checked by restriction analysis and sequencing. It is designated pBT10 (FIG. 10).

B3. Biotransformation in the Bioreactor of Methyl Laurate to Hydroxymethyl Laurate and 12-Oxomethyl Laurate For the biotransformation, the plasmid pBT10 was transformed by heat shock at 42° C. for 2 min in the chemically competent strain *E. coli* W3110. For the synthesis of hydroxymethyl laurate and 12-oxomethyl laurate, *E. coli* W3110-pBT10 was cultivated overnight at 30° C. and 180 rpm in M9 medium and harvested. The biomass was taken up in M9 medium with 0.5% glucose up to OD450=0.2. After a growth time of 4 h, expression was induced with dicyclopropyl ketone and it was incubated for a further 4 hours. The cells were centrifuged, the cell pellet was resuspended in KPi-buffer (50 mM, pH 7.4) and put in a bioreactor. A biomass concentration of about 1.8 gCDW/L was established. Stirring vigorously (1500 min$^{-1}$), the substrate methyl laurate in the ratio 1:3 was added to the cell suspension (100 ml cell suspension, 50 ml methyl laurate). The temperature was kept constant at 30° C. Formation of the products hydroxymethyl laurate and 12-oxomethyl laurate was detected by GC analysis of the reaction mixture. For this, a sample was taken after 0 min as negative control (FIG. 13) and after 150 min (FIG. 14) from the organic phase of the reaction mixture, and was analysed by GC (Thermo Trace GC Ultra). The column was a Varian Inc. FactorFour™ VF-5m, length: 30 m, film thickness: 0.25 μM, inside diameter: 0.25 mm.

Analysis conditions:

| | |
|---|---|
| Furnace temperature | 80-280° C. |
| Ramp | 15° C./min |
| Split ratio | 15 |
| Injection volume | 1 μl |
| Carrier flow | 1.5 ml/min |
| PTV injector | 80-280° C. at 15° C./s |
| Detector base temperature: | 320° C. |

The detection of 12-oxomethyl laurate (FIG. 11) and 12-hydroxymethyl laurate (FIG. 12) was demonstrated by injection of the pure substances.

C Conversion of 12-Oxomethyl Laurate to 12-Aminomethyl Laurate

C1: Isolation and Expression of an Aminotransferase from *Arabidopsis thaliana*

A known aminotransferase from *Arabidopsis thaliana* was analysed. Surprisingly, 4-aminobutyrate transaminase (at3g22200, SEQ ID No. 38) displayed an activity of about 14 U/mg heterologously expressed protein versus 12-oxomethyl dodecanoate. The product 12-aminomethyl dodecanoate was confirmed by HPLC.

Unless stated otherwise, all methods were carried out in accordance with the protocols in Sambrook, J., Fritsch, E. F., & Maniatis, T (1989). Molecular Cloning, 2nd Ed. New York: Cold Spring Harbor Laboratory Press.

Isolation of 4-aminobutyrate transaminase from *A. thaliana* (at3g22200)

The RNA was isolated with the RNeasy Mini Kit from a whole, flowering plant of the species *A. thaliana* following the instructions of the manufacturer: QIAGEN GmbH, Hilden.

Then cDNA synthesis was carried out with the RT Skript Kit (USB Europe GmbH, Staufen) following the manufacturer's instructions. RNA quality/quantity determination was performed by Nanodrop following the instructions of the manufacturer (Thermo Fisher Scientific Inc. Waltham USA).

PCR from *A. thaliana* cDNA for Insertion of Cleavage Sites

Using the following primers, the DNA coding for the 4-aminobutyrate transaminase with SEQ ID No. 39 was cloned in the NaeI, BamHI digested vector

```
Forward-primer inserts protease
cleavage site and NaeI,
                                  SEQ ID No. 36
GCCGGCGAGAACCTGTACTTTCAGATGGCAAGTAAGTATGCCACTTG Reverse-primer inserts BamHI,
                                  SEQ ID No. 37
GGATCCTCACTTCTTGTGCTGAGCCTTG
```

PCR was carried out according to the following protocol:

| Preparation | Programme |
|---|---|
| 2 µl cDNA | 95° C. 3 min |
| 5 µl 10× Pfu buffer MgSO4 | 94° C. 45 sec |
| 5 µl dNTPs 2 mM | 58° C. 1 min 30 cycles |
| 2 µl primer forward 10 µM | 72° C. 4 min |
| 2 µl primer reverse 10 µM | 72° C. 10 min |
| 0.5 µl Pfu | |
| 36.5 µl H$_2$O | |

The resultant PCR product was purified with the NucleoSpin® Extract II Kit (Macherey-Nagel, Germany, following the manufacturer's instructions).

Expression of the Heterologous Protein

Using the PCR product described above, the vector pGJ3130 (FIG. 15, SEQ ID No. 43) was produced by standard methods of molecular biology and transformed in *E. coli* XL1blue. The transformed *E. coli* strain was cultivated in double YT-medium (dYT) with the antibiotic ampicillin (100 µg/ml) and addition of 0.5 mM IPTG at 28° C. up to a density of OD600 nm=0.3-0.4.

Purification of Heterologously Expressed Protein by Means of 6xHis-Tag (SEQ ID NO: 50)

Lysis of the bacterial expression culture: 50 ml culture was centrifuged at 2360 x g, and then resuspended in 5 ml Na-phophate buffer (pH 8) with 5 mM EDTA, 300 mM NaCl and 1 mg/ml lysozyme, and incubated for 1 h at RT. The lysate was centrifuged at 2360 x g for 10 min and the supernatant was purified on a Protino Ni-TED 2000 packed column (following the instructions of the manufacturer; Macherey-Nagel, Düren). The protein concentration was determined according to Bradford.

Detection of Enzyme Activity by Means of a Coupled Assay

The activity was determined in a coupled assay, in which the pyruvate that formed as by-product of the transaminase reaction is reacted further in a second step, and NADH is oxidized to NAD+. The decrease in NADH concentration (principle: measurement of the decrease in extinction) is measured in the photometer at 340 nm and provides a measure of the activity.

| Preparation | |
|---|---|
| 50 mM | Na-phosphate pH 7.5 |
| 50 mM | L-alanine |
| 100 µM | Pyridoxal phosphate |
| 250 µg | 12-oxomethyl dodecanoate |
| 1.25 mM | NADH |
| 10 U | Lactate dehydrogenase |
| 10 µg | heterologously expressed protein |

Make up to 1 ml with doubly distilled water

The assay was started by adding 5 µl 12-ODME (50 mg/ml). Measurement is performed continuously every minute at 340 nm at RT for up to max. 20 minutes.

Inactivated protein and a preparation without ω-substrate were used as the control.

FIG. 16 shows the variation in extinction, determined photometrically.

Detection of the Heterologously Expressed Protein by HPLC

| Preparation | |
|---|---|
| 50 mM | Na-phosphate pH 7.5 |
| 50 mM | L-alanine |
| 100 µM | Pyridoxal phosphate |
| 250 µg | 12-oxomethyl dodecanoate |
| 50 µg | heterologously expressed protein |

Make up to 500 µl with doubly distilled water

After incubation for 4 h at RT, the reaction was stopped with 1 Vol. MeOH

For the HPLC analysis, the preparation was derivatized with o-phthalic aldehyde (oPA) and 250 µl was analysed. 50 mM NaAC pH 4:acetonitrile 4:1 (v:v) was used as solvent A. Solvent B was acetonitrile with 5% 50 mM NaAC pH 4. The gradient was from 30% B to 60% B in 4 min, from 60% B to 100% B in 2 min. The flow rate was 1.2 ml/min.

Separation took place in an Agilent Zorbax RP18 column (Agilent Technologies, USA), the column temperature was 40° C. FIG. 17 (top) shows the formation of 12-aminomethyl laurate. The reference sample is shown at the bottom in FIG. 17.

D Amination of 12-oxomethyl laurate with PPTA5 and PSTA from *Pseudomonas*

D1. Cloning of PPTA5 and PSTA

The strains *E. coli* BL21(DE3)/PPTA5 and *E. coli* BL21(DE3)/PSTA were used for the amination of 12-oxomethyl laurate. These strains were constructed as follows. The expression vector pET-21a(+) (Novagen) was selected for the cloning of both transaminase genes. For the PPTA5 gene, SEQ ID No. 40, primers were constructed, which were intended to add the restriction cleavage sites NdeI and XhoI to the ends of the gene; primer PPTA5_NdeI: GGAATTC-CATATGAGCGTCAACAACCCGCAAACCCG (SEQ ID No. 44) and Primer PPTA5_XhoI: CCGCTCGAGTTATC-GAATCGCCTCAAGGGTCAGGTCC (SEQ ID No. 45).

For the psta gene, SEQ ID No. 41, primers with NdeI and BamHI at the ends; primer PSTA_NdeI: GGAATTCCATAT-GAGCGATTCGCAAACCCTGCACTGGC (SEQ ID No. 46) and Primer PSTA$_{13}$ BamHI: CGCGGATCCTCAGC-CCAGCACATCCTTGGCTGTCG (SEQ ID No. 47)

These primers were used in PCRs. The purified PCR products and the vector pET-21a(+) were then submitted to restriction with the restriction enzymes NdeI and XhoI or NdeI and BamHI. The cut vector was dephosphorylated with alkaline phosphatase from shrimp. The vector cut with NdeI and XhoI and the PPTA5 gene, and the vector cut with NdeI and BamHI and the psta gene, were, after ligation with T4 DNA ligase, transformed with the competent expression strain *E. coli* XL1-Blue. After some clones had been grown, the plasmids were isolated and then underwent restriction and gel electrophoretic analysis. The transaminase sequences of the clones obtained (pPPTA5 or pPSTA) were confirmed by sequence analysis. FIG. 18 shows the plasmid maps of the expression vectors.

D2. Expression of PPTA5 and PSTA

For expression, the vectors pPPTA5 and pPSTA were transformed in competent *E. coli* BL21(DE3) cells. One individual colony of each was inoculated in 5 ml LB-Amp medium (ampicillin concentration 100 μg/ml) and shaken overnight at 37° C. Then 1% was inoculated in 200 ml LB-Amp medium, shaken at 37° C. and after reaching an OD$_{600}$ of 0.5, gene expression was induced with 0.5 mM IPTG. After shaking for 20 hours at 30° C., the cells were harvested and stored at −20° C.

For digestion of the strains *E. coli* BL21(DE3)/pPPTA5 and *E. coli* BL21(DE3)/pPSTA, 0.4 g of cells from each were processed with 100 mM Tris-HCl buffer pH 7.2 to 25% cell suspensions, which were treated twice for 90 sec with ultrasound (Bandelin Sonoplus HD2070; probe MS73; 50% intensity). After centrifugation, the supernatants were removed. The raw extracts obtained were used in conversions of 12-oxomethyl laurate. The 400 μl preparations contained 5 mM 12-oxomethyl laurate, dissolved in N,N-dimethylformamide, 500 mM DL-alanine, 1 mM pyridoxal-5′-phosphate and 80 μl raw extract in 10 mM Kpi-buffer pH 7.0. It was shaken at 25° C. After specified times, 20 μl samples were taken from each, one portion was made alkaline with 1 μl 1% NaOH solution and was shaken out with 100 μl ethyl acetate. The organic phases were investigated by gas chromatography (gas chromatograph from Perkin Elmer, Clarus 500 with flame ionization detector). For this, an Optima 5-column (0.25 μm, 30 m, 0.25 mm, Macherey-Nagel) was used with programme:

| | | |
|---|---|---|
| 80° C. | | |
| 25° C./min | | 180° C. |
| 5° C./min | | 215° C. |
| 20° C./min | | 280° C. |

The retention times of 12-oxo- and 12-aminomethyl laurate are 7.2 and 7.7 min, respectively.

The results of the reactions are presented in FIGS. 20 and 21. For the evaluation, the peak areas of 12-oxo- and 12-aminomethyl laurate from the chromatograms obtained for neutral and acid extraction were added together and the percentage of educt or product was calculated.

The invention claimed is:

1. An isolated recombinant cell, which has been genetically modified relative to its wild type so that, in comparison to the wild type, the recombinant cell is able to produce more ω-aminocarboxylic acid, ω-aminocarboxylic acid esters, or more lactams derived from ω-aminocarboxylic acid, starting from carboxylic acids, or carboxylic acid esters, wherein the isolated recombinant cell comprises:

(i) a first nucleic acid encoding a heterologous enzyme $E_I$, wherein the enzyme $E_I$ catalyzes the conversion of carboxylic acids or carboxylic acid esters to the corresponding ω-aminocarboxylic acid or ω-aminocarboxylic acid esters, and wherein the enzyme $E_I$ comprises an alkane monooxygenase encoded by the alkBGT gene from *Psudomonas putida* GPo1 comprising the amino acid sequences set forth in SEQ ID NOS: 50, 51, and 52, and a cytochrome P450 monooxygenase from *Candida tropicalis*; and (ii) a second nucleic acid encoding at least one of a heterologous enzyme $E_{II}$ and a heterologous enzyme $E_{III}$, wherein the enzyme $E_{II}$ catalyzes the conversion of ω-hydroxycarboxylic acid or ω-hydroxycarboxylic acid esters to the corresponding ω-oxocarboxylic acids or ω-oxocarboxylic acid esters, wherein the enzyme $E_{II}$ is selected from the group consisting of an alkane monooxygenase, alcohol dehydrogenase, and alcohol oxidase, and wherein the enzyme $E_{III}$ catalyzes the conversion of ω-oxocarboxylic acids or ω-oxocarboxylic acid esters to the corresponding ω-aminocarboxylic acids or ω-aminocarboxylic acid esters, wherein the enzyme $E_{III}$ is a ω-transaminase, wherein the expression of the first and second nucleic acids results in overexpression of the enzyme $E_I$ and overexpression of at least one of enzyme $E_{II}$ and enzyme $E_{III}$ and wherein said expression increases the production of ω-aminocarboxylic acid, ω-aminocarboxylic acid esters, or lactams derived from ω-aminocarboxylic acid compared to the wild type cell.

2. The isolated recombinant cell according to claim 1, wherein the cell has increased activity of all the enzymes $E_I$, $E_{II}$ and $E_{III}$.

3. The isolated recombinant cell according to claim 1, wherein the enzyme $E_{II}$ is an alcohol dehydrogenase.

4. The isolated recombinant cell according to claim 1, wherein the enzyme $E_{II}$ is encoded by the alkJ gene from *Pseudomonas putida* GPo1.

5. The isolated recombinant cell according to claim 1, wherein the enzyme $E_{III}$ is the ω-transaminase CV2025 from *Chromobacterium violaceum* DSM30191.

6. The isolated recombinant cell according to claim 1, further comprising a third nucleic acid encoding a heterologous enzyme $E_{IV}$, wherein the enzyme $E_{IV}$ catalyzes the conversion of ω-aminocarboxylic acid esters to the corresponding ω-aminocarboxylic acid, and wherein the expression of the enzyme $E_{IV}$ results in overexpression of enzyme $E_{IV}$ and said overexpression increases production of ω-aminocarboxylic acid.

7. The isolated recombinant cell according to claim 6, wherein the enzyme $E_{IV}$ is the lipase LipA Q76D26 from *Pseudomonas fluorescens*, and wherein the lipase LipA Q76D26 is expressed and secreted from the cell.

8. The isolated recombinant cell according to claim 1, further comprising a fourth nucleic acid encoding a heterologous enzyme $E_V$, wherein the enzyme $E_V$ catalyzes the conversion of ω-aminocarboxylic acid to the corresponding lactams, and wherein the expression of the enzyme $E_V$ results in overexpression of enzyme $E_V$ and said overexpression increases production of lactams.

9. The isolated recombinant cell according to claim 8, wherein the enzyme $E_V$ is secreted by the cell.

10. The isolated recombinant cell according to claim 1, wherein the cell is a genetically modified *Escherichia coli* cell, a genetically modified *Corynebacterium glutamicum* cell or a genetically modified *Pseudomonas putida* cell.

11. A method for the production of a ω-aminocarboxylic acid, of a ω-aminocarboxylic acid ester or of a lactam derived from a ω-aminocarboxylic acid, comprising:

I) culturing the isolated recombinant cell according to claim 1 with a culture medium comprising a carboxylic acid or a carboxylic acid ester or with a culture medium contiguous with an organic phase comprising a carboxylic acid or a carboxylic acid ester in conditions for the cell to form a ω-aminocarboxylic acid, a ω-aminocarboxylic acid ester or a lactam derived from a ω-aminocarboxylic acid, starting from carboxylic acid or from a carboxylic acid ester;

II) optionally isolating the resultant ω-aminocarboxylic acid, the resultant ω-aminocarboxylic acid ester or the lactam derived from ω-aminocarboxylic acid.

12. The method according to claim 11, wherein the ω-aminocarboxylic acid ester formed is converted by conventional chemical methods to ω-aminocarboxylic acid.

13. The method according to claim 11, wherein the recombinant cell is a genetically modified *Escherichia coli* cell, a genetically modified *Corynebacterium glutamicum* cell or a genetically modified *Pseudomonas putida* cell.

14. The method according to claim 11, wherein the culture medium-comprises amino acids, which function as amine donor in the transaminase-catalysed conversion of the ω-oxocarboxylic acid or the ω-oxocarboxylic acid ester to the corresponding ω-aminocarboxylic acid or ω-aminocarboxylic acid ester.

15. The method according to claim 11, wherein the method is carried out in a two-phase system, comprising
A) an aqueous phase, and
B) an organic phase,
where the formation of the ω-aminocarboxylic acid, the ω-aminocarboxylic acid ester or the lactam derived from ω-aminocarboxylic acid by the cell takes place in the aqueous phase and the resultant ω-aminocarboxylic acid, the resultant ω-aminocarboxylic acid ester or the resultant lactam derived from ω-aminocarboxylic acid accumulate in the organic phase.

16. The method according to claim 11, wherein the isolation of the resultant ω-aminocarboxylic acid, the resultant ω-aminocarboxylic acid ester or the lactam derived from ω-aminocarboxylic acid takes place by an at least two-stage purification process, comprising
a) extracting the ω-aminocarboxylic acid, the ω-aminocarboxylic acid ester or the lactam derived from ω-aminocarboxylic acid from the culture medium to obtain an extract, and
b) purifying the extract obtained by distillation methods or additional extraction processes, obtaining an ω-aminocarboxylic acid phase, an ω-aminocarboxylic acid ester phase or a lactam phase with a purity of at least 99.8%.

17. The method according to claim 16, wherein the extracting is a reactive extraction.

18. The method according to claim 11, wherein the carboxylic acid is lauric acid or the carboxylic acid ester is methyl laurate and in that the lauric acid or the methyl laurate is converted to laurinlactam.

* * * * *

SEQUENCE LISTING

<160> NUMBER OF SEQ ID NOS: 53

<210> SEQ ID NO 1
<211> LENGTH: 1380
<212> TYPE: DNA
<213> ORGANISM: Chromobacterium violaceum

<400> SEQUENCE: 1

```
atgcagaagc aacgtacgac cagccaatgg cgcgaactgg atgccgccca tcacctgcat        60
ccgttcaccg ataccgcatc gctgaaccag gcgggcgcgc gcgtgatgac gcgcggagag       120
ggcgtctacc tgtgggattc ggaaggcaac aagatcatcg acggcatggc cggactgtgg       180
tgcgtgaacg tcggctacgg ccgcaaggac tttgccgaag cggcgcgccg gcagatggaa       240
gagctgccgt tctacaacac cttcttcaag accaccatc cggcggtggt cgagctgtcc       300
agcctgctgg ctgaagtgac gccggccggt ttcgaccgcg tgttctatac caattccggt       360
tccgaatcgg tggacaccat gatccgcatg gtgcgccgct actgggacgt gcagggcaag       420
ccggagaaga agacgctgat cggccgctgg aacggctatc acggctccac catcggcggc       480
gccagcctgg gcggcatgaa gtacatgcac gagcagggcg acttgccgat tccgggcatg       540
gcccacatcg agcagccttg gtggtacaag cacggcaagg acatgacgcc ggacgagttc       600
ggcgtggtgg ccgcgcgctg gctggaagag aagattctgg aaatcggcgc cgacaaggtg       660
gccgccttcg tcggcgaacc catccaggg gccggcggcg tgatcgtccc gccggccacc       720
tactggccgg aaatcgagcg catttgccgc aagtacgacg tgctgctggt ggccgacgaa       780
gtgatctgcg gcttcgggcg taccggcgaa tggttcggcc atcagcattt cggcttccag       840
cccgacctgt tcaccgccgc caagggcctg tcctccggct atctgccgat aggcgcggtc       900
```

```
tttgtcggca agcgcgtggc cgaaggcctg atcgccggcg cgacttcaa ccacggcttc    960
acctactccg gccacccggt ctgcgccgcc gtcgcccacg ccaacgtggc ggcgctgcgc   1020
gacgagggca tcgtccagcg cgtcaaggac gacatcggcc cgtacatgca aaagcgctgg   1080
cgtgaaacct tcagccgttt cgagcatgtg gacgacgtgc gcggcgtcgg catggtgcag   1140
gcgttcaccc tggtgaagaa caaggcgaag cgcgagctgt tccccgattt cggcgagatc   1200
ggcacgctgt gccgcgacat cttcttccgc aacaacctga tcatgcgggc atgcggcgac   1260
cacatcgtgt cggcgccgcc gctggtgatg acgcgggcgg aagtggacga gatgctggcg   1320
gtggcggaac gctgtctgga ggaattcgag cagacgctga aggcgcgcgg gctggcttag   1380

<210> SEQ ID NO 2
<211> LENGTH: 1137
<212> TYPE: DNA
<213> ORGANISM: Bacillus subtilis

<400> SEQUENCE: 2
atgatcatag gggttcctaa agagataaaa aacaatgaaa accgtgtcgc attaacaccc     60
gggggcgttt ctcagctcat ttcaaacggc caccgggtgc tggttgaaac aggcgcgggc    120
cttggaagcg gatttgaaaa tgaagcctat gagtcagcag gagcggaaat cattgctgat    180
ccgaagcagg tctgggacgc cgaaatggtc atgaaagtaa agaaccgct gccggaagaa    240
tatgtttatt ttcgcaaagg acttgtgctg tttacgtacc ttcatttagc agctgagcct    300
gagcttgcac aggccttgaa ggataaagga gtaactgcca tcgcatatga acggtcagt    360
gaaggccgga cattgcctct tctgacgcca atgtcagagg ttgcgggcag aatggcagcg    420
caaatcggcg ctcaattctt agaaaagcct aaaggcggaa aaggcattct gcttgccggg    480
gtgcctggcg tttcccgcgg aaaagtaaca attatcggag gaggcgttgt cgggacaaac    540
gcggcgaaaa tggctgtcgg cctcggtgca gatgtgacga tcattgactt aaacgcagac    600
cgcttgcgcc agcttgatga catcttcggc catcagatta aaacgttaat ttctaatccg    660
gtcaatattg ctgatgctgt ggcggaagcg gatctcctca tttgcgcggt attaattccg    720
ggtgctaaag ctccgactct tgtcactgag gaaatggtaa acaaatgaa acccggttca    780
gttattgttg atgtagcgat cgaccaaggc ggcatcgtcg aaactgtcga ccatatcaca    840
acacatgatc agccaacata tgaaaaacac ggggttgtgc attatgctgt agcgaacatg    900
ccaggcgcag tccctcgtac atcaacaatc gccctgacta cgttactgt tccatacgcg    960
ctgcaaatcg cgaacaaagg ggcagtaaaa gcgctcgcag acaataccggc actgagagcg   1020
ggtttaaaca ccgcaaacgg acacgtgacc tatgaagctg tagcaagaga tctaggctat   1080
gagtatgttc ctgccgagaa agctttacag gatgaatcat ctgtggcggg tgcttaa       1137

<210> SEQ ID NO 3
<211> LENGTH: 1206
<212> TYPE: DNA
<213> ORGANISM: Pseudomonas putida

<400> SEQUENCE: 3
atgcttgaga acacagagt tctggattcc gctccagagt acgtagataa aaagaaatat     60
ctctggatac tatcaacttt gtggccggct actccgatga tcggaatctg gcttgcaaat    120
gaaactggtt gggggatttt ttatgggctg gtattgctcg tatggtacgg cgcacttcca    180
ttgcttgatg cgatgtttgg tgaggacttt aataatccgc tgaagaagt ggtgccgaaa    240
ctagagaagg agcggtacta tcgagttttg acatatctaa cagttcctat gcattacgct    300
```

```
gcattaattg tgtcagcatg gtgggtcgga actcagccaa tgtcttggct tgaaattggt      360
gcgcttgcct tgtcactggg tatcgtgaac ggactagcgc tcaatacagg acacgaactc      420
ggtcacaaga aggagacttt tgatcgttgg atggccaaaa ttgtgttggc tgtcgtaggg      480
tacggtcact tctttattga gcataataag ggtcatcacc gtgatgtcgc tacaccgatg      540
gatcctgcaa catcccggat gggagaaagc atttataagt tttcaatccg tgagatccca      600
ggagcattta ttcgtgcttg ggggcttgag gaacaacgcc tttcgcgccg tggccaaagc      660
gtttggagtt tcgataatga aatcctccaa ccaatgatca tcacagttat tctttacgcc      720
gttctccttg ccttgtttgg acctaagatg ctggtgttcc tgccgattca aatggctttc      780
ggttggtggc agctgaccag tgcgaactat attgaacatt acggcttgct ccgtcaaaaa      840
atggaggacg tcgatatga gcatcaaaag ccgcaccatt cttggaatag taatcacatc      900
gtctctaatc tagtgctgtt ccaccttcag cggcactcgg atcaccacgc gcatccaaca      960
cgttcttatc agtcacttcg ggattttccc ggcctgccgg ctcttccgac gggttaccct     1020
ggtgcatttt tgatggcgat gattcctcag tggtttagat cagttatgga tcccaaggta     1080
gtagattggg ctggtggtga ccttaataag atccaaattg atgattcgat gcagaaaacc     1140
tatttgaaaa aatttggcac tagtagtgct ggtcatagtt cgagtacctc tgcggtagca     1200
tcgtag                                                                1206

<210> SEQ ID NO 4
<211> LENGTH: 519
<212> TYPE: DNA
<213> ORGANISM: Pseudomonas putida

<400> SEQUENCE: 4
atggctagct ataaatgccc ggattgtaat tatgtttatg atgagagtgc gggtaatgtg       60
catgaggggt tttctccagg tacgccttgg caccttattc ctgaggattg gtgctgcccc      120
gattgcgccg ttcgagacaa gcttgacttc atgttaattg agagcggcgt aggtgaaaag      180
ggcgtcacct caacccatac ttcgccaaat ttatccgagg ttagtggcac aagtttaact      240
gctgaagcag tggttgcgcc gacaagctta gagaaattgc ctagtgccga cgttaaaggc      300
caagatctat ataaaactca acctccaagg tctgatgccc aaggcgggaa agcatacttg      360
aagtggatat gtattacttg tggccatata tatgatgagg cgttgggcga tgaggccgag      420
ggttttactc caggtactcg ctttgaggat attcctgatg actggtgctg tccggattgc      480
ggggctacga agaagactac tgtgctctac gaggaaaag                             519

<210> SEQ ID NO 5
<211> LENGTH: 1677
<212> TYPE: DNA
<213> ORGANISM: Pseudomonas putida

<400> SEQUENCE: 5
atgtacgact atataatcgt tggtgctgga tctgcaggat gtgtgcttgc taatcgtctt       60
tcggccgacc cctctaaaag agtttgtttta cttgaagctg gccgcgaga tacgaatccg      120 ctaattcata tgccgttagg tattgctttg ctttcaaata gtaaaaagtt gaattgggct      180
tttcaaactg cgccacagca aaatctcaac ggccggagcc ttttctggcc acgaggaaaa      240
acgttaggtg gttcaagctc aatcaacgca atggtctata tccgagggca tgaagacgat      300
taccacgcat gggagcaggc ggccggccgc tactgggggtt ggtaccgggc tcttgagttg      360
```

-continued

```
ttcaaaaggc ttgaatgcaa ccagcgattc gataagtccg agcaccatgg ggttgacgga      420
gaattagctg ttagtgattt aaaatatatc aatccgctta gcaaagcatt cgtgcaagcc      480
ggcatggagg ccaatattaa tttcaacgga gatttcaacg gcgagtacca ggacggcgta      540
gggttctatc aagtaaccca aaaaaatgga caacgctgga gctcggcgcg tgcattcttg      600
cacggtgtac tttccagacc aaatctagac atcattactg atgcgcatgc atcaaaaatt      660 cttttttgaag accgtaaggc ggttggtgtt tcttatataa agaaaaatat gcaccatcaa      720
gtcaagacaa cgagtggtgg tgaagtactt cttagtcttg gcgcagtcgg cacgcctcac      780
cttctaatgc tttctggtgt tggggctgca gccgagctta aggaacatgg tgtttctcta      840
gtccatgatc ttcctgaggt ggggaaaaat cttcaagatc atttggacat acattgatg      900 tgcgcagcaa attcgagaga gccgataggg gttgctcttt ctttcatccc tcgtggtgtc      960
tcgggtttgt tttcatatgt gtttaagcgc gaggggtttc tcactagtaa cgtggcagag     1020
tcgggtggtt ttgtaaaaag ttctcctgat cgtgatcggc ccaatttgca gtttcatttc     1080
cttccaactt atcttaaaga tcacggtcga aaaatagcgg gtggttatgg ttatacgcta     1140
catatatgtg atcttttgcc taagagccga ggcagaattg gcctaaaaag cgccaatcca     1200
ttacagccgc ctttaattga cccgaactat cttagcgatc atgaagatat taaaaccatg     1260
attgcgggta ttaagatagg gcgcgctatt ttgcaggccc catcgatggc gaagcatttt     1320
aagcatgaag tagtaccggg ccaggctgtt aaaactgatg atgaaataat cgaagatatt     1380
cgtaggcgag ctgagactat ataccatccg gtaggtactt gtaggatggg taaagatcca     1440
gcgtcagttg ttgatccgtg cctgaagatc cgtgggttgg caaatattag agtcgttgat     1500
gcgtcaatta tgccgcactt ggtcgcgggt aacacaaacg ctccaactat tatgattgca     1560
gaaaatgcgg cagaaataat tatgcggaat cttgatgtgg aagcattaga ggctagcgct     1620
gagtttgctc gcgagggtgc agagctagag ttggccatga tagctgtctg catgtaa       1677
```

<210> SEQ ID NO 6
<211> LENGTH: 2649
<212> TYPE: DNA
<213> ORGANISM: Pseudomonas putida

<400> SEQUENCE: 6

```
atgaaaataa taataaataa tgatttcccg gtcgctaagg tcggagcgga tcaaattacg       60
actctagtaa gtgccaaagt tcatagttgc atatatcggc caagattgag tatcgcggat      120
ggagccgctc ccagagtatg cctttacaga gccccacctg gatatgggaa aaccgttgct      180
cttgcgttcg agtggctacg ccacagaaca gccggacgtc ctgcagtgtg gctttcttta      240
agagccagtt cttacagtga atttgatatc tgcgcagaga ttattgagca gcttgaaact      300
ttcgaaatgg taaaattcag ccgtgtgaga gagggtgtga gcaagcctgc gctcttgcga      360
gaccttgcat ctagtctttg gcagagcacc tcgataacg agatagaaac gctagttttgt      420 ttggataata ttaatcatga cttagacttg ccgttgttgc acgcacttat ggagtttatg      480
ttaaatacac caaaaaatat caggtttgca gttgcaggca atacaataaa agggttctcg      540
cagcttaaac ttgcaggcgc tatgcgggag tacaccgaga aagacttggc ctttagcgca      600
gaagaggcgg tggcgttagc ggaggcagag tctgttcttg gagttcctga agaacagata      660
gagaccttgg tgcaagaagt tgagggggtgg cctgctcttg tagttttttt gttaaagcgt      720
gagttgccgc ccaagcatat ttcagcagta gttgaagtag acaattactt tagggatgaa      780
atatttgagg cgattcccga gcgctatcgt gttttttcttg caaattcttc attgctcgat      840
```

```
ttcgtgacgc ctgatcaata caattatgta ttcaaatgcg tcaatggggt ctcatgtatt        900
aagtatttaa gcactaatta catgttgctt cgccatgtga gcggtgagcc agcgcagttt        960
acactgcatc cagtactgcg taattttcta cgagaaatta cttggactga aaatcctgct       1020
aaaagatcct acctgcttaa gcgtgcagct ttctggcatt ggcgtagagg tgaataccag       1080
tatgcaatac gaatatccct acgggcgaat gactgtcgct gggcagtcag catgtctgag       1140
agaataattt tagatttgtc atttcgtcag ggcgaaatag atgcgctgag acagtggctg       1200
ttagagctgc cgaagcaggc ctggcaccaa aaacccatag tgcttattag ttacgcgtgg       1260
gtattgtatt tcagtcagca aggcgcgcga gcagagaagt taattaaaga cctatcttca       1320
caatccgata aaaaaaataa atggcaagaa aaggaatggc tgcagcttgt gcttgcaata       1380
ggtaaagcaa ccaaagatga aatgcttccg agtgaggagc tctgtaataa gtggattagt       1440
ttatttgggg attcaaacgc agttggaaaa ggggccgcgc taacctgttt ggcttttatt       1500
tttgccagtg agtatagatt tgcagagttg agaaggtgc tggctcaggc ccaagccgtg       1560
aataaatttg caaaacaaaa ttttgctttt ggttggctgt atgtcgcgag gtttcaacaa       1620
gccctagcaa gcggaaaaat gggctgggcg aggcagatta taactcaagc acgcacagac       1680
agtcgcgcgc agatgatgga atccgagttt acttcgaaaa tgtttgacgc tctagagctt       1740
gagttacatt atgaattgcg ctgcttggac acctcagaag aaaagctctc caaaatttta       1800
gagttcattt ccaatcacgg ggtgacagac gtgttttttt ccgtatgccg tgctgtgtca       1860
gcttggcggc ttggaaggag tgacctaaat ggctccattg agatattgga gtgggcgaag       1920
gcgcatgcgg ttgaaaaaaa tctaccaaga ttggaagtta tgagccaaat tgagatctat       1980
cagcgcttag tctgtcaagg cataacgggc ataataatt taaaaactct tgaagatcat       2040
aagattttct ccggacagca ctcagccccc ctaaaagcac gcctgctgct tgttcaatca       2100
ctagtgcttt cccgagatcg gaactttcat agtgccgcgc acagagcgtt attggctatt       2160
cagcaagccc gtaaaattaa cgcgggccag ctggaagtcc gtggattatt gtgtttggcc       2220
ggagcgcagg caggtgccgg tgatttaaaa aaggctcagc ttaacattgt ttatgcagtg       2280
gagatagcaa aacagcttca atgctttcaa acagttcttg atgaagtatg tttaattgag       2340
cgaataatac cggcttcatg tgaagccttc acagcagtta atttagatca agcgattggg       2400
gcttttagtc ttccgcgaat agttgagatt ggaaagtccg cagagaataa agctgacgct       2460
ttattgacac ggaagcagat tgctgtcttg aggcttgtaa agagggggtg ctcaaacaaa       2520
caaatagcaa caaatatgca tgtcaccgaa gatgctataa agtggcatat gaggaaaata       2580
tttgccacct tgaatgtagt gaatcgcacg caagcaacaa ttgaagctga gcgtcaagga       2640
attatctaa                                                             2649
```

```
<210> SEQ ID NO 7
<211> LENGTH: 1158
<212> TYPE: DNA
<213> ORGANISM: Pseudomonas putida

<400> SEQUENCE: 7
atggcaatcg ttgttgttgg cgctggtaca gctggagtaa atgctgcgtt ctggcttcgt         60
caatatggtt ataaagggga aattaggatt tttagcaggg agtctgtggc gccttatcag        120
cggcctcctc tatccaaggc ttttctgaca agtgagattg cagaatccgc agtgccatta        180
aagccagaag gttttatac gaataacaat attaccattt cgttaaatac accgattgta        240
```

| tcaatcgacg | tgggcgtaa | atagtttct | tctaaagatg | gaaagaata | cgcgtatgaa | 300 |
| aaattgattc | ttgcaacacc | tgctagcgca | cgtaggttaa | cctgcgaggg | gtctgaactg | 360 |
| tctgggtct | gctatttacg | cagtatggaa | gacgccaaaa | atttacgtag | gaaacttgtg | 420 |
| gagagtgcgt | ctgttgttgt | gttgggcggc | ggagtaatcg | ggcttgaagt | cgcctcagct | 480 |
| gcggtgggct | tagggaagag | ggtcacagtg | atagaagcca | ccccgcgtgt | aatggcgcgc | 540 |
| gtggttacgc | cggcagcagc | aaacttagtc | agagcccgcc | tggaggctga | aggaattgag | 600 |
| ttcaagctga | atgcgaaatt | aacgtctata | aagggcagga | atggccatgt | tgaacaatgc | 660 |
| gtacttgaaa | gtggagaaga | aattcaggcg | gatctgattg | tagttggaat | cggtgctatc | 720 |
| ccagagctag | agctggcaac | tgaggcggcc | cttgaagtga | gtaatggtgt | tgtggtcgat | 780 |
| gatcagatgt | gtacatcgga | tacaagtata | tatgcaatcg | gcgactgcgc | aatggctaga | 840 |
| aatccttttt | ggggaacgat | ggtacgttta | gagacaattc | ataatgcggt | tacacacgct | 900 |
| caaattgtcg | caagtagcat | ctgtggcaca | tcaacaccag | caccaaccc | accacggttc | 960 |
| tggtctgatc | ttaaagggat | ggcgctgcaa | ggacttggtg | ctctaaagga | ctacgataaa | 1020 |
| ctcgttgttg | caattaataa | cgaaactctt | gaactagaag | tccttgcgta | caagcaggag | 1080 |
| cgactgattg | caactgagac | aataaatttg | cctaaacgtc | aaggtgcgct | tgcagggagt | 1140 |
| ataaaattac | ctgattag | | | | | 1158 |

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
acgtagcggc cgcctaatca ggtaatttta tac    33

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
gagcgagcta tctggt    16

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
tcgtagcggc cgcccagcag acgacggagc aa    32

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
attttatctt ctcgaggctt ttcctcgtag agcacat                                    37

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgctctaacg aggaaaagcc tcgagaagat aaaatgta                                   38

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
attgacgcgg ccgcttacat gcagacagct atca                                       34

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgaggagctc aggaggatcc aagcatgcag aagcaacgta cg                              42

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtcatgtacc cctaagccag cccgcgcgcc t                                          31

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acctatctag aaggaggacg catatgatca tagggttcc t                                41

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
aacctctgca gttaagcacc cgccac                                          26
```

<210> SEQ ID NO 18
<211> LENGTH: 1853
<212> TYPE: DNA
<213> ORGANISM: Pseudomonas fluoreszenz

<400> SEQUENCE: 18

```
atgggtgtgt atgactacaa aaacttcggc acggcggatt ccaaggcgtt gttcagcgat     60
gccatggcga tcacgctgta ttcctaccac aacctcgata acggttttgc cgccggttat    120
agcacaacgg ttttggcctt ggcctgccgg cgacgctggt cacggcgttg ctcggcggta    180
ccgattccca gggcgtcatc cccggcattc cgtggaatcc cgattcggaa aaactcgccc    240
tcgaagccgt gaaaaaggcc ggctggacgc cgatcacggc ctcgcaactg gctacgacg    300
gcaagaccga cgcacgcgga accttctttg gcgagaaggc cggttactcg acagcgcagg    360
tcgagattct cggcaagtac gacgcccagg ccatctcac agaaatcggc atcgcctttc    420
gcggcaccag cggcccgcgc gagaacctga tccttgattc catcggcgac gtgatcaacg    480
acttgctcgc cgcgttcggc cccaaggatt acgccaagaa ctacgtcggc gaagcgttcg    540
gcaacctgct caatgacgtg gtcgcctttg ccaaggccaa tggcctcagc ggcaaggacg    600
tgctggtcag cggccacagc ctcggcgggc tgcggtcaa cagcatggcg gatttgagcg    660
gcggcaagtg gggcgggttc ttcgccgact ccaactacat cgcctatgcc tcgccgaccc    720
agagcagcac cgacaaagtg ctcaacgtcg gctacgagaa cgacccggtg ttccgcgccc    780
tcgacggttc gaatttcacc ggcgcctcga ttggcgtgca cgacgcgccg aaggaatcgg    840
ccaccgacaa catcgtcagc ttcaacgatc actacgcctc gacggcgtgg aatctgctgc    900
cgttctccat cctcaacatc ccgacctgga tctcgcacct gccaaccgct acggcgacg    960
gcatgaaccg ggtgatcgag tcgaagttct acgacctgac cagcaaggac tcgacgatca   1020
tcgtcgccaa cctgtcggat ccggcgcggg ccaacacctg ggtgcaggat ctcaaccgca   1080
acgccgaaac ccacaagggc agcaccttca tcatcggcag cgacgccaac gatctgattc   1140
agggtggcag cggcaatgac tatctggaag gtcgcgccgg caacgacacc tttcgcgaca   1200
gcggcggcta acatcatc ctgggcgggc agggcagcaa tacgctggac ttgcagaagt   1260
cggtgaatac cttcgacttc gccaacgacg cgccggcaa tctgtacatt cgcgatgcca   1320
acggcgggat cagcatcacc cgcgacatcg gcgccatcgt caccaaagag ccgggcttcc   1380
tctggggtct gttcaaggac gacgtgaccc acagcgtcac ggccagtggc ttgaaggtcg   1440
gcaacaacct gaccgcctac gagtcgagcg tgaagggcag caacggcgcc gacacgctca   1500
aggcgcatgc cggcggcgac tggttgttcg gcctcgacgg caacgatcat ctgatcggcg   1560
gggcgggcaa cgatgtgttt gttggcgggcg ccggtaacga tctgatggag tccggggggcg   1620
gggcggatac gttcctgttc aacggcgcgt cggccagga tcgggtggtg ggattcacgt   1680
ccaacgacaa actggtgttt ctcggcgtgc agggtgtgtt gcctggcgat gacttccgag   1740
cgcatgcctc ggcagccggg caggataccg tgctgaagtt cggcggcgat tcggtgacat   1800
tggttggcgt ttcgctgggg agtttgagtg gcgatggaat tgtgatcgcc tga          1853
```

<210> SEQ ID NO 19
<211> LENGTH: 503
<212> TYPE: PRT
<213> ORGANISM: Pseudomonas putida

```
<220> FEATURE:
<223> OTHER INFORMATION: Strain W619

<400> SEQUENCE: 19
```

| | | | | | | | | | | | | | | |
|---|---|---|---|---|---|---|---|---|---|---|---|---|---|---|
| Met | Ser | Lys | Ser | Leu | Thr | Trp | Ala | Arg | Gly | Ser | Gly | Arg | Arg | Leu | Ile |
| 1 | | | | 5 | | | | | 10 | | | | | 15 | |

Met Ser Lys Ser Leu Thr Trp Ala Arg Gly Ser Gly Arg Arg Leu Ile
1               5                   10                  15

Ser Leu Val Leu Arg Tyr Leu Lys Ile Arg Asn Val Val Phe Phe Arg
                20                  25                  30

Leu Tyr Pro Arg Ala Asn Leu Ala Ala Thr Thr Ser Ile Val Ala Tyr
            35                  40                  45

Ser Phe Phe Glu Glu Pro Pro Met Asn Met Pro Glu Thr Ala Pro Ala
        50                  55                  60

Gly Ile Ala Ser Gln Leu Lys Leu Asp Ala His Trp Met Pro Tyr Thr
65                  70                  75                  80

Ala Asn Arg Asn Phe His Arg Asp Pro Arg Leu Ile Val Ala Ala Glu
                85                  90                  95

Gly Asn Tyr Leu Val Asp Asp Lys Gly Arg Arg Ile Phe Asp Ala Leu
            100                 105                 110

Ser Gly Leu Trp Thr Cys Gly Ala Gly His Thr Arg Lys Glu Ile Thr
        115                 120                 125

Glu Ala Val Ala Arg Gln Leu Gly Thr Leu Asp Tyr Ser Pro Ala Phe
130                 135                 140

Gln Phe Gly His Pro Leu Ser Phe Gln Leu Ala Glu Lys Ile Thr Ala
145                 150                 155                 160

Leu Thr Pro Gly Asp Leu Asn His Val Phe Tyr Thr Asn Ser Gly Ser
                165                 170                 175

Glu Cys Ala Asp Thr Ala Leu Lys Met Val Arg Ala Tyr Trp Arg Leu
            180                 185                 190

Lys Gly Gln Ala Thr Lys Thr Lys Ile Ile Gly Arg Ala Arg Gly Tyr
        195                 200                 205

His Gly Val Asn Ile Ala Gly Thr Ser Leu Gly Gly Val Asn Gly Asn
210                 215                 220

Arg Lys Met Phe Gly Gln Leu Leu Asp Val Asp His Leu Pro His Thr
225                 230                 235                 240

Val Leu Pro Val Asn Ala Phe Ser Lys Gly Leu Pro Glu Glu Gly Gly
                245                 250                 255

Ile Ala Leu Ala Asp Glu Met Leu Lys Leu Ile Glu Leu His Asp Ala
            260                 265                 270

Ser Asn Ile Ala Ala Val Ile Val Glu Pro Leu Ala Gly Ser Ala Gly
        275                 280                 285

Val Leu Pro Pro Pro Lys Gly Tyr Leu Lys Arg Leu Arg Glu Ile Cys
290                 295                 300

Thr Gln His Asn Ile Leu Leu Ile Phe Asp Glu Val Ile Thr Gly Phe
305                 310                 315                 320

Gly Arg Met Gly Ala Met Thr Gly Ala Glu Ala Phe Gly Val Thr Pro
                325                 330                 335

Asp Leu Met Cys Ile Ala Lys Gln Val Thr Asn Gly Ala Ile Pro Met
            340                 345                 350

Gly Ala Val Ile Ala Ser Ser Glu Ile Tyr Gln Thr Phe Met Asn Gln
        355                 360                 365

Pro Thr Pro Glu Tyr Ala Val Glu Phe Pro His Gly Tyr Thr Tyr Ser
370                 375                 380

Ala His Pro Val Ala Cys Ala Ala Gly Ile Ala Ala Leu Asp Leu Leu
385                 390                 395                 400

```
Gln Arg Glu Asn Leu Val Gln Ser Ala Ala Glu Leu Ala Pro His Phe
            405                 410                 415

Glu Lys Leu Leu His Gly Val Lys Gly Thr Lys Asn Val Val Asp Ile
        420                 425                 430

Arg Asn Tyr Gly Leu Ala Gly Ala Ile Gln Ile Ala Ala Arg Asp Gly
        435                 440                 445

Asp Ala Ile Val Arg Pro Tyr Glu Val Ala Met Lys Leu Trp Lys Ala
    450                 455                 460

Gly Phe Tyr Val Arg Phe Gly Gly Asp Thr Leu Gln Phe Gly Pro Thr
465                 470                 475                 480

Phe Asn Thr Thr Pro Gln Gln Leu Asp Arg Leu Phe Asp Ala Val Gly
            485                 490                 495

Glu Asn Leu Asn Leu Ile Asp
            500

<210> SEQ ID NO 20
<211> LENGTH: 460
<212> TYPE: PRT
<213> ORGANISM: Pseudomonas aeruginosa
<220> FEATURE:
<223> OTHER INFORMATION: Strain PA01

<400> SEQUENCE: 20

Met Thr Ala Gln Leu Asn Pro Gln Arg Asp Thr Arg Asp Tyr Gln Gln
1               5                   10                  15

Leu Asp Ala Ala His His Ile His Ala Phe Leu Asp Gln Lys Ala Leu
            20                  25                  30

Asn Arg Glu Gly Pro Arg Val Met Val Arg Gly Asp Gly Leu Gln Leu
        35                  40                  45

Trp Asp Asn Asp Gly Lys Arg Tyr Leu Asp Gly Met Ser Gly Leu Trp
    50                  55                  60

Cys Thr Asn Leu Gly Tyr Gly Arg Gln Asp Leu Ala Ala Ala Ala Ser
65              70                  75                  80

Arg Gln Leu Glu Gln Leu Pro Tyr Tyr Asn Met Phe Phe His Thr Thr
            85                  90                  95

His Pro Ala Val Val Glu Leu Ser Glu Met Leu Phe Ser Leu Leu Pro
        100                 105                 110

Asp His Tyr Ser His Ala Ile Tyr Thr Asn Ser Gly Ser Glu Ala Asn
    115                 120                 125

Glu Val Leu Ile Arg Thr Val Arg Arg Tyr Trp Gln Ile Leu Gly Lys
130                 135                 140

Pro Gln Lys Lys Ile Met Ile Gly Arg Trp Asn Gly Tyr His Gly Ser
145                 150                 155                 160

Thr Leu Gly Ser Thr Ala Leu Gly Gly Met Lys Phe Met His Glu Met
            165                 170                 175

Gly Gly Met Leu Pro Asp Phe Ala His Ile Asp Glu Pro Tyr Trp Tyr
        180                 185                 190

Ala Asn Gly Gly Glu Leu Ser Pro Ala Glu Phe Gly Arg Arg Ala Ala
    195                 200                 205

Leu Gln Leu Glu Glu Lys Ile Leu Glu Leu Gly Ala Glu Asn Val Ala
210                 215                 220

Ala Phe Val Ala Glu Pro Phe Gln Gly Ala Gly Gly Met Ile Phe Pro
225                 230                 235                 240

Pro Gln Ser Tyr Trp Pro Glu Ile Gln Arg Ile Cys Arg Gln Tyr Asp
            245                 250                 255
```

-continued

Val Leu Leu Cys Ala Asp Glu Val Ile Gly Gly Phe Gly Arg Thr Gly
            260                 265                 270

Glu Trp Phe Ala His Glu His Phe Gly Phe Gln Pro Asp Thr Leu Ser
        275                 280                 285

Ile Ala Lys Gly Leu Thr Ser Gly Tyr Ile Pro Met Gly Gly Leu Val
        290                 295                 300

Leu Gly Lys Arg Ile Ala Glu Val Leu Val Glu Gln Gly Gly Val Phe
305                 310                 315                 320

Ala His Gly Leu Thr Tyr Ser Gly His Pro Val Ala Ala Val Ala
                325                 330                 335

Ile Ala Asn Leu Lys Ala Leu Arg Asp Glu Gly Val Val Thr Arg Val
                340                 345                 350

Arg Glu Glu Thr Gly Pro Tyr Leu Gln Arg Cys Leu Arg Glu Val Phe
            355                 360                 365

Gly Asp His Pro Leu Val Gly Glu Val Gln Gly Ala Gly Phe Val Ala
370                 375                 380

Ala Leu Gln Phe Ala Glu Asp Lys Val Thr Arg Lys Arg Phe Ala Asn
385                 390                 395                 400

Glu Asn Asp Leu Ala Trp Arg Cys Arg Thr Ile Gly Phe Glu Glu Gly
                405                 410                 415

Val Ile Ile Arg Ser Thr Leu Gly Arg Met Ile Met Ala Pro Ala Leu
            420                 425                 430

Val Ala Gly Arg Ala Glu Ile Asp Glu Leu Ile Asp Lys Thr Arg Ile
            435                 440                 445

Ala Val Asp Arg Thr Ala Arg Glu Ile Gly Val Leu
            450                 455                 460

<210> SEQ ID NO 21
<211> LENGTH: 448
<212> TYPE: PRT
<213> ORGANISM: Pseudomonas aeruginosa
<220> FEATURE:
<223> OTHER INFORMATION: Strain PA01

<400> SEQUENCE: 21

Met Asn Gln Pro Leu Asn Val Ala Pro Val Ser Ser Glu Leu Asn
1               5                   10                  15

Leu Arg Ala His Trp Met Pro Phe Ser Ala Asn Arg Asn Phe Gln Lys
            20                  25                  30

Asp Pro Arg Ile Ile Val Ala Ala Glu Gly Ser Trp Leu Thr Asp Asp
        35                  40                  45

Lys Gly Arg Lys Val Tyr Asp Ser Leu Ser Gly Leu Trp Thr Cys Gly
    50                  55                  60

Ala Gly His Ser Arg Lys Glu Ile Gln Glu Val Ala Arg Gln Leu
65                  70                  75                  80

Gly Thr Leu Asp Tyr Ser Pro Gly Phe Gln Tyr Gly His Pro Leu Ser
                85                  90                  95

Phe Gln Leu Ala Glu Lys Ile Ala Gly Leu Leu Pro Gly Glu Leu Asn
            100                 105                 110

His Val Phe Phe Thr Gly Ser Gly Ser Glu Cys Ala Asp Thr Ser Ile
        115                 120                 125

Lys Met Ala Arg Ala Tyr Trp Arg Leu Lys Gly Gln Pro Gln Lys Thr
    130                 135                 140

Lys Leu Ile Gly Arg Ala Arg Gly Tyr His Gly Val Asn Val Ala Gly
145                 150                 155                 160

```
Thr Ser Leu Gly Gly Ile Gly Gly Asn Arg Lys Met Phe Gly Gln Leu
            165                 170                 175

Met Asp Val Asp His Leu Pro His Thr Leu Gln Pro Gly Met Ala Phe
            180                 185                 190

Thr Arg Gly Met Ala Gln Thr Gly Gly Val Glu Leu Ala Asn Glu Leu
            195                 200                 205

Leu Lys Leu Ile Glu Leu His Asp Ala Ser Asn Ile Ala Ala Val Ile
            210                 215                 220

Val Glu Pro Met Ser Gly Ser Ala Gly Val Leu Val Pro Pro Val Gly
225                 230                 235                 240

Tyr Leu Gln Arg Leu Arg Glu Ile Cys Asp Gln His Asn Ile Leu Leu
            245                 250                 255

Ile Phe Asp Glu Val Ile Thr Ala Phe Gly Arg Leu Gly Thr Tyr Ser
            260                 265                 270

Gly Ala Glu Tyr Phe Gly Val Thr Pro Asp Leu Met Asn Val Ala Lys
            275                 280                 285

Gln Val Thr Asn Gly Ala Val Pro Met Gly Ala Val Ile Ala Ser Ser
            290                 295                 300

Glu Ile Tyr Asp Thr Phe Met Asn Gln Ala Leu Pro Glu His Ala Val
305                 310                 315                 320

Glu Phe Ser His Gly Tyr Thr Tyr Ser Ala His Pro Val Ala Cys Ala
            325                 330                 335

Ala Gly Leu Ala Ala Leu Asp Ile Leu Ala Arg Asp Asn Leu Val Gln
            340                 345                 350

Gln Ser Ala Glu Leu Ala Pro His Phe Glu Lys Gly Leu His Gly Leu
            355                 360                 365

Gln Gly Ala Lys Asn Val Ile Asp Ile Arg Asn Cys Gly Leu Ala Gly
            370                 375                 380

Ala Ile Gln Ile Ala Pro Arg Asp Gly Asp Pro Thr Val Arg Pro Phe
385                 390                 395                 400

Glu Ala Gly Met Lys Leu Trp Gln Gln Gly Phe Tyr Val Arg Phe Gly
            405                 410                 415

Gly Asp Thr Leu Gln Phe Gly Pro Thr Phe Asn Ala Arg Pro Glu Glu
            420                 425                 430

Leu Asp Arg Leu Phe Asp Ala Val Gly Glu Ala Leu Asn Gly Ile Ala
            435                 440                 445

<210> SEQ ID NO 22
<211> LENGTH: 444
<212> TYPE: PRT
<213> ORGANISM: Pseudomonas aeruginosa
<220> FEATURE:
<223> OTHER INFORMATION: Strain PA01

<400> SEQUENCE: 22

Met Thr Met Asn Asp Glu Pro Gln Ser Ser Leu Asp Asn Phe Trp
1               5                   10                  15

Met Pro Phe Thr Ala Asn Arg Gln Phe Lys Ala Arg Pro Arg Leu Leu
            20                  25                  30

Glu Ser Ala Glu Gly Ile His Tyr Ile Ala Gln Gly Gly Arg Arg Ile
            35                  40                  45

Leu Asp Gly Thr Ala Gly Leu Trp Cys Cys Asn Ala Gly His Gly Arg
            50                  55                  60

Arg Glu Ile Ser Glu Ala Val Ala Arg Gln Ile Ala Thr Leu Asp Tyr
65                  70                  75                  80
```

```
Ala Pro Pro Phe Gln Met Gly His Pro Leu Pro Phe Glu Leu Ala Ala
                85                  90                  95

Arg Leu Thr Glu Ile Ala Pro Pro Ser Leu Asn Lys Val Phe Phe Thr
           100                 105                 110

Asn Ser Gly Ser Glu Ser Ala Asp Thr Ala Leu Lys Ile Ala Leu Ala
       115                 120                 125

Tyr Gln Arg Ala Ile Gly Gln Gly Thr Arg Thr Arg Leu Ile Gly Arg
130                 135                 140

Glu Leu Gly Tyr His Gly Val Gly Phe Gly Gly Leu Ser Val Gly Gly
145                 150                 155                 160

Met Val Asn Asn Arg Lys Ala Phe Ser Ala Asn Leu Leu Pro Gly Val
               165                 170                 175

Asp His Leu Pro His Thr Leu Asp Val Ala Arg Asn Ala Phe Thr Val
           180                 185                 190

Gly Leu Pro Glu His Gly Val Glu Lys Ala Glu Glu Leu Glu Arg Leu
       195                 200                 205

Val Thr Leu His Gly Ala Glu Asn Ile Ala Ala Val Ile Val Glu Pro
210                 215                 220

Met Ser Gly Ser Ala Gly Val Val Leu Pro Pro Lys Gly Tyr Leu Gln
225                 230                 235                 240

Arg Leu Arg Glu Ile Thr Arg Lys His Gly Ile Leu Leu Ile Phe Asp
               245                 250                 255

Glu Val Ile Thr Gly Phe Gly Arg Val Gly Glu Ala Phe Ala Ala Gln
           260                 265                 270

Arg Trp Gly Val Val Pro Asp Leu Leu Thr Cys Ala Lys Gly Leu Thr
       275                 280                 285

Asn Gly Ser Ile Pro Met Gly Ala Val Phe Val Asp Glu Lys Ile His
290                 295                 300

Ala Ala Phe Met Gln Gly Pro Gln Gly Ala Ile Glu Phe Phe His Gly
305                 310                 315                 320

Tyr Thr Tyr Ser Gly His Pro Val Ala Cys Ala Ala Ala Leu Ala Thr
               325                 330                 335

Leu Asp Ile Tyr Arg Arg Asp Asp Leu Phe Gln Arg Ala Val Glu Leu
           340                 345                 350

Glu Gly Tyr Trp Gln Asp Ala Leu Phe Ser Leu Arg Asp Leu Pro Asn
       355                 360                 365

Val Val Asp Ile Arg Ala Val Gly Leu Val Gly Val Gln Leu Ala
370                 375                 380

Pro His Ala Asp Gly Pro Gly Lys Arg Gly Tyr Asp Val Phe Glu Arg
385                 390                 395                 400

Cys Phe Trp Glu His Asp Leu Met Val Arg Val Thr Gly Asp Ile Ile
               405                 410                 415

Ala Met Ser Pro Pro Leu Ile Ile Asp Lys Pro His Ile Asp Gln Ile
           420                 425                 430

Val Glu Arg Leu Ala Gln Ala Ile Arg Ala Ser Val
       435                 440
```

<210> SEQ ID NO 23
<211> LENGTH: 468
<212> TYPE: PRT
<213> ORGANISM: Pseudomonas aeruginosa
<220> FEATURE:
<223> OTHER INFORMATION: Strain PA01

<400> SEQUENCE: 23

```
Met Asn Ala Arg Leu His Ala Thr Ser Pro Leu Gly Asp Ala Asp Leu
1               5                   10                  15

Val Arg Ala Asp Gln Ala His Tyr Met His Gly Tyr His Val Phe Asp
                20                  25                  30

Asp His Arg Val Asn Gly Ser Leu Asn Ile Ala Ala Gly Asp Gly Ala
            35                  40                  45

Tyr Ile Tyr Asp Thr Ala Gly Asn Arg Tyr Leu Asp Ala Val Gly Gly
        50                  55                  60

Met Trp Cys Thr Asn Ile Gly Leu Gly Arg Glu Glu Met Ala Arg Thr
65                  70                  75                  80

Val Ala Glu Gln Thr Arg Leu Leu Ala Tyr Ser Asn Pro Phe Cys Asp
                85                  90                  95

Met Ala Asn Pro Arg Ala Ile Glu Leu Cys Arg Lys Leu Ala Glu Leu
            100                 105                 110

Ala Pro Gly Asp Leu Asp His Val Phe Leu Thr Thr Gly Gly Ser Thr
        115                 120                 125

Ala Val Asp Thr Ala Ile Arg Leu Met His Tyr Tyr Gln Asn Cys Arg
    130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
                165                 170                 175

Pro Ala Glu Phe Asp Phe Leu Asp Glu Arg Ile His His Leu Ala Cys
            180                 185                 190

Pro Tyr Tyr Tyr Arg Ala Pro Glu Gly Leu Gly Glu Ala Glu Phe Leu
        195                 200                 205

Asp Gly Leu Val Asp Glu Phe Glu Arg Lys Ile Leu Glu Leu Gly Ala
    210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
                245                 250                 255

Gln Arg Tyr Asp Val Leu Tyr Ile Ser Asp Glu Val Val Thr Ser Phe
            260                 265                 270

Gly Arg Leu Gly His Phe Phe Ala Ser Gln Ala Val Phe Gly Val Gln
        275                 280                 285

Pro Asp Ile Ile Leu Thr Ala Lys Gly Leu Thr Ser Gly Tyr Gln Pro
    290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
                325                 330                 335

Pro Val Ala Cys Ala Ala Ala Leu Lys Asn Ile Glu Ile Ile Glu Arg
            340                 345                 350

Glu Gly Leu Leu Ala His Ala Asp Glu Val Gly Arg Tyr Phe Glu Glu
        355                 360                 365

Arg Leu Gln Ser Leu Arg Asp Leu Pro Ile Val Gly Asp Val Arg Gly
    370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
                405                 410                 415
```

```
Ala Gln Lys Arg Gly Leu Leu Val Arg Pro Ile Val His Leu Asn Val
            420                 425                 430

Met Ser Pro Pro Leu Ile Leu Thr Arg Glu Gln Val Asp Thr Val Val
        435                 440                 445

Arg Val Leu Arg Glu Ser Ile Glu Glu Thr Val Glu Asp Leu Val Arg
    450                 455                 460

Ala Gly His Arg
465

<210> SEQ ID NO 24
<211> LENGTH: 460
<212> TYPE: PRT
<213> ORGANISM: Pseudomonas putida
<220> FEATURE:
<223> OTHER INFORMATION: Strain W619

<400> SEQUENCE: 24

Met Asn Ala Pro Phe Gln Pro Gln Arg Asp Thr Arg Asp Tyr Gln Ala
1               5                   10                  15

Ser Asp Ala Ala His His Ile His Ala Phe Leu Asp Gln Lys Ala Leu
            20                  25                  30

Asn Ala Glu Gly Pro Arg Val Ile Thr Arg Gly Glu Arg Leu Tyr Leu
        35                  40                  45

Trp Asp Asn Asp Gly Arg Arg Tyr Leu Asp Gly Met Ser Gly Leu Trp
    50                  55                  60

Cys Thr Gln Leu Gly Tyr Gly Arg Lys Asp Leu Thr Ala Ala Ala Ala
65                  70                  75                  80

Ala Gln Met Asp Gln Leu Ala Tyr Tyr Asn Met Phe Phe His Thr Thr
                85                  90                  95

His Pro Ala Val Ile Glu Leu Ser Glu Leu Leu Phe Ser Leu Leu Pro
            100                 105                 110

Gly His Tyr Ser His Ala Ile Tyr Thr Asn Ser Gly Ser Glu Ala Asn
        115                 120                 125

Glu Val Leu Ile Arg Thr Val Arg Arg Tyr Trp Gln Val Val Gly Gln
    130                 135                 140

Pro Asn Lys Lys Val Met Ile Gly Arg Trp Asn Gly Tyr His Gly Ser
145                 150                 155                 160

Thr Leu Ala Ala Thr Ala Leu Gly Gly Met Lys Phe Met His Glu Met
                165                 170                 175

Gly Gly Leu Ile Pro Asp Val Ala His Ile Asp Glu Pro Tyr Trp Tyr
            180                 185                 190

Ala Glu Gly Gly Glu Leu Thr Pro Ala Glu Phe Gly Arg Arg Cys Ala
        195                 200                 205

Leu Gln Leu Glu Glu Lys Ile Leu Glu Leu Gly Ala Glu Asn Val Ala
    210                 215                 220

Gly Phe Val Ala Glu Pro Phe Gln Gly Ala Gly Gly Met Ile Phe Pro
225                 230                 235                 240

Pro Glu Ser Tyr Trp Pro Glu Ile Gln Arg Ile Cys Arg Gln Tyr Asp
                245                 250                 255

Val Leu Leu Cys Ala Asp Glu Val Ile Gly Gly Phe Gly Arg Thr Gly
            260                 265                 270

Glu Trp Phe Ala His Glu Tyr Phe Gly Phe Glu Pro Asp Thr Leu Ser
        275                 280                 285

Ile Ala Lys Gly Leu Thr Ser Gly Tyr Val Pro Met Gly Gly Leu Val
    290                 295                 300
```

```
Leu Ser Lys Arg Ile Ala Glu Ala Leu Val Glu Arg Gly Gly Val Phe
305                 310                 315                 320

Ala His Gly Leu Thr Tyr Ser Gly His Pro Val Ala Ala Val Ala
            325                 330                 335

Ile Ala Asn Leu Lys Ala Leu Arg Asp Glu Gly Ile Val Arg Gln Val
            340                 345                 350

Lys Asp Asp Thr Gly Pro Tyr Leu Gln Arg Ile Leu Arg Glu Val Phe
            355                 360                 365

Ala Asn His Pro Leu Ile Gly Gln Val Gln Gly Ala Gly Leu Val Ala
            370                 375                 380

Ala Leu Gln Phe Ala Glu Asp Lys Gly Ser Arg Lys Arg Tyr Ala Asn
385                 390                 395                 400

Glu Asn Asp Leu Ala Trp Gln Cys Arg Thr Tyr Gly Phe Glu Glu Gly
            405                 410                 415

Val Ile Ile Arg Ser Thr Leu Gly Arg Met Ile Met Ala Pro Ala Leu
            420                 425                 430

Val Ala Thr His Gly Glu Leu Asp Glu Leu Val Asp Lys Thr Arg Ile
            435                 440                 445

Ala Val Asp Arg Thr Ala Arg Gly Leu Gly Ile Leu
450                 455                 460

<210> SEQ ID NO 25
<211> LENGTH: 459
<212> TYPE: PRT
<213> ORGANISM: Pseudomonas putida
<220> FEATURE:
<223> OTHER INFORMATION: Strain KT2440

<400> SEQUENCE: 25

Met Ser Thr His Ser Ser Thr Val Gln Asn Asp Leu Ala Ala Leu Ile
1               5                   10                  15

His Pro Asn Thr Asn Leu Ala Gln His Arg Glu Val Gly Pro Leu Val
            20                  25                  30

Ile Ala Arg Gly Asp Gly Val Arg Val Phe Asp Glu Gln Gly Asn Ala
            35                  40                  45

Tyr Ile Glu Ala Met Ser Gly Leu Trp Ser Ala Ala Leu Gly Phe Ser
    50                  55                  60

Glu Gln Arg Leu Val Asp Ala Val Glu Gln Phe Lys Gln Leu Pro
65                  70                  75                  80

Tyr Tyr His Ser Phe Ser His Lys Thr Asn Ala Pro Ala Ala Leu
            85                  90                  95

Ala Ala Lys Leu Ala Ala Leu Ala Pro Gly Asp Leu Asn His Val Phe
            100                 105                 110

Phe Thr Asn Ser Gly Ser Glu Ala Asn Asp Ser Val Val Lys Met Val
            115                 120                 125

Trp Tyr Val Asn Asn Ala Leu Gly Arg Pro Ala Lys Lys Lys Phe Ile
130                 135                 140

Ser Arg Gln Gln Ala Tyr His Gly Ala Thr Val Ala Ala Ala Ser Leu
145                 150                 155                 160

Thr Gly Ile Pro Ser Met His Arg Asp Phe Asp Leu Pro Ala Ile Pro
            165                 170                 175

Val His His Leu Thr Cys Pro Asn Phe Tyr Arg Phe Ala Arg Pro Gly
            180                 185                 190

Glu Ser Gln Glu Ala Phe Thr Val Arg Leu Ala Asn Glu Leu Glu Arg
            195                 200                 205
```

Tyr Ile Leu Ala Glu Gly Pro Glu Thr Ile Ala Ala Phe Ile Gly Glu
            210                 215                 220

Pro Val Ile Ala Ala Gly Gly Val Ile Pro Pro Thr Gly Tyr Trp
225                 230                 235                 240

Ala Ala Ile Gln Ala Val Cys Lys Arg Tyr Asp Ile Leu Val Val Ile
            245                 250                 255

Asp Glu Ile Ile Thr Gly Phe Gly Arg Leu Gly Thr Met Phe Gly Ser
            260                 265                 270

Gln Leu Tyr Gly Ile Gln Pro Asp Ile Met Val Leu Ser Lys Gln Leu
            275                 280                 285

Thr Ser Ser Tyr Gln Pro Leu Ala Ala Val Val Ser Asp Ala Met
290                 295                 300

Asn Asp Val Leu Val Ser Gln Ser Gln Arg Leu Gly Ala Phe Ala His
305                 310                 315                 320

Gly Leu Thr Cys Thr Gly His Pro Val Ala Thr Ala Val Ala Leu Glu
            325                 330                 335

Asn Ile Arg Ile Ile Glu Glu Arg Asp Leu Val Gly His Val Gln His
            340                 345                 350

Leu Ala Pro Val Phe Gln Arg His Leu Arg Ala Phe Glu Asp His Pro
            355                 360                 365

Leu Val Gly Asn Val Arg Gly Val Gly Leu Met Gly Gly Ile Glu Leu
370                 375                 380

Val Ala Asp Lys Ala Thr Arg Gln Pro Phe Ala Gln Pro Gly Thr Leu
385                 390                 395                 400

Gly Gly Tyr Val Phe Lys Gln Ala His Lys His Gly Leu Ile Ile Arg
            405                 410                 415

Ala Ile Tyr Asp Thr Ile Ala Phe Cys Pro Pro Leu Ile Thr Thr Gln
            420                 425                 430

Asp Asp Ile Glu Ala Ile Phe Ser Ala Phe Glu Arg Thr Leu Ala Asp
            435                 440                 445

Ala Thr Asp Trp Ala Arg Ser Gln His Leu Leu
            450                 455

<210> SEQ ID NO 26
<211> LENGTH: 490
<212> TYPE: PRT
<213> ORGANISM: Pseudomonas putida
<220> FEATURE:
<223> OTHER INFORMATION: Strain W619

<400> SEQUENCE: 26

Met Arg Ile Ser Ser Val Ser Ser Ala Pro Gly Ser Val Ser Ser Cys
1               5                   10                  15

Cys Leu Leu Cys Asp Gln Pro Leu Arg Pro Pro Ala Gly Gly Leu Trp
            20                  25                  30

Thr Leu Glu Lys His Met Ser Val Lys Asn Pro Gln Thr Arg Asp Trp
        35                  40                  45

Gln Thr Leu Ser Gly Glu His His Leu Ala Pro Phe Ser Asp Tyr Lys
    50                  55                  60

Gln Leu Lys Glu Lys Gly Pro Arg Ile Ile Thr Lys Ala Gln Gly Val
65                  70                  75                  80

His Leu Trp Asp Ser Glu Gly His Lys Ile Leu Asp Gly Met Ala Gly
            85                  90                  95

Leu Trp Cys Val Ala Val Gly Tyr Gly Arg Glu Glu Leu Val Gln Ala
            100                 105                 110

```
Ala Glu Lys Gln Met Arg Glu Leu Pro Tyr Tyr Asn Leu Phe Phe Gln
        115                 120                 125

Thr Ala His Pro Pro Ala Leu Glu Leu Ala Lys Ala Ile Thr Asp Val
130                 135                 140

Ala Pro Glu Gly Met Thr His Val Phe Phe Thr Gly Ser Gly Ser Glu
145                 150                 155                 160

Gly Asn Asp Thr Val Leu Arg Met Val Arg His Tyr Trp Ala Leu Lys
                165                 170                 175

Gly Lys Pro Gln Lys Gln Thr Ile Ile Gly Arg Ile Asn Gly Tyr His
            180                 185                 190

Gly Ser Thr Val Ala Gly Ala Ser Leu Gly Gly Met Ser Gly Met His
        195                 200                 205

Glu Gln Gly Gly Leu Pro Ile Pro Gly Ile Val His Ile Pro Gln Pro
    210                 215                 220

Tyr Trp Phe Gly Glu Gly Gly Asp Met Ser Pro Asp Asp Phe Gly Val
225                 230                 235                 240

Trp Ala Ala Glu Gln Leu Glu Lys Lys Ile Leu Glu Val Gly Glu Asp
                245                 250                 255

Asn Val Ala Ala Phe Ile Ala Glu Pro Ile Gln Gly Ala Gly Gly Val
            260                 265                 270

Ile Ile Pro Pro Glu Thr Tyr Trp Pro Lys Val Lys Glu Ile Leu Ala
        275                 280                 285

Lys Tyr Asp Ile Leu Phe Val Ala Asp Glu Val Ile Cys Gly Phe Gly
    290                 295                 300

Arg Thr Gly Glu Trp Phe Gly Ser Asp Tyr Tyr Asp Leu Lys Pro Asp
305                 310                 315                 320

Leu Met Thr Ile Ala Lys Gly Leu Thr Ser Gly Tyr Ile Pro Met Gly
                325                 330                 335

Gly Val Ile Val Arg Asp Lys Val Ala Lys Val Leu Ser Glu Gly Gly
            340                 345                 350

Asp Phe Asn His Gly Phe Thr Tyr Ser Gly His Pro Val Ala Ala Ala
        355                 360                 365

Val Gly Leu Glu Asn Leu Arg Ile Leu Arg Glu Glu Lys Ile Val Glu
370                 375                 380

Lys Val Arg Thr Glu Val Ala Pro Tyr Leu Gln Lys Arg Leu Arg Glu
385                 390                 395                 400

Leu Gln Asp His Pro Leu Val Gly Glu Val Arg Gly Leu Gly Leu Leu
                405                 410                 415

Gly Ala Ile Glu Leu Val Lys Asp Lys Ala Ser Arg Ser Arg Tyr Glu
            420                 425                 430

Gly Lys Gly Val Gly Met Val Cys Arg Asn Phe Cys Phe Asp Asn Gly
        435                 440                 445

Leu Ile Met Arg Ala Val Gly Asp Thr Met Ile Ile Ala Pro Pro Leu
    450                 455                 460

Val Ile Ser His Ala Glu Val Asp Glu Leu Val Glu Lys Ala Arg Lys
465                 470                 475                 480

Cys Leu Asp Leu Thr Leu Glu Ala Ile Arg
                485                 490

<210> SEQ ID NO 27
<211> LENGTH: 457
<212> TYPE: PRT
<213> ORGANISM: Streptomyces coelicolor
<220> FEATURE:
<223> OTHER INFORMATION: Strain A3(2)
```

<400> SEQUENCE: 27

```
Met Ser Thr Asp Ser Pro Lys Asp Leu Ser Arg Thr Ala Tyr Asp His
1               5                   10                  15

Leu Trp Met His Phe Thr Arg Met Ser Ser Tyr Glu Asn Ala Pro Val
            20                  25                  30

Pro Thr Ile Val Arg Gly Glu Gly Thr His Ile Tyr Asp Asp Lys Gly
        35                  40                  45

Arg Arg Tyr Leu Asp Gly Leu Ala Gly Leu Phe Val Val Gln Ala Gly
    50                  55                  60

His Gly Arg Gln Glu Leu Ala Glu Thr Ala Ser Lys Gln Ala Gln Glu
65                  70                  75                  80

Leu Ala Phe Phe Pro Val Trp Ser Tyr Ala His Pro Lys Ala Val Glu
                85                  90                  95

Leu Ala Glu Arg Leu Ala Asn Glu Ala Pro Gly Asp Leu Asn Lys Val
            100                 105                 110

Phe Phe Thr Thr Gly Gly Gly Glu Ala Val Glu Thr Ala Trp Lys Leu
        115                 120                 125

Ala Lys Gln Tyr Phe Lys Leu Thr Gly Lys Pro Thr Lys Tyr Lys Val
    130                 135                 140

Ile Ser Arg Ala Val Ala Tyr His Gly Thr Pro Gln Gly Ala Leu Ser
145                 150                 155                 160

Ile Thr Gly Leu Pro Ala Leu Lys Ala Pro Phe Glu Pro Leu Val Pro
                165                 170                 175

Gly Ala His Lys Val Pro Asn Thr Asn Ile Tyr Arg Ala Pro Ile His
            180                 185                 190

Gly Asp Asp Pro Glu Ala Tyr Gly Arg Trp Ala Ala Asp Gln Ile Glu
        195                 200                 205

Gln Gln Ile Leu Phe Glu Gly Pro Glu Thr Val Ala Ala Val Phe Leu
    210                 215                 220

Glu Pro Val Gln Asn Ala Gly Gly Cys Phe Pro Pro Pro Gly Tyr
225                 230                 235                 240

Phe Gln Arg Val Arg Glu Ile Cys Asp Gln Tyr Asp Val Leu Leu Val
                245                 250                 255

Ser Asp Glu Val Ile Cys Ala Phe Gly Arg Leu Gly Thr Thr Phe Ala
            260                 265                 270

Cys Asp Lys Phe Gly Tyr Val Pro Asp Met Ile Thr Cys Ala Lys Gly
        275                 280                 285

Met Thr Ser Gly Tyr Ser Pro Ile Gly Ala Cys Val Ile Ser Asp Arg
    290                 295                 300

Leu Ala Glu Pro Phe Tyr Lys Gly Asp Asn Thr Phe Leu His Gly Tyr
305                 310                 315                 320

Thr Phe Gly Gly His Pro Val Ser Ala Ala Val Gly Ile Ala Asn Leu
                325                 330                 335

Asp Leu Phe Glu Arg Glu Gly Leu Asn Gln His Val Leu Asp Asn Glu
            340                 345                 350

Gly Ala Phe Arg Ala Thr Leu Glu Lys Leu His Asp Leu Pro Ile Val
        355                 360                 365

Gly Asp Val Arg Gly Asn Gly Phe Phe Tyr Gly Ile Glu Leu Val Lys
    370                 375                 380

Asp Lys Ala Thr Lys Glu Ser Phe Asp Glu Glu Thr Glu Arg Val
385                 390                 395                 400

Leu Tyr Gly Phe Leu Ser Lys Lys Leu Phe Glu Asn Gly Leu Tyr Cys
```

```
                    405                 410                 415
Arg Ala Asp Asp Arg Gly Asp Pro Val Ile Gln Leu Ala Pro Pro Leu
                420                 425                 430

Ile Ser Asn Gln Glu Thr Phe Asp Glu Ile Glu Gln Ile Leu Arg Ala
            435                 440                 445

Thr Leu Thr Glu Ala Trp Thr Lys Leu
        450                 455

<210> SEQ ID NO 28
<211> LENGTH: 459
<212> TYPE: PRT
<213> ORGANISM: Streptomyces avermitilis
<220> FEATURE:
<223> OTHER INFORMATION: Strain MA 4680

<400> SEQUENCE: 28

Met Gly Asn Pro Ile Ala Val Ser Lys Asp Leu Ser Arg Thr Ala Tyr
1               5                   10                  15

Asp His Leu Trp Met His Phe Thr Arg Met Ser Ser Tyr Glu Asn Ala
            20                  25                  30

Pro Val Pro Thr Ile Val Arg Gly Glu Gly Thr Tyr Ile Tyr Asp Asp
        35                  40                  45

Lys Gly Lys Arg Tyr Leu Asp Gly Leu Ser Gly Leu Phe Val Val Gln
    50                  55                  60

Ala Gly His Gly Arg Thr Glu Leu Ala Glu Thr Ala Phe Lys Gln Ala
65                  70                  75                  80

Gln Glu Leu Ala Phe Phe Pro Val Trp Ser Tyr Ala His Pro Lys Ala
                85                  90                  95

Val Glu Leu Ala Glu Arg Leu Ala Asn Tyr Ala Pro Gly Asp Leu Asn
            100                 105                 110

Lys Val Phe Phe Thr Thr Gly Gly Glu Ala Val Glu Thr Ala Trp
        115                 120                 125

Lys Leu Ala Lys Gln Tyr Phe Lys Leu Gln Gly Lys Pro Thr Lys Tyr
    130                 135                 140

Lys Val Ile Ser Arg Ala Val Ala Tyr His Gly Thr Pro Gln Gly Ala
145                 150                 155                 160

Leu Ser Ile Thr Gly Leu Pro Ala Leu Lys Ala Pro Phe Glu Pro Leu
                165                 170                 175

Val Pro Gly Ala His Lys Val Pro Asn Thr Asn Ile Tyr Arg Ala Pro
            180                 185                 190

Leu Phe Gly Asp Asp Pro Glu Ala Phe Gly Arg Trp Ala Ala Asp Gln
        195                 200                 205

Ile Glu Gln Gln Ile Leu Phe Glu Gly Pro Glu Thr Val Ala Ala Val
    210                 215                 220

Phe Leu Glu Pro Val Gln Asn Ala Gly Gly Cys Phe Pro Pro Pro
225                 230                 235                 240

Gly Tyr Phe Gln Arg Val Arg Glu Ile Cys Asp Gln Tyr Asp Val Leu
                245                 250                 255

Leu Val Ser Asp Glu Val Ile Cys Ala Phe Gly Arg Leu Gly Thr Met
            260                 265                 270

Phe Ala Cys Asp Lys Phe Gly Tyr Val Pro Asp Met Ile Thr Cys Ala
        275                 280                 285

Lys Gly Met Thr Ser Gly Tyr Ser Pro Ile Gly Ala Cys Ile Val Ser
    290                 295                 300

Asp Arg Ile Ala Glu Pro Phe Tyr Lys Gly Asp Asn Thr Phe Leu His
```

-continued

```
                305                 310                 315                 320
Gly Tyr Thr Phe Gly Gly His Pro Val Ser Ala Ala Val Gly Val Ala
                325                 330                 335

Asn Leu Asp Leu Phe Glu Arg Glu Gly Leu Asn Gln His Val Leu Asp
                340                 345                 350

Asn Glu Ser Ala Phe Leu Thr Thr Leu Gln Lys Leu His Asp Leu Pro
                355                 360                 365

Ile Val Gly Asp Val Arg Gly Asn Gly Phe Phe Tyr Gly Ile Glu Leu
                370                 375                 380

Val Lys Asp Lys Ala Thr Lys Glu Thr Phe Thr Asp Glu Glu Ser Glu
385                 390                 395                 400

Arg Val Leu Tyr Gly Phe Val Ser Lys Lys Leu Phe Glu Tyr Gly Leu
                405                 410                 415

Tyr Cys Arg Ala Asp Asp Arg Gly Asp Pro Val Ile Gln Leu Ser Pro
                420                 425                 430

Pro Leu Ile Ser Asn Gln Ser Thr Phe Asp Glu Ile Glu Ser Ile Ile
                435                 440                 445

Arg Gln Val Leu Thr Glu Ala Trp Thr Lys Leu
450                 455

<210> SEQ ID NO 29
<211> LENGTH: 450
<212> TYPE: PRT
<213> ORGANISM: Streptomyces avermitilis
<220> FEATURE:
<223> OTHER INFORMATION: Strain MA 4680

<400> SEQUENCE: 29

Met Thr Pro Gln Pro Asn Pro Gln Val Gly Ala Ala Val Lys Ala Ala
1               5                   10                  15

Asp Arg Ala His Val Phe His Ser Trp Ser Ala Gln Glu Leu Ile Asp
                20                  25                  30

Pro Leu Ala Val Ala Gly Ala Glu Gly Ser Tyr Phe Trp Asp Tyr Asp
                35                  40                  45

Gly Arg Arg Tyr Leu Asp Phe Thr Ser Gly Leu Val Phe Thr Asn Ile
                50                  55                  60

Gly Tyr Gln His Pro Lys Val Val Ala Ile Gln Glu Gln Ala Ala
65              70                  75                  80

Ser Leu Thr Thr Phe Ala Pro Ala Phe Ala Val Glu Ala Arg Ser Glu
                85                  90                  95

Ala Ala Arg Leu Ile Ala Glu Arg Thr Pro Gly Asp Leu Asp Lys Ile
                100                 105                 110

Phe Phe Thr Asn Gly Gly Ala Asp Ala Ile Glu His Ala Val Arg Met
                115                 120                 125

Ala Arg Ile His Thr Gly Arg Pro Lys Val Leu Ser Ala Tyr Arg Ser
                130                 135                 140

Tyr His Gly Gly Thr Gln Gln Ala Val Asn Ile Thr Gly Asp Pro Arg
145             150                 155                 160

Arg Trp Ala Ser Asp Ser Ala Ser Ala Gly Val Val His Phe Trp Ala
                165                 170                 175

Pro Tyr Leu Tyr Arg Ser Arg Phe Tyr Ala Glu Thr Glu Gln Gln Glu
                180                 185                 190

Cys Glu Arg Ala Leu Glu His Leu Glu Thr Thr Ile Ala Phe Glu Gly
                195                 200                 205

Pro Gly Thr Ile Ala Ala Ile Val Leu Glu Thr Val Pro Gly Thr Ala
```

```
                210                 215                 220
Gly Ile Met Val Pro Pro Gly Tyr Leu Ala Gly Val Arg Glu Leu
225                 230                 235                 240

Cys Asp Lys Tyr Gly Ile Val Phe Val Leu Asp Glu Val Met Ala Gly
                245                 250                 255

Phe Gly Arg Thr Gly Glu Trp Phe Ala Ala Asp Leu Phe Asp Val Thr
                260                 265                 270

Pro Asp Leu Met Thr Phe Ala Lys Gly Val Asn Ser Gly Tyr Val Pro
            275                 280                 285

Leu Gly Gly Val Ala Ile Ser Gly Lys Ile Ala Glu Thr Phe Gly Lys
        290                 295                 300

Arg Ala Tyr Pro Gly Gly Leu Thr Tyr Ser Gly His Pro Leu Ala Cys
305                 310                 315                 320

Ala Ala Ala Val Ala Thr Ile Asn Val Met Ala Glu Glu Gly Val Val
                325                 330                 335

Glu Asn Ala Ala Asn Leu Gly Ala Arg Val Ile Glu Pro Gly Leu Arg
                340                 345                 350

Glu Leu Ala Glu Arg His Pro Ser Val Gly Glu Val Arg Gly Val Gly
            355                 360                 365

Met Phe Trp Ala Leu Glu Leu Val Lys Asp Arg Glu Thr Arg Glu Pro
        370                 375                 380

Leu Val Pro Tyr Asn Ala Ala Gly Glu Ala Asn Ala Pro Met Ala Ala
385                 390                 395                 400

Phe Gly Ala Ala Ala Lys Ala Asn Gly Leu Trp Pro Phe Ile Asn Met
                405                 410                 415

Asn Arg Thr His Val Val Pro Pro Cys Asn Val Thr Glu Ala Glu Ala
                420                 425                 430

Lys Glu Gly Leu Ala Ala Leu Asp Ala Ala Leu Ser Val Ala Asp Glu
            435                 440                 445

Tyr Thr
    450

<210> SEQ ID NO 30
<211> LENGTH: 446
<212> TYPE: PRT
<213> ORGANISM: Chromobacterium violaceum
<220> FEATURE:
<223> OTHER INFORMATION: ATCC 12472

<400> SEQUENCE: 30

Met Asn His Pro Leu Thr Thr Arg Ser Glu Phe Asp His Leu Asp Leu
1               5                   10                  15

Arg Ala His Trp Met Pro Phe Ser Ala Asn Arg Asn Phe Gln Arg Asp
                20                  25                  30

Pro Arg Leu Ile Val Ser Gly Glu Gly Asn Tyr Leu Thr Asp Ala Asp
            35                  40                  45

Gly Arg Arg Ile Phe Asp Ser Leu Ser Gly Leu Trp Cys Cys Gly Ala
        50                  55                  60

Gly His Ser Arg Lys Glu Ile Ala Glu Ala Ala Tyr Arg Gln Leu Ser
65                  70                  75                  80

Thr Leu Asp Tyr Ser Pro Gly Phe Gln Phe Gly His Pro Leu Ser Phe
                85                  90                  95

Arg Leu Ala Glu Arg Val Ala Ala Met Ala Pro Gly Ala Leu Asn His
                100                 105                 110

Val Phe Phe Thr Asn Ser Gly Ser Glu Cys Ala Asp Thr Ala Val Lys
```

```
                    115                 120                 125
Met Ala Arg Ala Tyr Trp Arg Leu Lys Gly Gln Ala Ser Lys Thr Lys
    130                 135                 140

Leu Ile Gly Arg Ala Arg Gly Tyr His Gly Val Asn Ile Ala Gly Thr
145                 150                 155                 160

Ser Leu Gly Gly Met Asn Gly Asn Arg Lys Leu Phe Gly Pro Leu Met
                165                 170                 175

Asp Ala Asp His Leu Pro His Thr Leu Leu Pro Ala Asn Ala Phe Ser
            180                 185                 190

Arg Gly Leu Pro Glu Gln Gly Ala Glu Leu Ala Asp Asp Leu Leu Arg
        195                 200                 205

Leu Ile Glu Leu His Asp Ala Ser Asn Ile Ala Ala Val Ile Val Glu
    210                 215                 220

Pro Met Ala Gly Ser Ala Gly Val Ile Val Pro Pro Gln Gly Tyr Leu
225                 230                 235                 240

Gln Arg Leu Arg Glu Ile Cys Thr Gln His Gly Ile Leu Leu Ile Phe
                245                 250                 255

Asp Glu Val Ile Thr Gly Phe Gly Arg Thr Gly Ser Leu Phe Gly Ala
            260                 265                 270

Asp His Phe Gly Val Thr Pro Asp Ile Met Asn Leu Ala Lys Gln Leu
        275                 280                 285

Thr Asn Gly Ala Val Pro Met Gly Ala Val Val Ala Ser Ser Glu Ile
    290                 295                 300

Tyr Asp Ala Phe Met Ala Gln Ala Thr Pro Glu Tyr Ala Val Glu Phe
305                 310                 315                 320

Ala His Gly Tyr Thr Tyr Ser Ala His Pro Val Ala Cys Ala Ala Ala
                325                 330                 335

Leu Ala Ala Leu Asp Val Leu Glu Gln Glu Asn Leu Val Ala Arg Ala
            340                 345                 350

Ala Glu Leu Ala Pro His Phe Glu Arg Gly Ile His Gly Leu Lys Gly
        355                 360                 365

Leu Pro His Val Ile Asp Ile Arg Asn Cys Gly Leu Ala Gly Ala Val
    370                 375                 380

Gln Ile Ala Pro Ser Gly Asp Ala Ile Val Arg Pro Tyr Glu Ala
385                 390                 395                 400

Ala Met Ala Leu Trp Arg Lys Gly Phe Tyr Val Arg Tyr Gly Gly Asp
                405                 410                 415

Ala Leu Gln Phe Gly Pro Pro Phe Thr Ala Thr Pro Gln Glu Leu Asp
            420                 425                 430

Ser Leu Phe Asp Ala Val Gly Glu Thr Leu Ala Lys Leu Ala
        435                 440                 445

<210> SEQ ID NO 31
<211> LENGTH: 11539
<212> TYPE: DNA
<213> ORGANISM: Artificial Sequence
<220> FEATURE:
<223> OTHER INFORMATION: Description of Artificial Sequence: Synthetic
      vector polynucleotide

<400> SEQUENCE: 31
gaaaaccgcc actgcgccgt taccaccgct gcgttcggtc aaggttctgg accagttgcg     60
tgagcgcata cgctacttgc attacagttt acgaaccgaa caggcttatg tcaattcgcc    120
tctcaggcgc cgctggtgcc gctggttgga cgccaagggt gaatccgcct cgataccctg    180
```

-continued

```
attactcgct tcctgcgccc tctcaggcgg cgataggggg ctggtaaaac ggggattgcc      240
cagacgcctc ccccgcccct tcaggggcac aaatgcggcc ccaacggggc cacgtagtgg      300
tgcgtttttt gcgtttccac ccttttcttc cttttcccct ttaaacccttt taggacgtct     360 acaggccacg taatccgtgg cctgtagagt ttaaaaaggg acggatttgt tgccattaag      420
ggacggattt gttgttaaga agggacggat tgttgttgt aaagggacgg atttgttgta       480
ttgtgggacg cagatacagt gtccccttat acacaaggaa tgtcgaacgt ggcctcaccc      540
ccaatggttt acaaaagcaa tgccctggtc gaggccgcgt atcgcctcag tgttcaggaa      600
cagcggatcg ttctggcctg tattagccag gtgaagagga gcgagcctgt caccgatgaa     660
gtgatgtatt cagtgacggc ggaggacata gcgacgatgg cgggtgtccc tatcgaatct     720
tcctacaacc agctcaaaga gcggccctg cgcctgaaac ggcgggaagt ccggttaacc      780
caagagccca atggcaaggg gaaaagaccg agtgtgatga ttaccggctg ggtgcaaaca      840
atcatctacc gggagggtga gggccgtgta gaactcaggt tcaccaaaga catgctgccg      900
tacctgacgg aactcaccaa acagttcacc aaatacgcct ggctgacgt ggccaagatg       960 gacagcaccc acgcgatcag gctttacgag ctgctcatgc aatgggacag catcggccag     1020
cgcgaaatag aaattgacca gctgcgaaag tggtttcaac tggaaggccg gtatccctcg     1080
atcaaggact tcaagttgcg agtgcttgat ccagccgtga cgcagatcaa cgagcacagc     1140
ccgctacagg tggagtgggc gcagcgaaag accgggcgca aggtcacaca tctgttgttc      1200
agttttggac cgaagaagcc cgccaaggcg gtgggtaagg ccccagcgaa gcgcaaggcc     1260
gggaagattt cagatgctga gatcgcgaaa caggctcgcc ctggtgagac atgggaagcg     1320
gcccgcgctc gactaaccca gatgccgctg gatctggcct agaggccgtg gccaccacgg     1380
cccggcctgc ctttcaggct gcattattga agcatttatc agggttattg tctcatgagc     1440
ggatacatat ttgaatgtat ttagaaaaat aaacaaaaga gtttgtagaa acgcaaaaag      1500
gccatccgtc aggatggcct tctgcttaat ttgatgcctg gcagtttatg gcgggcgtcc     1560
tgcccgccac cctccgggcc gttgcttcgc aacgttcaaa tccgctcccg gcggatttgt     1620
cctactcagg agagcgttca ccgacaaaca acagataaaa cgaaaggccc agtctttcga     1680
ctgagccttt cgttttattt gatgcctggc agttccctac tctcgcatgg ggagacccca     1740
cactaccatc ggcgctacgg cgtttcactt ctgagttcgg catggggtca ggtgggacca     1800
ccgcgctact gccgccaggc aaattctgtt ttatcagacc gcttctgcgt tctgatttaa     1860
tctgtatcag gctgaaaatc ttctctcatc cgccaaaaca gaagcttggc tgcaggtcga     1920
caagcgctga atgggtatcg gcactagagt ttaacttggc taggctaatt ggtatggtca     1980 ttttatttt gtcctgaatt acctagaatg acttgaagtt ttaatcttca cttttcctcg     2040
tagagcacat agtcttcttt cgtagcccg caatccggac agcaccagtc atcaggaata      2100
tcctcaaagc gagtacctgg agtaaaaccc tcggcctcat cgcccaacgc tcatcatat      2160 atatggccac aagtaataca tatccacttc aagtatgctt tccgccttg ggcatcagac      2220 cttggaggtt gagttttata tagatcttgg cctttaacgt cggcactagg caatttctct     2280
aagcttgtcg gcgcaaccac tgcttcagca gttaaacttg tgccactaac ctcggataaa     2340
tttggcgaag tatgggttga ggtgacgccc ttttcaccta cgccgctctc aattaacatg      2400
aagtcaagct tgtctcgaac ggcgcaatcg gggcagcacc aatcctcagg aataaggtgc      2460
caaggcgtac ctggagaaaa cccctcatgc acattacccg cactctcatc ataaacataa      2520
ttacaatccg ggcatttata gctagccata ctcatcacca tgtcaaattg ttatttttgcg    2580
```

```
ttgcggcaaa tttgcgttat ttatttctca tcttcttcct tgtggaagat tttcttacaa    2640
cctgtggggt gctcgcctga tcaagaactt cagtcttagc cgcacagccc tcatttttat    2700
tttcttgatt aagtgggatc actaattctg cggccaaaac tgccattcca gttggagtag    2760
catctgaaat accactttcc gagttggcaa gctgactatt caccctagc tgtgtttctt     2820 tcgagggaga atccgcgaga aagataaagt ccaccttgtc tcgaactgcg cagtccgggc    2880
atgcccaatc tttggggata tcattccagc tggtgttcgg gtggaaacct tcgtgcggct    2940
cccccttatt ttcatcatag atatactgac aatctggaca ctggtaccttt gacattctcc   3000 cactctccta ttaactcagc gttagtcgct gctccgacaa cttcatcaga gtgtaactat    3060
cggagcaggt cgccttcaaa gcaattacag agaggcaatc aaccctcagc actttagcga    3120
agtgcactct ttgtgagagc tttcaacgcc gcacataaaa ttgaagcact tattgtaaat    3180
atcgaccgcc gggctctgcg tgctcacata actacgatgc taccgcagag gtactcgaac    3240
tatgaccagc actactagtg ccaaattttt tcaaataggt ttctcgcatc gaatcatcaa    3300
tttggatctt attaaggtca ccaccagccc aatctactac cttgggatcc ataactgatc    3360
taaaccactg aggaatcatc gccatcaaaa atgcaccagg gtaacccgtc ggaagagccg    3420
gcaggccggg aaaatcccga agtgactgat aagaacgtgt tggatgcgcg tggtgatccg    3480
agtgccgctg aaggtggaac agcactagat tagagacgat gtgattacta ttccaagaat    3540
ggtgcggctt ttgatgctca tatcgaccgt cctccatttt ttgacggagc aagccgtaat    3600
gttcaatata gttcgcactg gtcagctgcc accaaccgaa agccatttga atcggcagga    3660
acaccagcat cttaggtcca aacaaggcaa ggagaacggc gtaaagaata actgtgatga    3720
tcattggttg gaggatttca ttatcgaaac tccaaacgct ttggccacgg cgcgaaaggc    3780
gttgttcctc aagcccccaa gcacgaataa atgctcctgg gatctcacgg attgaaaact    3840
tataaatgct ttctcccatc cgggatgttg caggatccat cggtgtagcg acatcacggt    3900 gatgacccttt attatgctca ataaagaagt gaccgtaccc tacgacagcc aacacaattt    3960
tggccatcca acgatcaaaa gtctccttct tgtgaccgag ttcgtgtcct gtattgagcg    4020
ctagtccgtt cacgataccc agtgacaagg caagcgcacc aatttcaagc caagacattg    4080
gctgagttcc gacccaccat gctgacacaa ttaatgcagc gtaatgcata ggaactgtta    4140
gatatgtcaa aactcgatag taccgctcct tctctagttt cggcaccact tcttcaggcg    4200
gattattaaa gtcctcacca aacatcgcat caagcaatgg aagtgcgccg taccatacga    4260
gcaataccag cccataaaaa atcccccaac cagtttcatt tgcaagccag attccgatca    4320
tcggagtagc cggccacaaa gttgatagta tccagagata tttcttttta tctacgtact    4380
ctggagcgga atccagaact ctgtgtttct caagcatatg gaattctcca atttttatta    4440
aattagtcgc tacgagattt aagacgtaat tttatgccta actgagaaag ttaagccgcc    4500
cactctcact ctcgacatct taaacctgag ctaatcggac gcttgcgcca actacaccta    4560
cgggtagttt ttgctccgtc gtctgctgga aaaacacgag ctggccgcaa gcatgccagg    4620
taccgcgagc tactcgcgac ggctgaaagc accgaaatga gcgagctatc tggtcgattt    4680
tgacccggtg cccgtcttca aaatcggcga aggccgaagt cggccagaaa tagcggccta    4740
cttcagacct tccctagtaa atattttgca ccaccgatca tgccgactac acttaagtgt    4800
agttttaata tttaacaccg taacctatgg tgaaaatttc cagtcagctg gcgcgagaat    4860
agcataatga aaataataat aaataatgat ttcccggtcg ctaaggtcgg agcggatcaa    4920
```

```
attacgactc tagtaagtgc caaagttcat agttgcatat atcggccaag attgagtatc    4980
gcggatggag ccgctcccag agtatgcctt tacagagccc cacctggata tgggaaaacc    5040
gttgctcttg cgttcgagtg gctacgccac agaacagccg gacgtcctgc agtgtggctt    5100
tctttaagag ccagttctta cagtgaattt gatatctgcg cagagattat tgagcagctt    5160
gaaactttcg aaatggtaaa attcagccgt gtgagagagg gtgtgagcaa gcctgcgctc    5220
ttgcgagacc ttgcatctag tctttggcag agcacctcga ataacgagat agaaacgcta    5280
gtttgtttgg ataatattaa tcatgactta gacttgccgt tgttgcacgc acttatggag    5340
tttatgttaa atacaccaaa aaatatcagg tttgcagttg caggcaatac aataaaaggg    5400
ttctcgcagc ttaaacttgc aggcgctatg cgggagtaca ccgagaaaga cttggccttt    5460
agcgcagaag aggcggtggc gttagcggag gcagagtctg ttcttggagt tcctgaagaa    5520
cagatagaga ccttggtgca agaagttgag gggtggcctg ctcttgtagt ttttttgtta    5580
aagcgtgagt tgccggccaa gcatatttca gcagtagttg aagtagacaa ttactttagg    5640
gatgaaatat ttgaggcgat tcccgagcgc tatcgtgttt tcttgcaaa ttcttcattg     5700
ctcgatttcg tgacgcctga tcaatacaat tatgtattca aatgcgtcaa tggggtctca    5760
tgtattaagt atttaagcac taattacatg ttgcttcgcc atgtgagcgg tgagccagcg    5820
cagtttacac tgcatccagt actgcgtaat tttctacgag aaattacttg gactgaaaat    5880
cctgctaaaa gatcctacct gcttaagcgt gcagctttct ggcattggcg tagaggtgaa    5940
taccagtatg caatacgaat atccctacgg gcgaatgact gtcgctgggc agtcagcatg    6000
tctgagagaa taattttaga tttgtcattt cgtcagggcg aaatagatgc gctgagacag    6060
tggctgttag agctgccgaa gcaggcctgg caccaaaaac ccatagtgct tattagttac    6120
gcgtgggtat tgtatttcag tcagcaaggc gcgcgagcag agaagttaat taaagaccta    6180
tcttcacaat ccgataaaaa aaataaatgg caagaaaagg aatggctgca gcttgtgctt    6240
gcaataggta aagcaaccaa agatgaaatg ctttcgagtg aggagctctg taataagtgg    6300
attagtttat ttggggattc aaacgcagtt ggaaaagggg ccgcgctaac ctgtttggct    6360
tttattttg ccagtgagta tagatttgca gagttggaga aggtgctggc tcaggcccaa    6420
gccgtgaata aatttgcaaa acaaaatttt gcttttggtt ggctgtatgt cgcgaggttt    6480
caacaagccc tagcaagcgg aaaaatgggc tgggcgaggc agattataac tcaagcacgc    6540
acagacagtc gcgcgcagat gatggaatcc gagtttactt cgaaaatgtt tgacgctcta    6600
gagcttgagt tacattatga attgcgctgc ttggacacct cagaagaaaa gctctccaaa    6660
attttagagt tcatttccaa tcacggggtg acagacgtgt ttttttccgt atgccgtgct    6720
gtgtcagctt ggcggcttgg aaggagtgac ctaaatggct ccattgagat attggagtgg    6780
gcgaaggcgc atgcggttga aaaaaatcta ccaagattgg aagttatgag ccaaattgag    6840
atctatcagc gcttagtctg tcaaggcata acgggcataa ataatttaaa aactcttgaa    6900
gatcataaga ttttctccgg acagcactca gccccctaa aagcacgcct gctgcttgtt      6960
caatcactag tgctttcccg agatcggaac tttcatagtg ccgcgcacag agcgttattg    7020
gctattcagc aagcccgtaa aattaacgcg ggccagctgg aagtccgtgg attattgtgt    7080
ttggccggag cgcaggcagg tgccggtgat ttaaaaaagg ctcagcttaa cattgtttat    7140
gcagtggaga tagcaaaaca gcttcaatgc tttcaaacag ttcttgatga agtatgttta    7200
attgagcgaa taataccggc ttcatgtgaa gccttcacag cagttaattt agatcaagcg    7260
attggggctt ttagtcttcc gcgaatagtt gagattggaa agtccgcaga gaataaagct    7320
```

```
gacgctttat tgacacggaa gcagattgct gtcttgaggc ttgtaaaaga ggggtgctca    7380
aacaaacaaa tagcaacaaa tatgcatgtc accgaagatg ctataaagtg gcatatgagg    7440
aaaatatttg ccaccttgaa tgtagtgaat cgcacgcaag caacaattga agctgagcgt    7500
caaggaatta tctaaaataa tcggcattaa gtgatatagt gaaaagtata ccggagagag    7560
aattatggca atcgttgttg ttggcgctgg tacagctgga gtaaatgctg cgttctggct    7620
tcgtcaatat ggttataaag gggaaattag gattttttagc agggagtctg tggcgcctta    7680
tcagcggcct cctctatcca aggctttttct gacaagtgag attgcagaat ccgcagtgcc    7740
attaaagcca gaaggttttt atacgaataa caatattacc atttcgttaa atacaccgat    7800
tgtatcaatc gacgtggggc gtaagatagt ttcttctaaa gatggaaaag aatacgcgta    7860
tgaaaaattg attcttgcaa cacctgctag cgcacgtagg ttaacctgcg aggggtctga    7920
actgtctggg gtctgctatt tacgcagtat ggaagacgcc aaaaatttac gtaggaaact    7980
tgtggagagt gcgtctgttg ttgtgttggg cggcggagta atcgggcttg aagtcgcctc    8040
agctgcggtg ggcttaggga agagggtcac agtgatagaa gccacccgc gtgtaatggc    8100 gcgcgtggtt acgccggcag cagcaaactt agtcagagcc cgcctggagg ctgaaggaat    8160
tgagttcaag ctgaatgcga aattaacgtc tataaagggc aggaatggcc atgttgaaca    8220
atgcgtactt gaaagtggag aagaaattca ggcggatctg attgtagttg gaatcggtgc    8280
tatcccagag ctagagctgg caactgaggc ggcccttgaa gtgagtaatg tgttgtggt    8340 cgatgatcag atgtgtacat cggatacaag tatatatgca atcggcgact gcgcaatggc    8400
tagaaatcct ttttggggaa cgatggtacg tttagagaca attcataatg cggttacaca    8460
cgctcaaatt gtcgcaagta gcatctgtgg cacatcaaca ccagcaccaa ccccaccacg    8520
gttctggtct gatcttaaag ggatggcgct gcaaggactt ggtgctctaa aggactacga    8580
taaactcgtt gttgcaatta ataacgaaac tcttgaacta gaagtccttg cgtacaagca    8640
ggagcgactg attgcaactg agacaataaa tttgcctaaa cgtcaaggtg cgcttgcagg    8700
gagtataaaa ttacctgatt agcaatgatg ctcagccact cgaaccaacg gtcgcgatag    8760
ggacggcagt tacctgccgc cccccgcact ccgtacgtgc ggaactaccg cgtaaaatgt    8820
ggcccaggct gttatgtggc gcttgggcgg ggaagtattg ccatatttgg tgatgaccgt    8880
tttctacgcc acataaatcg gtggtggcta tggtgggatt tcccttgctg aaatgggaga    8940
tccgatcatg ttcgagctct tattcaaata cactgctgtg ttggcggtaa gcgttctcga    9000
gctcatagtc cacgacgccc gtgattttgt agccctggcc gacggccagc aggtaggccg    9060
acaggctcat gccggccgcc gccgcctttt cctcaatcgc tcttcgttcg tctggaaggc    9120
agtacacctt gataggtggg ctgcccttcc tggttggctt ggtttcatca gccatccgct    9180
tgccctcatc tgttacgccg gcggtagccg gccagcctcg cagagcagga ttcccgttga    9240
gcaccgccag gtgcgaataa gggacagtga agaaggaaca cccgctcgcg ggtgggccta    9300
cttcacctat cctgcccggc tgacgccgtt ggatacacca aggaaagtct acacgaaccc    9360
tttggcaaaa tcctgtatat cgtgcgaaaa aggatggata taccgaaaaa atcgctataa    9420
tgaccccgaa gcagggttat gcagcggaaa agcgctgctt ccctgctgtt ttgtggaata    9480
tctaccgact ggaaacaggc aaatgcagga aattactgaa ctgaggggac aggcgagaga    9540
ggatcaatgg ctatctgggg gaccgagggc tgtcgctgcg ccaaggcacg attggagatc    9600
ccctatgcgg tgtgaaatac cgcacagatg cgtaaggaga aaataccgca tcaggcgctc    9660
```

```
ttccgcttcc tcgctcactg actcgctgcg ctcggtcgtt cggctgcggc gagcggtatc    9720
agctcactca aaggcggtaa tacgttatc cacagaatca ggggataacg caggaaagaa     9780
catgtgagca aaaggccagc aaaaggccag gaaccgtaaa aaggccgcgt tgctggcgtt    9840
tttccatagg ctccgccccc ctgacgagca tcacaaaaat cgacgctcaa gtcagaggtg    9900
gcgaaacccg acaggactat aaagatacca ggcgtttccc cctggaagct ccctcgtgcg    9960
ctctcctgtt ccgaccctgc cgcttaccgg atacctgtcc gcctttctcc cttcgggaag    10020
cgtggcgctt tctcatagct cacgctgtag gtatctcagt tcggtgtagg tcgttcgctc    10080
caagctgggc tgtgtgcacg aaccccccgt tcagcccgac cgctgcgcct tatccggtaa    10140
ctatcgtctt gagtccaacc cggtaagaca cgacttatcg ccactggcag cagccactgg    10200
taacaggatt agcagagcga gtatgtagg cggtgctaca gagttcttga agtggtggcc      10260
taactacggc tacactagaa ggacagtatt tggtatctgc gctctgctga agccagttac    10320
cttcggaaaa agagttggta gctcttgatc cggcaaacaa accaccgctg gtagcggtgg    10380
tttttttgtt tgcaagcagc agattacgcg cagaaaaaaa ggatctcaag aagatccttt    10440
gatcttttct acggggtctg acgctcagtg gaacgaaaac tcacgttaag ggattttggt    10500
catgagatta tcaaaaagga tcttcaccta gatccttta aattaaaaat gaagttttaa     10560
atcaatctaa agtatatatg agtaaacttg gtctgacagt taccaatcga ttggtcggtc    10620
atttcgaacc ccagagtccc gctcagaaga actcgtcaag aaggcgatag aaggcgatgc    10680
gctgcgaatc gggagcggcg ataccgtaaa gcacgaggaa gcggtcagcc cattcgccgc    10740
caagctcttc agcaatatca cgggtagcca acgctatgtc ctgatagcgg tccgccacac    10800
ccagccggcc acagtcgatg aatccagaaa agcggccatt ttccaccatg atattcggca    10860
agcaggcatc gccatgggtc acgacgagat cctcgccgtc gggcatgcgc gccttgagcc    10920
tggcgaacag ttcggctggc gcgagcccct gatgctcttc gtccagatca tcctgatcga    10980
caagaccggc ttccatccga gtacgtgctc gctcgatgcg atgtttcgct tggtggtcga    11040
atgggcaggt agccggatca agcgtatgca gccgccgcat tgcatcagcc atgatggata    11100
ctttctcggc aggagcaagg tgagatgaca ggagatcctg ccccggcact cgcccaata     11160 gcagccagtc ccttcccgct tcagtgacaa cgtcgagcac agctgcgcaa ggaacgcccg    11220
tcgtggccag ccacgatagc cgcgctgcct cgtcctgcag ttcattcagg gcaccggaca    11280
ggtcggtctt gacaaaaaga accgggcgcc cctgcgctga cagccggaac acggcggcat    11340
cagagcagcc gattgtctgt tgtgcccagt catagccgaa tagcctctcc acccaagcgg    11400
ccggagaacc tgcgtgcaat ccatcttgtt caatcatgcg aaacgatcct catcctgtct    11460
cttgatcaga tcttgatccc ctgcgccatc agatccttgg cggcaagaaa gccatccagt    11520
ttactttgca gggcttccc                                                 11539
```

```
<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aagggaattc catatgcttg agaaacacag agttc                               35

<210> SEQ ID NO 33
```

```
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aaaattcgcg tcgacaagcg ctgaatgggt atcgg                                35

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tgagacagtg gctgttagag                                                 20

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
taataaccgc tcgagaacgc ttaccgccaa cacag                                35

<210> SEQ ID NO 36
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gccggcgaga acctgtactt tcagatggca agtaagtatg ccacttg                   47

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggatcctcac ttcttgtgct gagccttg                                        28

<210> SEQ ID NO 38
<211> LENGTH: 446
<212> TYPE: PRT
<213> ORGANISM: Arabidopsis thaliana

<400> SEQUENCE: 38

Met Val Val Ile Asn Ser Leu Arg Arg Leu Ala Arg Thr Thr Gln Val
1               5                   10                  15

His Leu His Ser Lys Tyr Ala Thr Cys Met Ser Gly Asn Ser Thr Ser
                20                  25                  30

Arg Arg Ile Phe Thr Thr Glu Ala Ala Pro Glu Lys Gly Asn Glu Pro
        35                  40                  45
```

-continued

Arg Leu Val Ser Ala Val Glu Gln Leu Asn Thr Leu Pro Phe Tyr
    50                  55                  60

His Ser Phe Trp Asn Arg Thr Thr Lys Pro Ser Leu Asp Leu Ala Lys
65                  70                  75                  80

Val Leu Leu Glu Met Phe Thr Ala Asn Lys Met Ala Lys Ala Phe Phe
                85                  90                  95

Thr Ser Gly Gly Ser Asp Ala Asn Asp Thr Gln Val Lys Leu Val Trp
            100                 105                 110

Tyr Tyr Asn Asn Ala Leu Gly Arg Pro Glu Lys Lys Phe Ile Ala
        115                 120                 125

Arg Lys Lys Ser Tyr His Gly Ser Thr Leu Ile Ser Ala Ser Leu Ser
130                 135                 140

Gly Leu Pro Pro Leu His Gln Asn Phe Asp Leu Pro Ala Pro Phe Val
145                 150                 155                 160

Leu His Thr Asp Cys Pro His Tyr Trp Arg Phe His Leu Pro Gly Glu
                165                 170                 175

Thr Glu Glu Glu Phe Ser Thr Arg Leu Ala Lys Asn Leu Glu Asp Leu
            180                 185                 190

Ile Ile Lys Glu Gly Pro Glu Thr Ile Gly Ala Phe Ile Ala Glu Pro
        195                 200                 205

Val Met Gly Ala Gly Gly Val Ile Pro Pro Ala Thr Tyr Phe Glu
210                 215                 220

Lys Val Gln Ala Val Val Lys Lys Tyr Asp Ile Leu Phe Ile Ala Asp
225                 230                 235                 240

Glu Val Ile Cys Ala Phe Gly Arg Leu Gly Thr Met Phe Gly Cys Asp
                245                 250                 255

Lys Tyr Asn Ile Lys Pro Asp Leu Val Thr Leu Ala Lys Ala Leu Ser
            260                 265                 270

Ser Ala Tyr Met Pro Ile Gly Ala Ile Leu Met Ser Gln Glu Val Ala
        275                 280                 285

Asp Val Ile Asn Ser His Ser Ser Lys Leu Gly Val Phe Ser His Gly
290                 295                 300

Phe Thr Tyr Ser Gly His Pro Val Ser Cys Ala Val Ala Ile Glu Ala
305                 310                 315                 320

Leu Lys Ile Tyr Lys Glu Arg Asn Ile Pro Glu Tyr Val Ala Lys Val
                325                 330                 335

Ala Pro Arg Phe Gln Asp Gly Val Lys Ala Phe Ala Ser Gly Ser Pro
            340                 345                 350

Ile Ile Gly Glu Thr Arg Gly Thr Gly Leu Ile Leu Gly Thr Glu Phe
        355                 360                 365

Val Asp Asn Lys Ser Pro Asn Glu Pro Phe Pro Glu Trp Gly Val
370                 375                 380

Gly Ala Phe Phe Gly Ala Glu Cys Gln Lys His Gly Met Leu Val Arg
385                 390                 395                 400

Val Ala Gly Asp Gly Ile Leu Met Ser Pro Pro Leu Ile Ile Ser Pro
                405                 410                 415

Glu Glu Ile Asp Glu Leu Ile Ser Ile Tyr Gly Lys Ala Leu Lys Ala
            420                 425                 430

Thr Glu Glu Lys Val Lys Glu Leu Lys Ala Gln His Lys Lys
        435                 440                 445

<210> SEQ ID NO 39
<211> LENGTH: 1515

```
<212> TYPE: DNA
<213> ORGANISM: Arabidopsis thaliana

<400> SEQUENCE: 39
atggtcgtta tcaacagtct ccgacgcttg gcgcgtacca ctcaggttca tttgcacagt      60
aagtatgcca cttgcatgtc tgggaactcc acttccagga ggattttcac tactgaggca     120
gcacctgaga agaaaaacac tgttgggtct aaagggcatg atatgcttgc accttttact     180
gctggatggc agagtgctga tttagatccc ttggtcattg caaagtctga gggaagttat     240
gtgtatgatg atactgggaa aaaatatctt gactctctcg ctggtttatg gtgtactgcc     300
ttaggaggaa atgagccaag gcttgtttct gccgctgttg aacagttgaa caccttgccg     360
ttttatcact cctttggaa ccgtactact aaaccttctc tggatcttgc taaggttctt      420
ttagagatgt tcacggccaa caaaatggcc aaagcatttt ttacaagcgg tggatcagat     480
gccaacgata cccaggtcaa gctggtttgg tattacaata cgcacttgg aaggcccgag      540 aagaaaaagt ttatcgcgag aaagaaatcg taccatggct ccactctaat atcagcaagt     600
ttgtccggcc ttccccgct acaccaaaat tttgatttac ctgcaccatt tgtgttgcac      660
acagattgcc ctcattattg cgttttcat cttccaggcg aaacggaaga ggagttctca      720
accagattag ccaagaattt agaggatcta atcatcaaag aaggaccaga aactattggt     780
gcttttatag ctgaaccagt catgggtgct ggggtgtga tacctccacc tgctacctac      840
tttgaaaagg ttcaagctgt tgttaagaaa tatgatatct tgttcattgc tgatgaggtg     900
atatgtgcat ttggaaggct cgggacaatg tttggctgtg acaaatacaa cattaagcca     960
gatcttgtga ccttagctaa ggcactgtct tcagcatata tgccgattgg agccattctt    1020
atgagccaag aagtggcaga tgtcataaat tctcatagca gcaagctagg cgttttctcc    1080
catggattta cttattctgg tcatccagtt tcgtgtgctg tagcaattga agcgttaaag    1140
atatacaagg agaggaacat accagagtat gtcgccaaag ttgccccaag gtttcaagat    1200
ggagttaaag cgtttgcctc tggtagtcct attattggag agacaagagg aacaggtttg    1260
attcttggga ctgagtttgt agacaataaa tctccgaacg aaccatttcc accagaatgg    1320
ggtgttggcg cattctttgg agccgagtgc cagaagcacg gatgttagt ccgtgttgca     1380 ggtgatggca ttttgatgtc tccaccgctc attatctcac ctgaagagat tgatgagttg    1440
atttctatct atgggaaagc attgaaggca acggaagaga aggtaaaaga actcaaggct    1500
cagcacaaga agtga                                                     1515

<210> SEQ ID NO 40
<211> LENGTH: 1362
<212> TYPE: DNA
<213> ORGANISM: Pseudomonas sp.

<400> SEQUENCE: 40
atgagcgtca caacccgca aaccgtgaa tggcaaaccc tgagcgggga gcaccatctc        60
gcacctttca gtgactacaa gcagctgaag gagaaggggc gcgcatcat caccaaggcc     120 caggggggtgc atttgtggga cagcgagggg cacaagatcc tcgacggcat ggcgggcctg    180
tggtgcgtgg cggtgggtta cggccgtgaa gagctggttc aggcagcaga aaagcagatg    240
cgcgagctgc cgtactacaa cctgttcttc cagacggccc accgcctgc actggaactg     300 gccaaggcca ttaccgatgt ggcgcccgag gcatgaccc atgtgttctt caccggctcc    360
ggctccgaag gcaacgacac cgtgctgcgc atggtgcgcc actactgggc gttgaagggc    420
```

```
aagccgcaca agcagaccat catcggccgt atcaacggct accacggctc caccttcgcc    480
ggtgcttgcc tgggcggcat gagcggcatg cacgagcagg gcggcctgcc gatcccgggc    540
atcgtgcaca tcccgcagcc gtactggttc ggcgaaggcg gtgacatgac cccggatgcg    600
ttcggtatct gggcggccga acagctggag aagaaaatcc tcgaagtcgg cgaagacaac    660
gtcgccgcct tcatcgccga gcctatccag ggcgcaggcg gcgtgatcat cccgccggaa    720
acctactggc cgaaggtgaa ggagattctc gccaagtacg acatcctgtt cgttgccgac    780
gaagtcatct gtggtttcgg ccgtaccggc gagtggttcg gctctgatta ctacgacctc    840
aagcccgacc tgatgaccat cgccaagggc ctgacctccg gttacatccc catgggcggt    900
gtgatcgtgc gtgacaaagt ggccaaggtg atcagcgaag gcggtgactt caaccacggc    960
ttcacctatt cgggccaccc ggtagccggc gcggtgggcc tggaaaacct gcgcatcctg   1020
cgcgacgagc aaattgtcga aggcgcgt actgaagcgg caccgtattt gcaaaagcgt     1080
ttgcgtgagc tgcaggacca cccgctggtg ggtgaagtgc gcggccttgg catgcttggc   1140
gcgatcgagc tggtgaaaga caaggccacc cgcagccgtt acgagggcaa gggcgtgggc   1200
atgatctgcc gcaccttctg cttcgaaaac ggcctgatca tgcgtgcggt gggtgacacc   1260
atgatcatcg cgccgccgct ggtcatcagc catgcggaaa tcgacgaact ggtggaaaag   1320
gcacgcaaat gcctcgacct gacccttgag gcgattcgat aa                      1362
```

<210> SEQ ID NO 41
<211> LENGTH: 1359
<212> TYPE: DNA
<213> ORGANISM: Pseudomonas sp.

<400> SEQUENCE: 41

```
atgagcgatt cgcaaaccct gcactggcaa gcgctgagcc gcgaccatca tctgccgccg     60
ttcaccgatt acaaggcgct gaacgccaaa ggcacgcgca tcatcaccaa ggcgtcaggc    120
gtctacctgt gggacagcga aggcacaag atcctcgacg ccatggccgg gctctggtgc     180
gtcaacctgg gctatggccg cgaggagctg gtcgaggccg cgaccaggca gatgcgcgag    240
ctgccgtact acaacctgtt cttccagacc gcccacccgc cggccgtggc gctggccaag    300
gcgattgccg acatcgcgcc ggccgggatg aaccatgtgt tcttcaccgg ctccggctcg    360
gaggccaacg acaccgtgct gcgcatggtg cgccattact gggcgatcaa gggccagccg    420
gcgaagaagg tggtcatcgg ccgctggaat ggctatcacg gctcgaccat cgctggcgca    480
agcctcggtg gcatgaaggc catgcacgag cagggcgacg gcccgatccc ggcatcgag    540
catatcgacc agccctactg gttcggcgag ggtggcgaca tgagcccgga agagttcggc    600
gtgcgcatcg ccgaccagct ggagcagaag atccttgagg tcggcgagga caaggtcgcc    660
gccttcatcg ccgaacctat ccagggcgcc ggcggcgtga tcatcccgcc cgagagctac    720
tggccgcggg tcaaggaaat cctcgcgcgc tacgacattc tcttcatcgc cgacgaggtc    780
atctgcggct tcggccgtac cggtgagtgg ttcggcagca actactacgg cctcgagccg    840
gacctgatgc cgatcgccaa gggcctgacc tctggctaca tccccatggg cggcgtagtg    900
gtgcgcgacg aagtggtgca cacgctcaac gagggcggca gttctacca cggcttcacc    960
tactcggggc acccgtggc cgccgcggtg cgctggaga acatccgcat cctgcgcgag    1020
gagaagatcg tcgagcgggt gaagacgaag acggcaccct atttgcagtc ccgttggcag   1080
gaactgctcg agcatccgct ggtaggcgag gcgcgcggc tcggcctgct tggtgcgctg    1140
gagttggtga agaacaagaa gacccgcgaa cgctttgccg atcccggtgt gggcatgctc   1200
```

```
tgtcgcgagc actgcttccg caacggcctg gtgatgcgtg cggttggcga caccatgatc    1260
atttcgccgc cgctggtgat cagcgaagag cagatcgacg agctggttgg caaggtgcgg    1320
ttgtgcctcg acgccacggc caaggatgtg ctgggctga                           1359
```

<210> SEQ ID NO 42
<211> LENGTH: 1380
<212> TYPE: DNA
<213> ORGANISM: Artificial Sequence
<220> FEATURE:
<223> OTHER INFORMATION: Description of Artificial Sequence: Synthetic
    codon optimized gene for expression in E. coli

<400> SEQUENCE: 42

```
atgcagaaac agcgtaccac ctctcagtgg cgtgaactgg atgcggcgca tcatctgcat     60
ccgtttaccg ataccgcgag cctgaatcag gcgggtgcgc gtgtgatgac ccgtggcgaa    120
ggcgtgtatc tgtgggatag cgaaggcaac aaaattattg atggcatggc gggcctgtgg    180
tgcgtgaacg tgggctatgg ccgtaaagat tttgcggaag cggcgcgtcg tcagatggaa    240
gaactgccgt tttataacac cttctttaaa accacccatc cggcggtggt ggaactgagc    300
agcctgctgg ccgaagttac cccggcaggt tttgatcgtg tgttttatac caacagcggc    360
agcgaaagcg tggataccat gattcgtatg gtgcgtcgtt attgggatgt gcagggcaaa    420
ccggaaaaaa aaaccctgat tggccgttgg aacggctatc acggcagcac cattggcggt    480
gcgagcctgg gcggcatgaa atatatgcat gaacagggcg atctgccgat tccgggcatg    540
gcgcatattg aacagccgtg gtggtataaa catggcaaag atatgacccc ggatgaattt    600
ggcgtggttg cggcgcgttg gctggaagaa aaaattctgg aaatcggcgc ggataaagtg    660
gcggcgtttg tgggcgaacc gattcagggt gcgggcggtg tgattgttcc gccggcaacc    720
tattggccgg aaattgaacg tatttgccgc aaatatgatg tgctgctggt gcggatgaa     780 gtgatttgcg gctttggccg taccggcgaa tggtttggcc atcagcattt ggcttcag     840 ccggacctgt ttaccgcggc gaaaggcctg agcagcggct atctgccgat tggcgcggtg    900
tttgtgggca acgtgttgc ggaaggtctg attgcgggcg tgattttaa ccatggcttt     960 acctatagcg ccatccggt gtgtgcggcg gtggcgcatg cgaatgttgc ggcgctgcgt    1020
gatgaaggca ttgtgcagcg tgtgaaagat gatattggcc cgtatatgca gaaacgttgg    1080
cgtgaaacct ttagccgttt tgaacatgtg gatgatgtgc gtggcgtggg catggtgcag    1140
gcgtttaccc tggtgaaaaa caaagcgaaa cgtgaactgt ttccggattt tggcgaaatt    1200
ggcaccctgt gccgcgatat ttttttttcgc aacaacctga ttatgcgtgc gtgcggcgat    1260
cacattgtgt ctgcaccgcc gctggttatg acccgtgcgg aagtggatga atgctggcc    1320 gtggcggaac gttgcctgga agaatttgaa cagaccctga aagcgcgtgg cctggcctaa    1380
```

<210> SEQ ID NO 43
<211> LENGTH: 5143
<212> TYPE: DNA
<213> ORGANISM: Artificial Sequence
<220> FEATURE:
<223> OTHER INFORMATION: Description of Artificial Sequence: Synthetic
    vector polynucleotide

<400> SEQUENCE: 43

```
tttaagaagg agatataccc atgacacaga gggcccacca tcaccatcac cattccatgg     60
cctcctccga ggacgtcatc aaggagttca tgcgcttcaa ggtgcgcatg gagggctccg    120
```

-continued

```
tgaacggcca cgagttcgag atcgagggcg agggcgaggg ccgcccctac gagggcaccc    180
agaccgccaa gctgaaggtg accaagggcg gcccctgcc cttcgcctgg acatcctgt     240 cccctcagtt ccagtacggc tccaaggcct acgtgaagca cccccgccgac atccccgact    300 acttgaagct gtccttcccc gagggcttca agtgggagcg cgtgatgaac ttcgaggacg    360
gcggcgtggt gaccgtgacc caggactcct ccctgcagga cggcgagttc atctacaagg    420
tgaagctgcg cggcaccaac ttcccctccg acggccccgt aatgcagaag aagactatgg    480
gttgggaggc ctccaccgag cggatgtacc ccgaggacgc cgccctgaag ggcgagatca    540
agatgaggct gaagctgaag gacggcggcc actacgacgc cgaggtcaag accacctaca    600
tggccaagaa gccgtgcag ctgccggcg cctacaagac cgacatcaag ctggacatca    660
cctcccacaa cgaggactac accatcgtgg aacagtacga gcgcgccgag ggccgccact    720
ccaccggcgc cggcgagaac ctgtactttc agatggcaag taagtatgcc acttgcatgt    780 ctggaactc cacttccagg aggattttca ctactgaggc agcacctgag aagaaaaaca    840
ctgttgggtc taaagggcat gatatgcttg caccttttac tgctggatgg cagagtgctg    900
atttagatcc cttggtcatt gcaaagtctg agggaagtta tgtgtatgat gatactggga    960
aaaaatatct tgactctctc gctggtttat ggtgtactgc cttaggagga aatgagccaa   1020
ggcttgtttc tgccgctgtt gaacagttga cacccttgcc gttttatcac tccttttgga   1080
accgtactac taaaccttct ctggatcttg ctaaggttct tttagagatg ttcacggcca   1140
acaaaatggc caaagcattt tttacaagcg gtggatcaga tgccaacgat acccaggtca   1200
agctggtttg gtattacaat aacgcacttg gaaggcccga gaagaaaaag tttatcgcga   1260
gaaagaaatc gtaccatggc tccactctaa tatcagcaag tttgtccggc cttccccgc    1320 tacaccaaaa ttttgattta cctgcaccat ttgtgttgca cacagattgc cctcattatt   1380
ggcgttttca tcttccaggc gaaacggaag aggagttctc aaccagatta gccaagaatt   1440
tagaggatct aatcatcaaa gaaggaccag aaactattgg tgcttttata gctgaaccag   1500
tcatgggtgc tgggggtgtg atacctccac ctgctaccta ctttgaaaag gttcaagctg   1560
ttgttaagaa atatgatatc ttgttcattg ctgatgaggt gatatgtgca tttggaaggc   1620
tcgggacaat gtttggctgt gacaaataca acattaagcc agatcttgtg accttagcta   1680
aggcactgtc ttcagcatat atgccgattg gagccattct tatgagccaa gaagtggcag   1740
atgtcataaa ttctcatagc agcaagctag gcgttttctc ccatggattt acttattctg   1800
gtcatccagt ttcgtgtgct gtagcaattg aagcgttaaa gatatacaag gagaggaaca   1860
taccagagta tgtcgccaaa gttgccccaa ggtttcaaga tggagttaaa gcgtttgcct   1920
ctggtagtcc tattattgga gagacaagag gaacaggttt gattcttggg actgagtttg   1980
tagacaataa atctccgaac gaaccatttc caccagaatg gggtgttggc gcattctttg   2040
gagccgagtg ccagaagcac gggatgttag tccgtgttgc aggtgatggc attttgatgt   2100
ctccaccgct cattatctca cctgaagaga ttgatgagtt gatttctatc tatgggaaag   2160
cattgaaggc aacggaagag aaggtaaaag aactcaaggc tcagcacaag aagtgaggat   2220
ccggctgcta acaaagcccg aaaggaagct gagttggctg ctgccaccgc tgagcaataa   2280
ctagcataac cccttggggc ctctaaacgg gtcttgaggg gttttttgct gaaaggagga   2340
actatatccg gccggatatc cacaggacgg gtgtggtcgc catgatcgcg tagtcgatag   2400
tggctccaag tagcgaagcg agcaggactg ggcggcggcc aaagcggtcg acagtgctc    2460 cgagaacggg tgcgcataga aattgcatca acgcatatag cgctagcagc acgccatagt   2520
```

```
gactggcgat gctgtcggaa tggacgatat cccgcaagag gcccggcagt accggcataa    2580
ccaagcctat gcctacagca tccagggtga cggtgccgag gatgacgatg agcgcattgt    2640
tagatttcat acacggtgcc tgactgcgtt agcaatttaa ctgtgataaa ctaccgcatt    2700
aaagcttatc gatgataagc tgtcaaacat gagaattctt gaagacgaaa gggcctcgtg    2760
atacgcctat ttttataggt taatgtcatg catgagacaa taaccctgat aaatgcttca    2820
ataatattga aaaggaaga gtatgagtat tcaacatttc cgtgtcgccc ttattccctt    2880
ttttgcggca ttttgccttc ctgttttgc tcacccagaa acgctggtga agtaaaaga    2940 tgctgaagat cagttgggtg cacgagtggg ttacatcgaa ctggatctca acagcggtaa    3000
gatccttgag agttttcgcc ccgaagaacg ttttccaatg atgagcactt ttaaagttct    3060
gctatgtggc gcggtattat cccgtgttga cgccgggcaa gagcaactcg gtcgccgcat    3120
acactattct cagaatgact tggttgacgc gtcaccagtc acagaaaagc atcttacgga    3180
tggcatgaca gtaagagaat tatgcagtgc tgccataacc atgagtgata acactgcggc    3240
caacttactt ctgacaacga tcggaggacc gaaggagcta accgcttttt tgcacaacat    3300
gggggatcat gtaactcgcc ttgatcgttg ggaaccggag ctgaatgaag ccataccaaa    3360
cgacgagcgt gacaccacga tgcctgcagc aatggcaaca acgttgcgca aactattaac    3420
tggcgaacta cttactctag cttcccggca acaattaata gactggatgg aggcggataa    3480
agttgcagga ccacttctgc gctcggccct tccggctggc tggtttattg ctgataaatc    3540
tggagccggt gagcgtgggt ctcgcggtat cattgcagca ctggggccag atggtaagcc    3600
ctcccgtatc gtagttatct acacgacggg gagtcaggca actatggatg aacgaaatag    3660
acagatcgct gagataggtg cctcactgat taagcattgg taactgtcag accaagttta    3720
ctcatatata ctttagattg atttaaaact tcatttttaa tttaaaagga tctaggtgaa    3780
gatccttttt gataatctca tgcatgacca aaatcccta acgtgagttt tcgttccact    3840
gagcgtcaga ccccgtagaa aagatcaaag gatcttcttg agatccttt tttctgcgcg    3900 taatctgctg cttgcaaaca aaaaaaccac cgctaccagc ggtggtttgt ttgccggatc    3960
aagagctacc aactctttt ccgaaggtaa ctggcttcag cagagcgcag ataccaaata    4020
ctgtccttct agtgtagccg tagttaggcc accacttcaa gaactctgta gcaccgccta    4080
catacctcgc tctgctaatc ctgttaccag tggctgctgc cagtggcgat aagtcgtgtc    4140
ttaccgggtt ggactcaaga cgatagttac cggataaggc gcagcggtcg ggctgaacgg    4200
ggggttcgtg cacacagccc agcttggagc gaacgaccta caccgaactg agatacctac    4260
agcgtgagct atgagaaagc gccacgcttc ccgaagggag aaaggcggac aggtatccgg    4320
taagcggcag ggtcggaaca ggagagcgca cgagggagct tccagggga aacgcctggt    4380 atctttatag tcctgtcggg tttcgccacc tctgacttga gcgtcgattt tgtgatgct    4440 cgtcaggggg gcggagccta tggaaaaacg ccagcaacgc ggcctttta cggttcctgg    4500 ccttttgctg gccttttgct cacatgttct ttcctgcgtt atcccctgat tctgtggata    4560
accgtattac cgcctttgag tgagctgata ccgctcgccg cagccgaacg accgagcgca    4620
gcgagtcagt gagcgaggaa gcggaagagc gcctgatgcg gtattttctc cttacgcatc    4680
tgtgcggtat ttcacaccgc atatatggtg cactctcagt acaatctgct ctgatgccgc    4740
atagttaagc cagtatacac tccgctatcg ctacgtgact gggtcatggc tgcgccccga    4800
cacccgccaa cacccgctga cgcgccctga cgggcttgtc tgctcccggc atccgcttac    4860
```

```
agacaagctg tgaccgtctc cgggagctgc atgtgtcaga ggttttcacc gtcatcaccg    4920
aaacgcgcga ggcagctggc acgacaggtt tcccgactgg aaagcgggca gtgagcgcaa    4980
cgcaattaat gtgagttagc tcactcatta ggcaccccag gctttacact ttatgcttcc    5040
ggctcgtatg ttgtgtggaa ttgtgagcgg ataacaattt cacacaggaa acagctatga    5100
ccatgattac gccaagctct agctagaaat aattttgttt aac                     5143
```

```
<210> SEQ ID NO 44
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ggaattccat atgagcgtca acaacccgca aacccg                              36

<210> SEQ ID NO 45
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccgctcgagt tatcgaatcg cctcaagggt caggtcc                             37

<210> SEQ ID NO 46
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggaattccat atgagcgatt cgcaaaccct gcactggc                            38

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cgcggatcct cagcccagca catccttggc tgtcg                               35

<210> SEQ ID NO 48
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aacaaaaggg ccgcaatggc catgggtgtg tatgactac                           39

<210> SEQ ID NO 49
<211> LENGTH: 37
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 49
tacaggggcc accacggcct caggcgatca caattcc                              37

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 50

His His His His His His
1               5

<210> SEQ ID NO 51
<211> LENGTH: 401
<212> TYPE: PRT
<213> ORGANISM: Pseudomonas putida

<400> SEQUENCE: 51

Met Leu Glu Lys His Arg Val Leu Asp Ser Ala Pro Glu Tyr Val Asp
1               5                   10                  15

Lys Lys Lys Tyr Leu Trp Ile Leu Ser Thr Leu Trp Pro Ala Thr Pro
                20                  25                  30

Met Ile Gly Ile Trp Leu Ala Asn Glu Thr Gly Trp Gly Ile Phe Tyr
            35                  40                  45

Gly Leu Val Leu Leu Val Trp Tyr Gly Ala Leu Pro Leu Leu Asp Ala
        50                  55                  60

Met Phe Gly Glu Asp Phe Asn Asn Pro Pro Glu Glu Val Val Pro Lys
65                  70                  75                  80

Leu Glu Lys Glu Arg Tyr Tyr Arg Val Leu Thr Tyr Leu Thr Val Pro
                85                  90                  95

Met His Tyr Ala Ala Leu Ile Val Ser Ala Trp Trp Val Gly Thr Gln
            100                 105                 110

Pro Met Ser Trp Leu Glu Ile Gly Ala Leu Ala Leu Ser Leu Gly Ile
        115                 120                 125

Val Asn Gly Leu Ala Leu Asn Thr Gly His Glu Leu Gly His Lys Lys
    130                 135                 140

Glu Thr Phe Asp Arg Trp Met Ala Lys Ile Val Leu Ala Val Val Gly
145                 150                 155                 160

Tyr Gly His Phe Phe Ile Glu His Asn Lys Gly His His Arg Asp Val
                165                 170                 175

Ala Thr Pro Met Asp Pro Ala Thr Ser Arg Met Gly Glu Ser Ile Tyr
            180                 185                 190

Lys Phe Ser Ile Arg Glu Ile Pro Gly Ala Phe Ile Arg Ala Trp Gly
        195                 200                 205

Leu Glu Glu Gln Arg Leu Ser Arg Arg Gly Gln Ser Val Trp Ser Phe
    210                 215                 220

Asp Asn Glu Ile Leu Gln Pro Met Ile Ile Thr Val Ile Leu Tyr Ala
225                 230                 235                 240

Val Leu Leu Ala Leu Phe Gly Pro Lys Met Leu Val Phe Leu Pro Ile
                245                 250                 255
```

Gln Met Ala Phe Gly Trp Trp Gln Leu Thr Ser Ala Asn Tyr Ile Glu
            260                 265                 270

His Tyr Gly Leu Leu Arg Gln Lys Met Glu Asp Gly Arg Tyr Glu His
        275                 280                 285

Gln Lys Pro His His Ser Trp Asn Ser Asn His Ile Val Ser Asn Leu
    290                 295                 300

Val Leu Phe His Leu Gln Arg His Ser Asp His His Ala His Pro Thr
305                 310                 315                 320

Arg Ser Tyr Gln Ser Leu Arg Asp Phe Pro Gly Leu Pro Ala Leu Pro
            325                 330                 335

Thr Gly Tyr Pro Gly Ala Phe Leu Met Ala Met Ile Pro Gln Trp Phe
        340                 345                 350

Arg Ser Val Met Asp Pro Lys Val Val Asp Trp Ala Gly Gly Asp Leu
    355                 360                 365

Asn Lys Ile Gln Ile Asp Asp Ser Met Arg Glu Thr Tyr Leu Lys Lys
370                 375                 380

Phe Gly Thr Ser Ser Ala Gly His Ser Ser Thr Ser Ala Val Ala
385                 390                 395                 400

Ser

<210> SEQ ID NO 52
<211> LENGTH: 173
<212> TYPE: PRT
<213> ORGANISM: Pseudomonas putida

<400> SEQUENCE: 52

Met Ala Ser Tyr Lys Cys Pro Asp Cys Asn Tyr Val Tyr Asp Glu Ser
1               5                   10                  15

Ala Gly Asn Val His Glu Gly Phe Ser Pro Gly Thr Pro Trp His Leu
            20                  25                  30

Ile Pro Glu Asp Trp Cys Cys Pro Asp Cys Ala Val Arg Asp Lys Leu
        35                  40                  45

Asp Phe Met Leu Ile Glu Ser Gly Val Gly Glu Lys Gly Val Thr Ser
    50                  55                  60

Thr His Thr Ser Pro Asn Leu Ser Glu Val Ser Gly Thr Ser Leu Thr
65                  70                  75                  80

Ala Glu Ala Val Val Ala Pro Thr Ser Leu Glu Lys Leu Pro Ser Ala
            85                  90                  95

Asp Val Lys Gly Gln Asp Leu Tyr Lys Thr Gln Pro Pro Arg Ser Asp
        100                 105                 110

Ala Gln Gly Gly Lys Ala Tyr Leu Lys Trp Ile Cys Ile Thr Cys Gly
    115                 120                 125

His Ile Tyr Asp Glu Ala Leu Gly Asp Glu Ala Glu Gly Phe Thr Pro
130                 135                 140

Gly Thr Arg Phe Glu Asp Ile Pro Asp Asp Trp Cys Cys Pro Asp Cys
145                 150                 155                 160

Gly Ala Thr Lys Glu Asp Tyr Val Leu Tyr Glu Glu Lys
            165                 170

<210> SEQ ID NO 53
<211> LENGTH: 385
<212> TYPE: PRT
<213> ORGANISM: Pseudomonas putida

<400> SEQUENCE: 53

Met Ala Ile Val Val Val Gly Ala Gly Thr Ala Gly Val Asn Ala Ala

```
  1               5                  10                 15
Phe Trp Leu Arg Gln Tyr Gly Tyr Lys Gly Glu Ile Arg Ile Phe Ser
            20                  25                 30

Arg Glu Ser Val Ala Pro Tyr Gln Arg Pro Leu Ser Lys Ala Phe
            35                  40                 45

Leu Thr Ser Glu Ile Ala Glu Ser Ala Val Pro Leu Lys Pro Glu Gly
             50                  55                 60

Phe Tyr Thr Asn Asn Asn Ile Thr Ile Ser Leu Asn Thr Pro Ile Val
 65                  70                  75                 80

Ser Ile Asp Val Gly Arg Lys Ile Val Ser Ser Lys Asp Gly Lys Glu
                 85                  90                 95

Tyr Ala Tyr Glu Lys Leu Ile Leu Ala Thr Pro Ala Ser Ala Arg Arg
                100                 105                110

Leu Thr Cys Glu Gly Ser Glu Leu Ser Gly Val Cys Tyr Leu Arg Ser
                115                 120                125

Met Glu Asp Ala Lys Asn Leu Arg Arg Lys Leu Val Glu Ser Ala Ser
    130                 135                 140

Val Val Val Leu Gly Gly Val Ile Gly Leu Glu Val Ala Ser Ala
145                 150                 155                160

Ala Val Gly Leu Gly Lys Arg Val Thr Val Ile Glu Ala Thr Pro Arg
                165                 170                 175

Val Met Ala Arg Val Val Thr Pro Ala Ala Ala Asn Leu Val Arg Ala
            180                 185                 190

Arg Leu Glu Ala Glu Gly Ile Glu Phe Lys Leu Asn Ala Lys Leu Thr
        195                 200                 205

Ser Ile Lys Gly Arg Asn Gly His Val Glu Gln Cys Val Leu Glu Ser
    210                 215                 220

Gly Glu Glu Ile Gln Ala Asp Leu Ile Val Val Gly Ile Gly Ala Ile
225                 230                 235                240

Pro Glu Leu Glu Leu Ala Thr Glu Ala Ala Leu Glu Val Ser Asn Gly
                245                 250                 255

Val Val Val Asp Asp Gln Met Cys Thr Ser Asp Thr Ser Ile Tyr Ala
            260                 265                 270

Ile Gly Asp Cys Ala Met Ala Arg Asn Pro Phe Trp Gly Thr Met Val
        275                 280                 285

Arg Leu Glu Thr Ile His Asn Ala Val Thr His Ala Gln Ile Val Ala
        290                 295                 300

Ser Ser Ile Cys Gly Thr Ser Thr Pro Ala Pro Thr Pro Pro Arg Phe
305                 310                 315                320

Trp Ser Asp Leu Lys Gly Met Ala Leu Gln Gly Leu Gly Ala Leu Lys
                325                 330                 335

Asp Tyr Asp Lys Leu Val Val Ala Ile Asn Asn Glu Thr Leu Glu Leu
            340                 345                 350

Glu Val Leu Ala Tyr Lys Gln Glu Arg Leu Ile Ala Thr Glu Thr Ile
        355                 360                 365

Asn Leu Pro Lys Arg Gln Gly Ala Leu Ala Gly Ser Ile Lys Leu Pro
    370                 375                 380

Asp
385
```